(12) United States Patent
Modlin et al.

(10) Patent No.: US 10,709,714 B2
(45) Date of Patent: Jul. 14, 2020

(54) GASTRIN ANTAGONISTS FOR TREATMENT AND PREVENTION OF OSTEOPOROSIS

(71) Applicant: CL BioSciences LLC, Charlestown (KN)

(72) Inventors: Irvin Mark Modlin, Woodbridge, CT (US); Mark Kidd, New Haven, CT (US)

(73) Assignee: Clifton Life Sciences LLC, Charlestown (KN)

( * ) Notice: Subject to any disclaimer, the term of this patent is extended or adjusted under 35 U.S.C. 154(b) by 0 days.

(21) Appl. No.: 14/550,233

(22) Filed: Nov. 21, 2014

(65) Prior Publication Data

US 2015/0148339 A1   May 28, 2015

Related U.S. Application Data

(60) Provisional application No. 61/907,982, filed on Nov. 22, 2013.

(51) Int. Cl.
*A61K 31/5513* (2006.01)
*A61K 45/06* (2006.01)

(52) U.S. Cl.
CPC .......... *A61K 31/5513* (2013.01); *A61K 45/06* (2013.01)

(58) Field of Classification Search
CPC .. A61P 1/04; A61P 15/00; A61P 19/08; A61P 35/00; A61P 43/00; A61P 19/10; A61K 45/06; A61K 31/5513
See application file for complete search history.

(56) References Cited

U.S. PATENT DOCUMENTS

| | | | |
|---|---|---|---|
| 5,318,981 A | 6/1994 | Woodruff | |
| 5,399,565 A | 3/1995 | Greenwood et al. | |
| 5,451,602 A | 9/1995 | Woodruff | |
| 5,541,182 A | 7/1996 | Satoh et al. | |
| 5,688,943 A | 11/1997 | Ryder et al. | |
| 5,728,829 A | 3/1998 | Semple et al. | |
| 5,922,883 A | 7/1999 | Hutchinson | |
| 5,962,451 A | 10/1999 | Ryder et al. | |
| 6,548,066 B1 | 4/2003 | Michaeli et al. | |
| 6,566,080 B1 | 5/2003 | Kopin et al. | |
| 6,747,024 B1 | 6/2004 | Auvin et al. | |
| 7,285,565 B2 | 10/2007 | Zhu et al. | |
| 7,429,604 B2 | 9/2008 | Corte et al. | |
| 7,465,808 B2 | 12/2008 | Barrett et al. | |
| 7,479,471 B2 | 1/2009 | Minn et al. | |
| 7,524,837 B2 | 4/2009 | Abdel-Magid | |
| 2003/0049698 A1 | 3/2003 | Wang | |
| 2003/0086941 A1 | 5/2003 | Michaeli et al. | |
| 2003/0087306 A1 | 5/2003 | Christensen et al. | |
| 2003/0091574 A1 | 5/2003 | Gevas et al. | |
| 2003/0180798 A1 | 9/2003 | Kopin et al. | |
| 2003/0191279 A1 | 10/2003 | Goldstein et al. | |
| 2003/0220365 A1 | 11/2003 | Stewart et al. | |
| 2004/0001842 A1 | 1/2004 | Michaeli et al. | |
| 2004/0138207 A1 | 7/2004 | Yamano | |
| 2004/0138285 A1 | 7/2004 | Okazaki | |
| 2004/0224983 A1 | 11/2004 | Allison et al. | |
| 2005/0026911 A1 | 2/2005 | Magid et al. | |
| 2005/0038032 A1 | 2/2005 | Allison et al. | |
| 2005/0038248 A1 | 2/2005 | Henderson et al. | |
| 2005/0042283 A1 | 2/2005 | Wang | |
| 2005/0043310 A1 | 2/2005 | Deng et al. | |
| 2005/0176796 A1 | 8/2005 | d'Alessio et al. | |
| 2006/0003993 A1 | 1/2006 | McDonald et al. | |
| 2006/0069286 A1 | 3/2006 | Allison et al. | |
| 2006/0140962 A1 | 6/2006 | Gevas et al. | |
| 2007/0142448 A1 | 6/2007 | Hanazawa et al. | |
| 2007/0185093 A1 | 8/2007 | Buck et al. | |
| 2007/0219237 A1 | 9/2007 | Matsumoto et al. | |
| 2007/0276016 A1 | 11/2007 | Allison et al. | |
| 2007/0293482 A1 | 12/2007 | Dowdell et al. | |
| 2008/0009477 A1 | 1/2008 | Hutchinson et al. | |

(Continued)

FOREIGN PATENT DOCUMENTS

| | | |
|---|---|---|
| EP | 0411668 | 2/1991 |
| EP | 0717732 | 6/1996 |

(Continued)

OTHER PUBLICATIONS

Garnero et al. (Journal of Bone and Mineral Research, vol. 11, No. 3, 1996).*
Sharma et al. (Gut 1984, 25, 957-964).*
Dacha et al. (Gastroenterol Rep (Oxf). Aug. 2015; 3(3): 201-208).*
Berna, Mark J. et al. "Role of CCK/gastrin receptors in gastrointestinal/ metabolic diseases and results of human studies using gastrin/ CCK receptor agonists /antagonists in these diseases", *Curr Top Med Chem*, 2007, vol. 7, No. 12, p. 1211-1231.
Boyce et al. "Netazepide, a gastrin/ CCK2 receptor antagonist, causes dose-dependent, persistent inhibition of the responses to pentagastrin in healthy subjects", *British Journal of Clinical Pharmacology*, 2012, vol. 76, No. 5, p. 689-698.
Fossmark et al. "Treatment of gastric carcinoid type 1 with the gastrin receptor antagonist netazepide (YF476) results in regression of tumors and normalisation of serum chromogranin A", *Alimentary Pharmacology & Therapeutics*, Oct. 16, 2012, vol. 36, p. 1067-1075.

(Continued)

*Primary Examiner* — Kortney L. Klinkel
*Assistant Examiner* — William Y Lee
(74) *Attorney, Agent, or Firm* — Cooley LLP; Ivor R. Elrifi; Matthew Pavao

(57) ABSTRACT

The provided embodiments are based in some aspects on the demonstration herein of a role for gastrin in regulating the aging gut-ovary axis and effects of targeting gastrin activity in reversing gastrin-mediated bone loss. Provided are methods, compositions and agents, including gastrin antagonists, for treatment, amelioration, and prevention of bone diseases and conditions. Methods for treating a bone disease or condition associated with hypergastrinemia in a subject in need thereof may comprise administering to the subject at least one dose of a therapeutically effective amount of a gastrin receptor-targeting agent, thereby treating the bone disease or condition associated with hypergastrinemia.

26 Claims, 58 Drawing Sheets

Specification includes a Sequence Listing.

(56) References Cited

U.S. PATENT DOCUMENTS

| | | |
|---|---|---|
| 2008/0076918 A1 | 3/2008 | Allison et al. |
| 2008/0103151 A9 | 5/2008 | Chafeev et al. |
| 2008/0103300 A1 | 5/2008 | Deng et al. |
| 2008/0124741 A1 | 5/2008 | Dai et al. |
| 2008/0132511 A1 | 6/2008 | Allison et al. |
| 2008/0161293 A1 | 7/2008 | Yoshinaga et al. |
| 2008/0200367 A1 | 8/2008 | Carley et al. |
| 2008/0214519 A1 | 9/2008 | Koike et al. |
| 2009/0004200 A1 | 1/2009 | Gevas et al. |
| 2009/0124633 A1 | 5/2009 | Jonczyk et al. |
| 2009/0191232 A1 | 7/2009 | Gevas et al. |
| 2009/0239841 A1 | 9/2009 | Hutchison et al. |
| 2009/0291977 A1 | 11/2009 | Jinno et al. |
| 2010/0048532 A1 | 2/2010 | Koike et al. |
| 2010/0086553 A1 | 4/2010 | Yoshinaga et al. |
| 2010/0129382 A1 | 5/2010 | Gevas et al. |
| 2010/0143366 A1 | 6/2010 | Yoshinaga et al. |
| 2010/0163070 A1 | 7/2010 | Malle et al. |
| 2010/0261909 A1 | 10/2010 | Alonso et al. |
| 2010/0292240 A1 | 11/2010 | Allison et al. |
| 2011/0105515 A1 | 5/2011 | Myers et al. |
| 2011/0172335 A1 | 7/2011 | Deshpande |
| 2012/0010198 A1 | 1/2012 | Carley et al. |
| 2012/0010401 A1 | 1/2012 | Terauchi |
| 2012/0041078 A1 | 2/2012 | Techdjian et al. |
| 2012/0115820 A1 | 5/2012 | Takahashi et al. |
| 2012/0122839 A1 | 5/2012 | Burdack et al. |
| 2012/0192888 A1 | 8/2012 | Philippe et al. |
| 2012/0208819 A1 | 8/2012 | Arndt et al. |
| 2012/0231083 A1 | 9/2012 | Carley et al. |
| 2013/0029967 A1 | 1/2013 | Fernandez et al. |
| 2013/0045229 A1 | 2/2013 | Iadonato et al. |
| 2013/0116434 A1 | 5/2013 | Schrock et al. |
| 2013/0281523 A1 | 10/2013 | Letendre et al. |
| 2014/0031547 A1 | 1/2014 | Sheridan et al. |
| 2014/0045755 A1 | 2/2014 | Carley et al. |
| 2014/0045855 A1 | 2/2014 | Biswas et al. |

FOREIGN PATENT DOCUMENTS

| | | |
|---|---|---|
| EP | 1747800 | 1/2007 |
| EP | 1898921 | 3/2008 |
| JP | H 0228181 A | 1/1990 |
| JP | 2008222557 | 9/2008 |
| RU | 2379043 C2 | 1/2010 |
| WO | WO 93/07129 A1 | 4/1993 |
| WO | WO93/12817 | 7/1993 |
| WO | WO 9507261 | 3/1995 |
| WO | WO 9959628 | 11/1999 |
| WO | WO 9962908 | 12/1999 |
| WO | WO 2000075145 | 12/2000 |
| WO | WO 2001035899 | 5/2001 |
| WO | WO 2001077685 | 10/2001 |
| WO | WO 2002000651 | 1/2002 |
| WO | WO2005007107 | 1/2005 |
| WO | WO 2006051312 | 5/2005 |
| WO | WO 2006133197 | 12/2006 |
| WO | WO 2007026218 | 3/2007 |
| WO | WO 2007031860 | 3/2007 |
| WO | WO 2007072142 | 6/2007 |
| WO | WO 2008046082 | 4/2008 |
| WO | WO 2008059373 | 5/2008 |
| WO | WO 2008114123 | 9/2008 |
| WO | WO 2008124518 | 10/2008 |
| WO | WO 2008124524 | 10/2008 |
| WO | WO 2010036316 | 4/2010 |
| WO | WO 2011063164 | 5/2011 |
| WO | WO 2013017479 | 2/2013 |
| WO | WO 2013017480 | 2/2013 |
| WO | WO 2013126797 | 8/2013 |
| WO | WO 2013158928 | 10/2013 |
| WO | WO 2014019344 | 2/2014 |

OTHER PUBLICATIONS

Ito et al. "Association of Long-Term Proton Pump Inhibitor Therapy with Bone Fractures and Effects on Absorption of Calcium, Vitamin B12, Iron, and Magnesium", *Current Gastroenterol Rep*, Dec. 2010, vol. 12, No. 6, p. 448-457.

Yang et al. "Long-term Proton Pump Inhibitor Therapy and Risk of Hip Fracture", *Journal of the American Medical Association*, Dec. 27, 2006, vol. 296, No. 24, 2947-2953.

Yang et al. "Proton Pump Inhibitor Therapy and Osteoporosis", *Current Drug Safety*, 2008, 3, 204-209.

Third Party Observations in Relation to International Application No. PCT/US2014/066832 "Gastrin Antagonists (e.g. YF476, Netazepide) for Treatment and Prevention of Osteoporosis", dated Mar. 17, 2016.

B. Clarke, "Normal bone anatomy and physiology", Clin J Am Soc Nephroi.; 3: S131-139. doi: 110.2215/CJN.04151206, (2008).

B.L. Clarke, "Khosla S. Physiology of bone loss", Radiol Clin North Am. 2010, 48: 483-495. doi: 410.1016/j.rcl., 1002.1014, (2010).

S. Sherman, "Preventing and treating osteoporosis: strategies at the millennium", Y Acad Sci.; 949: 188-197, (2001).

P.S. Wang et al., "HMG-CoA reductase inhibitors and the risk of hip fractures in elderly patients", Jama.;283: 3211-3216, (2000).

CR Dunstan et al. "Systemic administration of acidic fibroblast growth factor (FGF-1) prevents bone loss and increases new bone formation in ovariectomized rats", J. Bone Miner Res., 14: 953-959, (1999).

J. Reeve, "Recombinant human parathyroid hormone", BMJ., 324: 435-436, (2002).

WR McKane et al., "Role of calcium intake in modulating age-related increases in parathyroid function and bone resorption", J Clin Endocrinol Metab., 81: 1699-1703, (1996).

RD Lindeman et al., "Longitudinal studies on the rate of decline in renal function with age", J Am Geriatr Soc.; 33: 278-285, (1985).

P. Ireland et al., "Effect of dietary calcium and age on jejunal calcium absorption in humans studied by intestinal perfusion", J Clin Invest., 52: 2672-2681, (1973).

LM Donini, "Eating habits and appetite control in the elderly: the anorexia of aging", Int Psychogeriatr., 15: 73-87, (2003).

A Portale et al., "Aging alters calcium regulation of serum concentration of parathyroid hormone in healthy men", Am J Physiol.; 272: E139-146, (1997).

MF Holick et al., "Prevalence of Vitamin D inadequacy among postmenopausal North American women receiving osteoporosis therapy", J Clin Endocrinol Metab.; 90: 3215-3224, (2005).

M. Kekki et al., "Age- and sex-related behaviour of gastric acid secretion at the population level", Scand J Gastroenterol., 17: 737-743, (1982).

LD Quarles et al., "Extracellular calcium-sensing receptors in the parathyroid gland, kidney, and other tissues", Curr Opin Nephrol Hypertens., 12: 349-355, (2003).

RA Chen, "Role of the calcium-sensing receptor in parathyroid gland physiology", Am J Physiol Renal Physiol., 286: F1005-1011, (2004).

DS McGehee et al., Mechanism of extracellular Ca2+ receptor-stimulated hormone release from sheep thyroid parafollicular cells J Physiol.;502 ( Pt 1): 31-44, (1997).

Freichel M, Zink-Lorenz A, Holloschi A, Hefner M, Flockerzi V, Raue F. Expression of a calcium-sensing receptor in a human medullary thyroid carcinoma cell line and its contribution to calcitonin secretion. Endocrinology. 1996;137: 3842-3848.

Silver IA, Murrills RJ, Etherington DJ. Microelectrode studies on the acid microenvironment beneath adherent macrophages and osteoclasts. Exp Cell Res. 1988;175: 266-276.

Chang W, Tu C, Bajra R, et al. Calcium sensing in cultured chondrogenic RCJ3.1C5.18 cells. Endocrinology. 1999;140: 1911-1919.

Ray JM, Squires PE, Curtis SB, Meloche MR, Buchan AM. Expression of the calcium-sensing receptor on human antral gastrin cells in culture. J Clin Invest. 1997;99: 2328-2333.

Buchan AM, Squires PE, Ring M, Meloche RM. Mechanism of action of the calcium-sensing receptor in human antral gastrin cells. Gastroenterology. 2001;120: 1128-1139.

(56) References Cited

OTHER PUBLICATIONS

Selking O, Gustaysson S, Johansson H, Lundqvist G. Effect of parathyroid hormone on gastrin and somatostatin release from the gastric antrum. Ups J Med Sci. 1981;86: 259-267.

Bolman RM, 3rd, Cooper CW, Garner SC, Munson PL, Wells SA, Jr. Stimulation of gastrin secretion in the pig by parathyroid hormone and its inhibition by thyrocalcitonin. Endocrinology. 1977;100: 1014-1021.

Naot D, Cornish J. The role of peptides and receptors of the calcitonin family in the regulation of bone metabolism. Bone. 2008;43: 813-818.

Tian J, Berton TR, Shirley SH, et al. Developmental stage determines estrogen receptor alpha expression and non-genomic mechanisms that control IGF-1 signaling and mammary proliferation in mice. J Clin Invest. 2012;122: 192-204. doi: 110.1172/JC142204. Epub Dec. 4, 2011 42219.

Kidd M, Hauso Ø, Drozdov I, Gustafsson B, Modlin I. Delineation of the chemomechanosensory regulation of gastrin secretion using pure rodent G cells. Gastroenterology. 2009;(in press).

Deal C. Potential new drug targets for osteoporosis. Nat Clin Pract Rheumatol. 2009;5: 20-27.

Barete S, Assous N, de Gennes C, et al. Systemic mastocytosis and bone involvement in a cohort of 75 patients. Ann Rheum Dis. 2010;69: 1838-1841. doi: 1810.1136/ard.2009.124511. Epub Jun. 12, 2010 124522.

Biosse-Duplan M, Baroukh B, Dy M, de Vernejoul Mc, Saffar Jl. Histamine promotes osteoclastogenesis through the differential expression of histamine receptors on osteoclasts and osteoblasts. Am J Pathol. 2009;174: 1426-1434. doi: 1410.2353/ajpath.2009.080871. Epub Mar. 8, 2009 080875.

Dobigny C, Saffar JL. H1 and H2 histamine receptors modulate osteoclastic resorption by different pathways: evidence obtained by using receptor antagonists in a rat synchronized resorption model. J Cell Physiol. 1997;173: 10-18.

Meh A, Sprogar S, Vaupotic T, et al. Effect of cetirizine, a histamine (H(1)) receptor antagonist, on bone modeling during orthodontic tooth movement in rats. Am J Orthod Dentofacial Orthop. 2011;139: e323-329. doi: 310.1016/j.ajodo.2009.1011.1013.

Ohtsu H. Histamine synthesis and lessons learned from histidine decarboxylase deficient mice. Adv Exp Med Biol. 2010;709: 21-31.

Bliss PW, Healey ZV, Arebi N, Calam J. Nalpha-methyl histamine and histamine stimulate gastrin release from rabbit G-cells via histamine H2-receptors. Aliment Pharmacol Ther. 1999;13: 1669-1674.

Gustafsson BI, Westbroek I, Waarsing JH, et al. Long-term serotonin administration leads to higher bone mineral density, affects bone architecture, and leads to higher femoral bone stiffness in rats. J Cell Biochem. 2006;97: 1283-1291.

Yadav VK, Ryu JH, Suda N, et al. Lrp5 controls bone formation by inhibiting serotonin synthesis in the duodenum. Cell. 2008;135: 825-837.

Nilsson O, Ahlman H, Geffard M, Dahlstrom A, Ericson LE. Bipolarity of duodenal enterochromaffin cells in the rat. Cell Tissue Res. 1987;248: 49-54.

Lee GS, Simpson C, Sun BH, et al. Measurement of plasma, serum, and platelet serotonin in individuals with high bone mass and mutations in LRP5. J Bone Miner Res. 2013;26.

Diem SJ, Ruppert K, Cauley JA, et al. Rates of Bone Loss Among Women Initiating Antidepressant Medication Use in Midlife. J Clin Endocrinol Metab. 2013;3: 3.

Van Dijk SC, de Herder WW, Kwekkeboom DJ, et al. 5-HIAA excretion is not associated with bone metabolism in carcinoid syndrome patients. Bone. 2012;50: 1260-1265. doi: 1210.1016/j.bone.2012.1202.1637. Epub Mar. 2012 1268.

Walsh JS, Newell-Price JD, DeBono M, Adaway J, Keevil B, Eastell R. Circulating serotonin and bone density, structure, and turnover in carcinoid syndrome. J Clin Endocrinol Metab. 2013;98: 2902-2907. doi: 2910.1210/jc.2012-4174. Epub Apr. 2013 2930.

Reubi JC, Schaer JC, Waser B. Cholecystokinin(CCK)-A and CCK-B/gastrin receptors in human tumors. Cancer Res. 1997;57: 1377-1386.

Windeck R, Brown EM, Gardner DG, Aurbach GD. Effect of gastrointestinal hormones on isolated bovine parathyroid cells. Endocrinology. 1978;103: 2020-2026.

Gagnemo-Persson R, Samuelsson A, Hakanson R, Persson P. Chicken parathyroid hormone gene expression in response to gastrin, omeprazole, ergocalciferol, and restricted food intake. Calcif Tissue Int. 1997;61: 210-215.

Williams GA, Longley RS, Bowser EN, et al. Parathyroid hormone secretion in normal man and in primary hyperparathyroidism: role of histamine H2 receptors. J Clin Endocrinol Metab. 1981;52: 122-127.

Gustafsson BI, Thommesen L, Stunes AK, et al. Serotonin and fluoxetine modulate bone cell function in vitro. J. Cell. Biochem., 97:1283-1291, (2006).

Wagner PK, Krause U, Scharle T, Beyer J, Rothmund M. Effect of cimetidine on basal and histamine-induced secretion of parathyroid hormone in vitro. Nephron. 1984;36: 89-93.

Klein I, Lehotay DC, Watson CG, Rogerson B, Levey GS. Human parathyroid adenoma adenylate cyclase: stimulation by histamine that is blocked by cimetidine. Metabolism. 1981;30: 635-637.

Reubi JC, Waser B. Unexpected high incidence of cholecystokinin-B/gastrin receptors in human medullary thyroid carcinomas. Int J Cancer. 1996;67: 644-647.

Amiri-Mosavi A, Ahlman H, Tisell LE, et al. Expression of cholecystokinin-B/gastrin receptors in medullary thyroid cancer. Eur J Surg. 1999;165: 628-631.

Blaker M, de Weerth A, Tometten M, et al. Expression of the cholecystokinin 2-receptor in normal human thyroid gland and medullary thyroid carcinoma. Eur J Endocrinol. 2002;146: 89-96.

Selawry HP, Becker KL, Bivins LE, Snider RH, Silva OL. In vitro studies of calcitonin release in man. Horm Metab Res. 1975;7: 432-437.

Pfragner R, Hofler H, Behmel A, Ingolic E, Walser V. Establishment and characterization of continuous cell line MTC-SK derived from a human medullary thyroid carcinoma. Cancer Res. 1990;50: 4160-4166.

Vantini I, Cominacini L, Piubello W, et al. Effect of exogenous gastrointestinal peptides containing the C-terminal tetrapeptide of gastrin on calcium, calcitonin and parathormone serum levels in man. Hepatogastroenterology. 1981;28: 43-48.

Harris SA, Enger RJ, Riggs BL, Spelsberg TC. Development and characterization of a conditionally immortalized human fetal osteoblastic cell line. J Bone Miner Res. 1995;10: 178-186.

Wan Y. Bone marrow mesenchymal stem cells: fat on and blast off by FGF21. Int J Biochem Cell Biol. 2013;45: 546-549. doi: 510.1016/j.biocel.2012.1012.1014. Epub Dec. 2012 1025.

Mansukhani A, Bellosta P, Sahni M, Basilico C. Signaling by fibroblast growth factors (FGF) and fibroblast growth factor receptor 2 (FGFR2)-activating mutations blocks mineralization and induces apoptosis in osteoblasts. J Cell Biol. 2000;149: 1297-1308.

Hens JR, Wilson KM, Dann P, Chen X, Horowitz MC, Wysolmerski JJ. Topgal mice show that the canonical Wnt signaling pathway is active during bone development and growth and is activated by mechanical loading in vitro. J Bone Miner Res. 2005;20: 1103-1113. Epub Feb. 2005 1114.

Jiang SS, Chen CH, Tseng KY, et al. Gene expression profiling suggests a pathological role of human bone marrow-derived mesenchymal stem cells in aging-related skeletal diseases. Aging (Albany NY). 2011;3: 672-684.

Sheikh MS, Santa Ana CA, Nicar MJ, Schiller LR, Fordtran JS. Gastrointestinal absorption of calcium from milk and calcium salts. N Engl J Med. 1987;317: 532-536.

Goerss JB, Kim CH, Atkinson EJ, Eastell R, O'Fallon WM, Melton LJ, 3rd. Risk of fractures in patients with pernicious anemia. J Bone Miner Res. 1992;7: 573-579.

Nilas L, Christiansen C, Christiansen J. Regulation of vitamin D and calcium metabolism after gastrectomy. Gut. 1985;26: 252-257.

Yang YX, Lewis JD, Epstein S, Metz DC. Long-term proton pump inhibitor therapy and risk of hip fracture. Jama. 2006;296: 2947-2953.

(56) References Cited

OTHER PUBLICATIONS

Kidd M, Modlin IM, Eick GN, Camp RL, Mane SM. Role of CCN2/CTGF in the proliferation of Mastomys enterochromaffin-like cells and gastric carcinoid development. Am J Physiol Gastrointest Liver Physiol. 2007;292: G191-200.

Kidd M, Hinoue T, Eick G, et al. Global expression analysis of ECL cells in Mastomys natalensis gastric mucosa identifies alterations in the AP-1 pathway induced by gastrin-mediated transformation. Physiol Genomics. 2004;20: 131-142.

Kidd M, Siddique ZI, Drozdov I, et al. The CCK(2) receptor antagonist, YF476, inhibits Mastomys ECL cell hyperplasia and gastric carcinoid tumor development. Regul Pept. 2010;162: 52-60.

Shen Z, Xu S, Dewhirst FE, et al. A novel enterohepatic Helicobacter species 'Helicobacter mastomyrinus' isolated from the liver and intestine of rodents. Helicobacter. 2005;10: 59-70.

Jacobson BC, Ferris TG, Shea TL, Mahlis EM, Lee TH, Wang TC. Who is using chronic acid suppression therapy and why? Am J Gastroenterol. 2003;98: 51-58.

Landahl S, Andersson T, Larsson M, et al. Pharmacokinetic study of omeprazole in elderly healthy volunteers. Clin Pharmacokinet. 1992;23: 469-476.

Marshall BJ. Helicobacter pylori. Am J Gastroenterol. 1994;89: S116-128.

Ivanovich P, Fellows H, Rich C. The absorption of calcium carbonate. Ann Intern Med. 1967;66: 917-923.

Recker RR. Calcium absorption and achlorhydria. N Engl J Med. 1985;313: 70-73.

Chonan O, Takahashi R, Yasui H, Watanuki M. Effect of L-lactic acid on the absorption of calcium in gastrectomized rats. J Nutr Sci Vitaminol (Tokyo). 1998;44: 869-875.

Chonan O, Takahashi R, Yasui H, Watanuki M. Effect of L-lactic acid on calcium absorption in rats fed omeprazole. J Nutr Sci Vitaminol (Tokyo). 1998;44: 473-481.

Muhlbauer RC, Schenk RK, Chen D, Lehto-Axtelius D, Hakanson R. Morphometric analysis of gastrectomy-evoked osteopenia. Calcif Tissue Int. 1998;62: 323-326.

Persson P, Hakanson R, Axelson J, Sundler F. Gastrin releases a blood calcium-lowering peptide from the acid-producing part of the rat stomach. Proc Natl Acad Sci U S A. 1989;86: 2834-2838.

Hakanson R, Persson P, Axelson J, Johnell O, Sundler F. Evidence that gastrin enhances $^{45}Ca$ uptake into bone through release of a gastric hormone. Regul Pept. 1990;28: 107-118.

Krishnamra N, Limlomwongse L. Acute and long-term effects of gastrin on muscle and bone calcium uptake in rats. J Nutr Sci Vitaminol (Tokyo). 1995;41: 687-697.

Bo-Linn GW, Davis GR, Buddrus DJ, Morawski SG, Santa Ana C, Fordtran JS. An evaluation of the importance of gastric acid secretion in the absorption of dietary calcium. J Clin Invest. 1984;73: 640-647.

O'Connell MB, Madden DM, Murray AM, Heaney RP, Kerzner LJ. Effects of proton pump inhibitors on calcium carbonate absorption in women: a randomized crossover trial. Am J Med. 2005;118: 778-781.

Eom CS, Park SM, Myung SK, Yun JM, Ahn JS. Use of acid-suppressive drugs and risk of fracture: a meta-analysis of observational studies. Ann Fam Med. 2011;9: 257-267. doi: 210.1370/afm. 1243.

Sokoloff L, Snell KC, Stewart HL. Degenerative joint disease in Praomys (Mastomys) natalensis. Ann Rheum Dis. 1967;26: 146-154.

Pialat JB, Vilayphiou N, Boutroy S, et al. Local topological analysis at the distal radius by HR-pQCT: Application to in vivo bone microarchitecture and fracture assessment in the Ofely study. Bone. 2012;51: 362-368. doi: 310.1016/j.bone.2012.1006.1008. Epub Jun. 2012 1020.

Cho SW, Yang JY, Her SJ, et al. Osteoblast-targeted overexpression of PPARgamma inhibited bone mass gain in male mice and accelerated ovariectomy-induced bone loss in female mice. J Bone Miner Res. 2011;26: 1939-1952. doi: 1910.1002/jbmr.1366.

Fazeli PK, Horowitz MC, MacDougald OA, et al. Marrow fat and bone—new perspectives. J Clin Endocrinol Metab. 2013;98: 935-945. doi: 910.1210/jc.2012-3634. Epub Feb. 2013 1217.

Kim HY, Alarcon C, Pourteymour S, Wergedal JE, Mohan S. Disruption of claudin-18 diminishes ovariectomy-induced bone loss in mice. Am J Physiol Endocrinol Metab. 2013;304: E531-537. doi: 510.1152/ajpendo.00408.02012. Epub 02013 Jan 00408.

Zhao Q, Shen X, Zhang W, Zhu G, Qi J, Deng L. Mice with increased angiogenesis and osteogenesis due to conditional activation of HIF pathway in osteoblasts are protected from ovariectomy induced bone loss. Bone. 2012;50: 763-770. doi: 710.1016/j.bone. 2011.1012.1003. Epub Dec. 2011 1013.

Bouxsein ML, Devlin MJ, Glatt V, Dhillon H, Pierroz DD, Ferrari SL. Mice lacking beta-adrenergic receptors have increased bone mass but are not protected from deleterious skeletal effects of ovariectomy. Endocrinology. 2009;150: 144-152. doi: 110.1210/en. 2008-0843. Epub Sep. 2008 1218.

Ooi A, Saad RA, Moorjani N, Amer KM. Effective symptomatic relief of hypertrophic pulmonary osteoarthropathy by video-assisted thoracic surgery truncal vagotomy. Ann Thorac Surg. 2007;83: 684-685.

Sills M, Pozderac RV. Early diagnosis of Pancoast's tumor facilitated by bone scanning. Radiology. 1974;113: 391-392.

Malfertheiner P, Fass R, Quigley EM, et al. Review article: from gastrin to gastro-oesophageal reflux disease—a century of acid suppression. Aliment Pharmacol Ther. 2006;23: 683-690.

Bordi C, D'Adda T, Azzoni C, Ferraro G. Classification of gastric endocrine cells at the light and electron microscopical levels. Microsc Res Tech. 2000;48: 258-271.

Modlin IM, Tang LH. The gastric enterochromaffin-like cell: an enigmatic cellular link. Gastroenterology. 1996;111: 783-810.

Sandor A, Kidd M, Lawton G, Miu K, Tang L, Modlin I. Neurohormonal Regulation of rat ECL cell histamine secretion. Gastroenterology. 1996;110: 1084-1092.

Lehto-Axtelius D, Chen D, Surve VV, Hakanson R. Post-gastrectomy osteopenia in the rat: bone structure is preserved by retaining 10%-30% of the oxyntic gland area. Scand J Gastroenterol. 2002;37: 437-443.

Deyama Y, Kikuiri T, Ohnishi G, et al. Histamine stimulates production of osteoclast differentiation factor/receptor activator of nuclear factor-kappaB ligand by osteoblasts. Biochem Biophys Res Commun. 2002;298: 240-246.

Ikawa Y, Yonekawa T, Ohkuni Y, Kuribayashi M, Fukino K, Ueno K. A comparative study of histamine activities on differentiation of osteoblasts and osteoclasts. J Toxicol Sci. 2007;32: 555-564.

Cappellen D, Luong-Nguyen NH, Bongiovanni S, Grenet O, Wanke C, Susa M. Transcriptional program of mouse osteoclast differentiation governed by the macrophage colony-stimulating factor and the ligand for the receptor activator of NFkappa B. J Biol Chem. 2002;277: 21971-21982.

Lesclous P, Schramm F, Gallina S, Baroukh B, Guez D, Saffar JL. Histamine mediates osteoclastic resorption only during the acute phase of bone loss in ovariectomized rats. Exp Physiol. 2006;91: 561-570.

Abrahamsen B, Vestergaard P. Proton pump inhibitor use and fracture risk—effect modification by histamine H1 receptor blockade. Observational case-control study using National Prescription Data. Bone. 2013;57: 269-271. doi: 210.1016/j.bone.2013.1008. 1013. Epub Aug. 2013 1022.

Tanaka S, Hamada K, Yamada N, et al. Gastric acid secretion in L-histidine decarboxylase-deficient mice. Gastroenterology. 2002;122: 145-155.

Fitzpatrick LA, Buzas E, Gagne TJ, et al. Targeted deletion of histidine decarboxylase gene in mice increases bone formation and protects against ovariectomy-induced bone loss. Proc Natl Acad Sci U S A. 2003;100: 6027-6032.

Axelson J, Persson P, Gagnemo-Persson R, Hakanson R. Importance of the stomach in maintaining calcium homoeostasis in the rat. Gut. 1991;32: 1298-1302.

Naveh-Many T, Almogi G, Livni N, Silver J. Estrogen receptors and biologic response in rat parathyroid tissue and C cells. J Clin Invest. 1992;90: 2434-2438.

(56) References Cited

OTHER PUBLICATIONS

Komarova SV. Mathematical model of paracrine interactions between osteoclasts and osteoblasts predicts anabolic action of parathyroid hormone on bone. Endocrinology. 2005;146: 3589-3595. Epub Apr. 2005 3528.
Black JW. Reflections on some pilot trials of gastrin receptor blockade in pancreatic cancer. Eur J Cancer. 2009;45: 360-364. doi: 310.1016/j.ejca.2008.1011.1026. Epub Jan. 2009 1017.
Fossmark R, Sordal O, Jianu CS, et al. Treatment of gastric carcinoids type 1 with the gastrin receptor antagonist netazepide (YF476) results in regression of tumours and normalisation of serum chromogranin A. Aliment Pharmacol Ther. 2012;36: 1067-1075. doi: 1010.1111/apt.12090. Epub Oct. 1, 2012 12016.
Boyce M, Warrington S, Black J. Netazepide, a gastrin/CCK2 receptor antagonist, causes dose-dependent, persistent inhibition of the responses to pentagastrin in healthy subjects. Br J Clin Pharmacol. 2013;76: 689-698. doi: 610.1111/bcp.12099.
Semple G, Ryder H, Rooker DP, et al. (3R)-N-(1-(tert-butylcarbonylmethyl)-2,3-dihydro-2-oxo-5-(2-pyridyl)-1H-1,4-benzo diazepin-3-yl)-N'-(3-(methylamino)phenyl)urea (YF476): a potent and orally active gastrin/CCK-B antagonist. J Med Chem. 1997;40: 331-341.
Kidd M, Modlin IM, Black JW, Boyce M, Culler M. A comparison of the effects of gastrin, somatostatin and dopamine receptor ligands on rat gastric enterochromaffin-like cell secretion and proliferation. Regul Pept. 2007;143: 109-117. Epub Apr. 2007 2029.
Nilsson I, Monstein HJ, Lindstrom E, Hakanson R, Svensson S. Pharmacological analysis of CCK(2) receptor ligands using COS-7 and SK-N-MC cells, expressing the human CCK(2) receptor. Regul Pept. 2002;103: 29-37.
Kitano M, Norlen P, Ding XQ, Nakamura S, Hakanson R. Long-lasting cholecystokinin(2) receptor blockade after a single subcutaneous injection of YF476 or YM022. Br J Pharmacol. 2000;130: 699-705.
Thorsten, Schinke et al., Impaired gastric acidification negatively affects calcium homeostasis and bone mass, Nature Medicine, vol. 15, No. 6, May 17, 2009, pp. 674-681.
Wang Z et al., Effect of estrogen or progestogen injection on serum gastrin levels and gastric acid secretion of ovariectomized rats, ACTA Physiologica Sinica, vol. 39, No. 3, 1987, pp. 269-274.
Akiyama T, Tachibana I, Hirohata Y, Shirohara H, Yamamoto M, et al. (1996) "Pharmacological profile of TP-680, a new cholecystokininA receptor antagonist", Br J Pharmacol 117: 1558-1564.
Augelli-Szafran CE, Horwell DC, Kneen C, Ortwine DF, Pritchard MC, et al. (1996) "Cholecystokinin B antagonists. Synthesis and quantitative structure-activity relationships of a series of C-terminal analogues of CI-988", Bioorg & Med Chem 4: 1733-1745.
Barrett TD, Lagaud G, Wagaman P, Freedman JM, Yan W, et al. (2012) "The cholecystokinin CCK2 receptor antagonist, JNJ-26070109, inhibits gastric acid secretion and prevents omeprazole-induced acid rebound in the rat", Br J Pharmacol 166: 1684-1693.
Bertrand P, Bohme GA, Durieux C, Guyon C, Capet M, et al. (1994) "Pharmacological properties of ureido-acetamides, new potent and selective non-peptide Cckb/gastrin receptor antagonists", Eur J Pharmacol 262: 233-245.
Black, J. et al. "Reflections on some pilot trials of gastrin receptor blockade in pancreatic cancer", Eur. J. Cancer., 45, 360 (2009).
Boden PR, Higginbottom M, Hill DR, Horwell DC, Hughes J, et al. (1993) "Cholecystokinin dipeptoid antagonists: design, synthesis, and anxiolytic profile of some novel CCK-A and CCK-B selective and 'mixed' CCK-A/CCK-B antagonists", J Med Chem 36: 552-565.
Boyce M, Warrington S, Black J (2013) "Netazepide, a gastrin/CCK2 receptor antagonist, causes dose-dependent, persistent inhibition of the responses to pentagastrin in healthy subjects", Br J Clin Pharmacol 76: 689-698.
Dunlop J, Brammer N, Ennis C (1996) "Pharmacological characterization of a Chinese hamster ovary cell line transfected with the human CCK-B receptor gene", Neuropeptides 30: 359-363.

Fossmark R, Sordal O, Jianu CS, Qvigstad G, Nordrum IS, et al. (2012) "Treatment of gastric carcinoids type 1 with the gastrin receptor antagonist netazepide (YF476) results in regression of tumours and normalisation of serum chromogranin A", Aliment Pharmacol Ther, 36: 1067-1075.
Hagishita S, Murakami Y, Seno K, Kamata S, Haga N, et al. (1997) "Synthesis and pharmacological properties of ureidomethylcarbamoylphenylketone derivatives. A new potent and subtype-selective nonpeptide CCK-B/gastrin receptor antagonist, S-0509", Bioorg Med Chem 5: 1695-1714.
Harper EA, Shankley NP, Black JW (1999) "Characterization of the binding of a novel radioligand to CCKB/gastrin receptors in membranes from rat cerebral cortex", Br J Pharmacol 126: 1504-1512.
Henke BR, Aquino CJ, Birkemo LS, Croom DK, Dougherty RW, Jr., et al. (1997) "Optimization of 3-(1H-indazol-3-ylmethyl)-1,5-benzodiazepines as potent, orally active CCK-A agonists", J Med Chem 40: 2706-2725.
Kawasaki D, Emori Y, Eta R, Iino Y, Hamano H, et al. (2008) "Effect of Z-360, a novel orally active CCK-2/gastrin receptor antagonist on tumor growth in human pancreatic adenocarcinoma cell lines in vivo and mode of action determinations in vitro", Cancer Chemother Pharmacol 61: 883-892. Epub Sep. 2007 2028.
Kuwahara T, Kudoh T, Nagase H, Takamiya M, Nakano A, et al. (1992) "Tetronothiodin, a novel CCKB receptor ligand, antagonizes cholecystokinin-induced Ca2+ mobilization in a pituitary cell line", Eur J Pharmacol 221: 99-105.
Lee YM, Beinborn M, McBride EW, Lu M, Kolakowski LF, Jr., et al. (1993) "The human brain cholecystokinin-B/gastrin receptor. Cloning and characterization", J Biol Chem 268: 8164-8169.
Makovec F, Revel L, Letari O, Mennuni L, Impicciatore M (1999) "Characterization of antisecretory and antiulcer activity of CR 2945, a new potent and selective gastrin/CCK(B) receptor antagonist", Eur J Pharmacol 369: 81-90.
Meyer T, Caplin ME, Palmer DH, Valle JW, Larvin M, et al. (2010) "A phase Ib/IIa trial to evaluate the CCK2 receptor antagonist Z-360 in combination with gemcitabine in patients with advanced pancreatic cancer", Eur J Cancer 46: 526-533.
Morton MF, Barrett TD, Freedman J, Li L, Rizzolio MC, et al. (2011) "JNJ-26070109 [(R)4-bromo-N-[1-(2,4-difluoro-phenyl)-ethyl]-2-(quinoxaline-5-sulfonylamino)-ben zamide]: a novel, potent, and selective cholecystokinin 2 receptor antagonist with good oral bioavailability", J Pharmacol Exp Ther 338: 328-336.
Nilsson I, Monstein HJ, Lindstrom E, Hakanson R, Svensson S (2002) "Pharmacological analysis of CCK(2) receptor ligands using COS-7 and SK-N-MC cells, expressing the human CCK(2) receptor", Regul Pept 103: 29-37.
Revel L, Ferrari F, Makovec F, Rovati LC, Impicciatore M (1992) "Characterization of antigastrin activity in vivo of CR 2194, a new R-4-benzamido-5-oxo-pentanoic acid derivative", Eur J Pharmacol 216: 217-224.
Roberts K, Ursini A, Barnaby R, Cassara PG, Corsi M, et al. (2011) "Synthesis and structure-activity relationship of new 1,5-dialkyl-1,5-benzodiazepines as cholecystokinin-2 receptor antagonists", Bioorg Med Chem 19: 4257-4273.
Singh L, Field MJ, Hill DR, Horwell DC, McKnight AT, et al. (1995) "Peptoid CCK receptor antagonists: pharmacological evaluation of CCKA, CCKB and mixed CCKA/B receptor antagonists", Eur J Pharmacol 286: 185-191.
Trivedi BK, Padia JK, Holmes A, Rose S, Wright DS, et al. (1998) "Second generation "peptoid" CCK-B receptor antagonists: identification and development of N-(adamantyloxycarbonyl)-alpha-methyl-(R)-tryptophan derivative (CI-1015) with an improved pharmacokinetic profile", J Med Chem 41: 38-45.
Boyce, M. et al. (Jul. 2012) "Single oral doses of netazepide (YF476), a gastrin receptor antagonist, cause dose-dependent, sustained increases in gastric pH compared with placebo and ranitidine in healthy subjects" Aliment Pharmacol Ther, 36(2):181-189.
Marova, E.I. (May 3, 2001) "Osteoporoz: klinika, diagnotika, lechenie (Osteoporosis: Clinical Practice, Diagnosis, Treatment)" RMJ, 92374-379 [online]. Retrieved from: http://nature.web.ru:8003/db/msg.html?mid-1165465&uri=index.html; retrieved on Mar. 12, 2019. Russian With English translation, 11 total pages.

(56) References Cited

OTHER PUBLICATIONS

Håkanson, R. et al. (1999) "CCK2 receptor antagonists: pharmacological tools to study the gastrin-ECL call-parietal cell axis" *Regulatory Peptides*, 80:1-12.
Yang, Yu-Xiao; Lewis, James D.; Epstein, Solomon; Metz, David C., Long-term Proton Pump Inhibitor Therapy and Risk of Hip Fracture, Journal of the American Medical Association, Dec. 27, 2006, vol. 296, No. 24, p. 2947-2954.†
Ito, T.; Jensen, R.T.,Association of Long-Term Proton Pump Inhibitor Therapy with Bone Fractures and Effects on Absorption of Calcium, Vitamin B12, Iron and Magnesium, Curr Gastroenterol Rep (2010) 12:448-457.†
Yang, Yu-Xiao, Proton Pump Inhibitor Therapy and Osteoporosis, Current Drug Safety, 2008, 3, 204-209.†
Berna, Mark J.; Jensen, Robert T., Role of CCK/gastrin receptors in gastrointestinal/metabolic diseases and results of human studies using gastrin/CCK receptor agonists/antagonists in these diseases, Curr Top Med Chem. 2007; 7(12):1211-1231.†
Fossmark, R.; Sordal, O; Jlanu, C.S.; Qvigstad, G.; Nordrum, I.S.; Boyce, M; Waldun, H.L, Treatment of gastric carcinoid type 1 with the gastrin receptor antagonist netazepide (YF476) results in regression oftumors and normalisation of serum chromogranin A, Published online Oct. 16, 2012†
Boyce, M.; Warrington, S.; Black, J., Netazepide, a gastrin/CCK2 receptor antagonist, causes dose-dependent, persistent inhibition of the responses to pentagastrin in healthy subjects, Br J Clin Pharmacol, 76:5, 689-698.†

\* cited by examiner
† cited by third party

| | Gastrin | PTH | Estradiol | Bone δ | Osteo | PTH1R | ERα | CaSR |
|---|---|---|---|---|---|---|---|---|
| CONTROL | ↕ | ↕ | ↕ | ↕ | ↕ | ↕ | ↕ | ↕ |
| 8 WK | ↑ | ↑ | ↓↓ | ↓↓ | ↓↓ | ↓ | → | ↕ |
| 16 WK | ↑↑ | ↓↓ | → | → | ↓ | ↓↓ | ↓↓ | ↓↓ |

Figure 23

SEQUENCE LISTING

```
<160> NUMBER OF SEQ ID NOS: 2

<210> SEQ ID NO 1
<211> LENGTH: 205
<212> TYPE: DNA
<213> ORGANISM: Homo sapiens

<400> SEQUENCE: 1
tttcctacct catgggtagg tgagacaaac actatctcca ccgttgccct ctctcttctt      60 aaagtcctt  acaaataacct gggttttcc tgatagggt ggaggaaatc atcctggtga     120
gcatgcagag ggcgcgtttc caagataacc cttcccttta cccttttttta ggggtatcag    180 tgagtgtatc cgctctaaat ctcgt                                          205

<210> SEQ ID NO 2
<211> LENGTH: 206
<212> TYPE: DNA
<213> ORGANISM: Homo sapiens

<400> SEQUENCE: 2
tttcctacct catgggtagg tgagacaaac actatctccc cctttaccct ctcccttctt      60
aaagcccttg acaaatacaa gggttttcc tgagaggagt ggaggaaatc atcctggtga     120
gcatgcagag ggcgttgttt ccaagatgac cctttcctt acccttgttt aggggtatca    180
gtgagtgtat ccactctaaa tctcgt                                         206
```

GASTRIN ANTAGONISTS FOR TREATMENT AND PREVENTION OF OSTEOPOROSIS

RELATED APPLICATIONS

This application claims the benefit of, and priority to, U.S. Provisional Application No. 61/907,980 filed Nov. 22, 2013, the content of which is incorporated herein by reference in its entirety.

INCORPORATION-BY-REFERENCE OF SEQUENCE LISTING

The contents of the text file named "CLIF-002-001_SequenceListing_ST25.txt", which was created on Jan. 27, 2015 and is 1.04 KB in size, are hereby incorporated by reference in their entireties.

TECHNICAL FIELD

The provided embodiments are based in some aspects on the demonstration herein of a role for gastrin in regulating the aging gut-ovary axis and effects of targeting gastrin activity in reversing gastrin-mediated bone loss. Provided are methods, compositions, and agents, including gastrin antagonists, for treatment, stabilization, amelioration, and prevention of bone diseases and conditions.

BACKGROUND

Osteoporosis, characterized by bone loss and high risk of fractures, is one of the commonest diseases particularly in old age, and is estimated to affect approximately 100 million people worldwide. While the incidence of bone fracture in the elderly is generally increasing, therapeutic choices are limited. Currently, antiresorptives (e.g. bisphosphonates, denosumab, hormone therapy) are the most commonly used treatments for osteoporosis. These agents are designed to slow bone remodeling and increase bone density. However, they have been associated with significant side effects including osteonecrosis of the jaw, atypical fractures, atrial fibrillation, and increased risk of stroke or cancer. Anabolic agents may be used to generate new bone in patients with osteoporosis. However, finding anabolic factors that increase bone mass and regulate the balance between osteoblast-mediated bone formation and bone marrow adiposity has been challenging. In addition, the only commercially available anabolic agent (teriparatide) is not only very expensive and difficult to administer but is also associated with side effects including lowered blood pressure, nausea, pain, weakness, and depression. Moreover, the use of teriparatide in rats has been found to cause malignant tumor growth (osteogenic carcinoma). In general, therapeutic choices for osteoporosis are limited and the development of new therapeutic approaches that stimulate bone formation is a priority.

Although ovarian failure and bone demineralization are well recognized as key elements in osteoporosis, the precise etiology remains incompletely resolved. A better understanding of the etiology of osteoporosis and related bone diseases or conditions may lead to novel alternative methods and compositions for the treatment of osteoporosis and other bone diseases and conditions.

There is a need for methods and compositions for the treatment of osteoporosis and other bone diseases and conditions. The present application overcomes the above-noted problems and provides a novel means for the treatment, stabilization, and/or prevention of the progression of a bone disease or condition by regulating the effects of gastrin.

SUMMARY

The present application provides methods, uses, compounds, and compositions for treatment, e.g., stabilization, and/or prevention, e.g., prevention of the progression of a bone disease or disorder through the administration of an agent to a subject in need thereof. In some embodiments, the bone disease or disorder is characterized by osteoporosis. In other embodiments, agent administered to the subject in need thereof targets, e.g., inhibits or antagonizes, gastrin and/or gastrin receptors, such as gastrin or gastrin receptor antagonists. According to one embodiment, the administered agent targets the CCK2 receptor.

The provided embodiments relate in some aspects to the demonstration herein that the hormone gastrin directly or indirectly regulates bone formation, thus promoting bone loss with a consequent bone pathophysiology consistent with osteoporotic alterations (see FIG. 57). The provided embodiments relate in some aspects to the demonstration herein that blockade of such gastrin effects, for example, using a gastrin antagonist that targets the CCK2 receptor, has a beneficial effect in animal models of osteoporosis and thus is useful in the treatment, prevention, and amelioration of osteoporosis and other bone diseases and conditions.

Thus, provided in some embodiments are methods, compounds, compositions and uses of gastrin antagonists, e.g., agents that antagonize gastrin activity, in bone diseases and conditions, such as those clinically, pathologically or radiologically characterized as osteoporosis. In some aspects, the methods and uses involve treatment, amelioration, and/or prevention of diseases and conditions including diseases and conditions. In some aspects, provided are methods and compositions for treatment, amelioration diseases/conditions of the bone, e.g., those characterized as osteoporosis, using agents targeting gastrin and/or gastrin receptors, e.g., gastrin antagonists, for example, in i) older persons (male or female), e.g., geriatric patients; ii) females with decreased ovarian function or failure thereof, iii) individuals with hypergastrinemia, including those with natural hypergastrinemia (e.g., neoplastic or associated with gastric mucosal atrophy) and/or hypergastrinemia occurring as a consequence of the use of acid suppressive pharmacotherapy (e.g., classes of agents including all proton pump inhibitors or all short or long acting histamine two receptor antagonists) and/or iv) individuals with gastric resection. In some embodiments, the treatment, amelioration, and/or prevention is carried out using a gastrin-targeting agent, e.g., a gastrin antagonist, such as a gastrin-targeting or gastrin receptor-targeting agent, e.g., gastrin or gastrin receptor antagonist, for example, an agent that targets the CCK2 receptor.

In some embodiments, provided are methods, uses, and agents for treating or preventing a bone disease or condition in a subject by administering to the subject a gastrin or gastrin receptor-targeting agent, thereby treating or preventing the disease or condition or progression thereof. In some aspects, the gastrin or gastrin receptor-targeting agent is a gastrin antagonist or gastrin receptor antagonist, such as a selective gastrin receptor antagonist, such as a selective CCK2 receptor antagonist, e.g., one that does not antagonize other receptors or other gastrin receptors. Exemplary of the selective CCK2 receptor antagonist is YF476.

In some aspects, the bone disease or condition is a disease or condition characterized as osteoporosis, for example, one that has been characterized as osteoporosis clinically, pathologically, or radiologically. In some aspects, the subject is a female with decreased ovarian function or ovarian failure. In other aspects, the subject: (a) is a female with decreased ovarian function or ovarian failure, and (b) has hypergastrinemia. In some aspects, the subject: (a) is a female with decreased ovarian function or ovarian failure, (b) has hypergastrinemia, (c) has experienced gastric resection. In some aspects, the subject has natural hypergastrinemia, such hypergastrinemia that is neoplastic hypergastrinemia or hypergastrinemia associated with acid suppressive pharmacology, such as administration with a proton pump inhibitor or histamine 2 receptor antagonist. In some aspects, the method further comprises administering to the subject a proton pump inhibitor or histamine 2 receptor antagonist, simultaneously or sequentially, in any order, with the gastrin or gastrin receptor-targeting agent. In some aspects, the method further comprises administering another osteoporosis treatment simultaneously with or sequentially, in any order, to the agent.

In some embodiments, a method for treating a bone disease or condition associated with hypergastrinemia in a subject in need thereof comprises administering to the subject at least one dose of a therapeutically effective amount of a gastrin receptor-targeting agent, thereby treating the bone disease or condition associated with hypergastrinemia.

In other embodiments, the methods further include administering doses of the gastrin-receptor targeting agent intravenously.

In additional embodiments, the methods further include administering doses of the gastrin-receptor targeting agent orally.

In some embodiments, the methods further include a disease or condition characterized as osteoporosis.

In other embodiments, the methods further include administering a selective CCK2 receptor antagonist.

In additional embodiments, the methods further include administering selective CCK2 receptor antagonist YF476.

In some embodiments, the methods further include a subject that is a female with decreased ovarian function or ovarian failure. In other embodiments, the methods further include a subject that is: (a) is a female with decreased ovarian function or ovarian failure and (b) has hypergastrinemia. In some embodiments, the methods further include a subject that is: (a) is a female with decreased ovarian function or ovarian failure, (b) has hypergastrinemia, (c) has experienced gastric resection.

In yet another embodiment, the hypergastrinemia is neoplastic hypergastrinemia or hypergastrinemia associated with acid suppressive pharmacology.

In other embodiments, the methods further include administering the selective gastrin receptor-targeting agent with a therapeutically effective amount of a proton pump inhibitor (PPI) or histamine 2 receptor ($H_2R$) antagonist, simultaneously or sequentially, in any order.

In yet another embodiment, the methods further include wherein the PPI is omeprazole and the $H_2R$ antagonist is loxtidine.

In other embodiments, the methods further include administering a therapeutically effective amount of the gastrin receptor-targeting agent at 0.2-14 µg/kg body weight of the subject.

In additional embodiments, the therapeutically effective amount of the gastrin receptor-targeting agent is 10-25 nanomolar.

In some embodiments, the gastrin receptor-targeting agent is administered to the subject by subcutaneous injection.

In additional embodiments, the gastrin receptor-targeting agent is administered to the subject by intravenous injection.

In some embodiments, the gastrin receptor-targeting agent is orally administered to the subject as a daily tablet dose at 20-100 mg doses.

Also provided are agents and compositions, e.g., pharmaceutical compositions, and kits for use in the provided methods, such as agents and compositions comprising the gastrin and gastrin receptor targeting agents, e.g., antagonists, and kits containing the same with instructions for administration to such subjects.

BRIEF DESCRIPTION OF THE DRAWINGS

FIG. 23 is a chart summarizing Gastrin-mediated alterations in the Mastomys model. In comparison to control (untreated, normo-gastrinemic animals), short-term-loxtidine treatment elevated circulating gastrin and PTH but decreased estradiol. This was associated with a decreased bone density and osteoporotic phenotype. In the stomach expression of PTH1R was upregulated while ERα was decreased. No changes were detectable in the calcium sensing receptor (CaSR). In comparison to control, long-term-loxtidine treatment elevated circulating gastrin but decreased both PTH as well as estradiol. This was associated with a decreased bone density and osteoporotic phenotype. In the stomach expression of PTH1R, ERα and CaSR was upregulated consistent with activation of a calcium metabolic phenotype. 8 wk=8 week loxtidine treatment, 16 wk=16 week loxtidine treatment, Bone d=bone density measurements, Osteo=osteoporotic phenotype.

DETAILED DESCRIPTION

Figure 57:
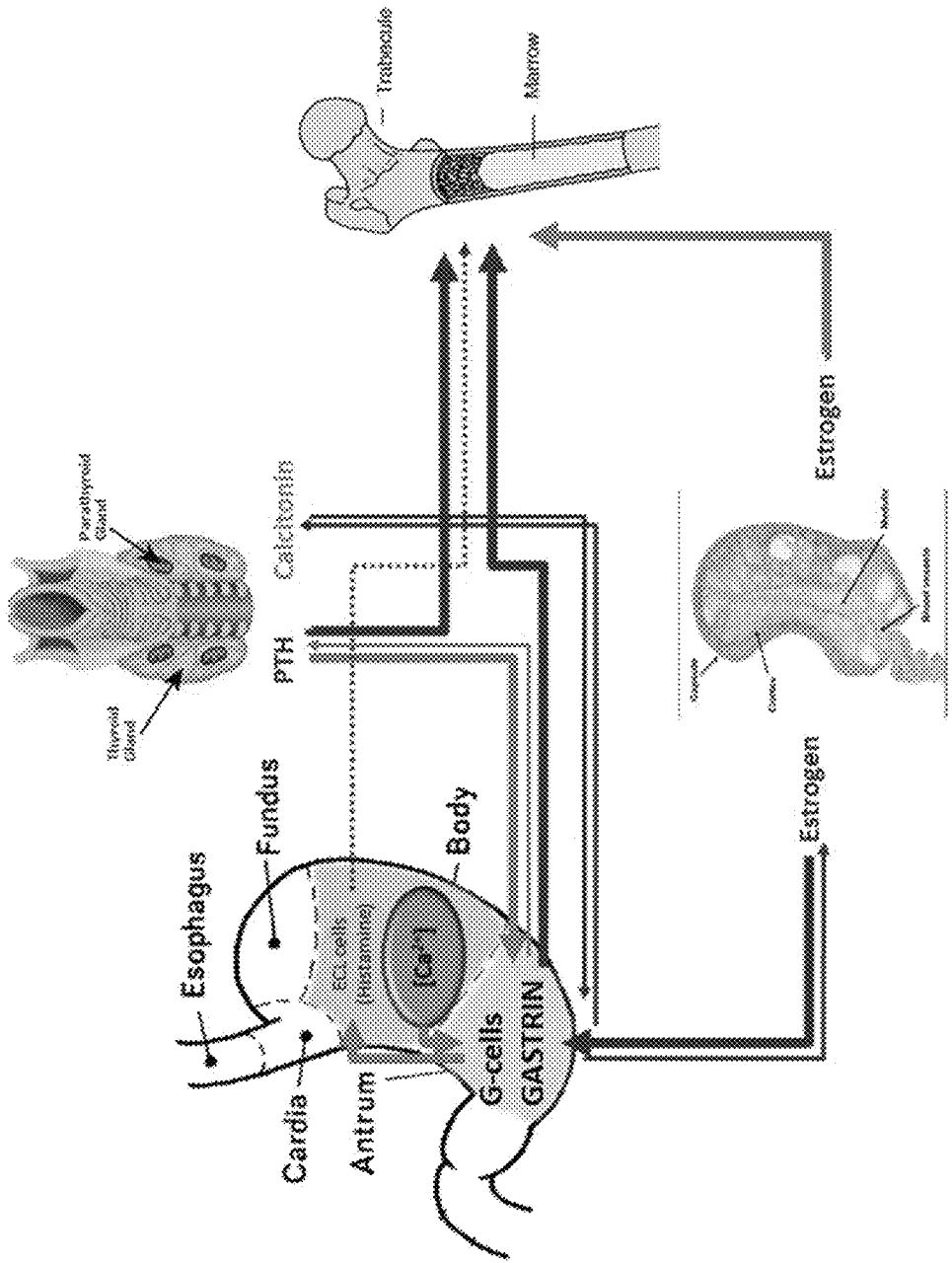
FIG. 57 shows an integrated model for the regulation of bone remodeling based on the results demonstrated herein. The effects of ovarian function (and the secretion of estrogen) and parathyroid gland PTH secretion are shown herein to be modulated by the antral gastrin-secreting G-cell. As the principal calcium sensing cell in the stomach and a nexus for both PTH and estrogen signaling within the stomach, gastrin through its negative effect on bone remodeling (osteoclast activation) is a central regulator for the bone phenotype. These roles may be modified by calcitonin and the thyroid and amplified by histamine release from ECL cells. Darker grey lines=stimulatory, lighter grey lines=inhibitory effects.

According to one embodiment, the present application provides a novel means for the treatment, stabilization, and/or prevention of the progression of a bone disease or condition. This novel means is supported by the finding that the hormone gastrin either directly or indirectly regulates bone formation, thus promoting bone loss with a consequent bone pathophysiology consistent with osteoporotic alterations (see FIG. 57).

In accordance with one aspect of the present application, it has been found that blockade of these gastrin effects, using a gastrin antagonist that targets the CCK2 receptor, has a beneficial effect in animal models exhibiting a bone disease or condition characterized by osteoporosis.

Figure 58:
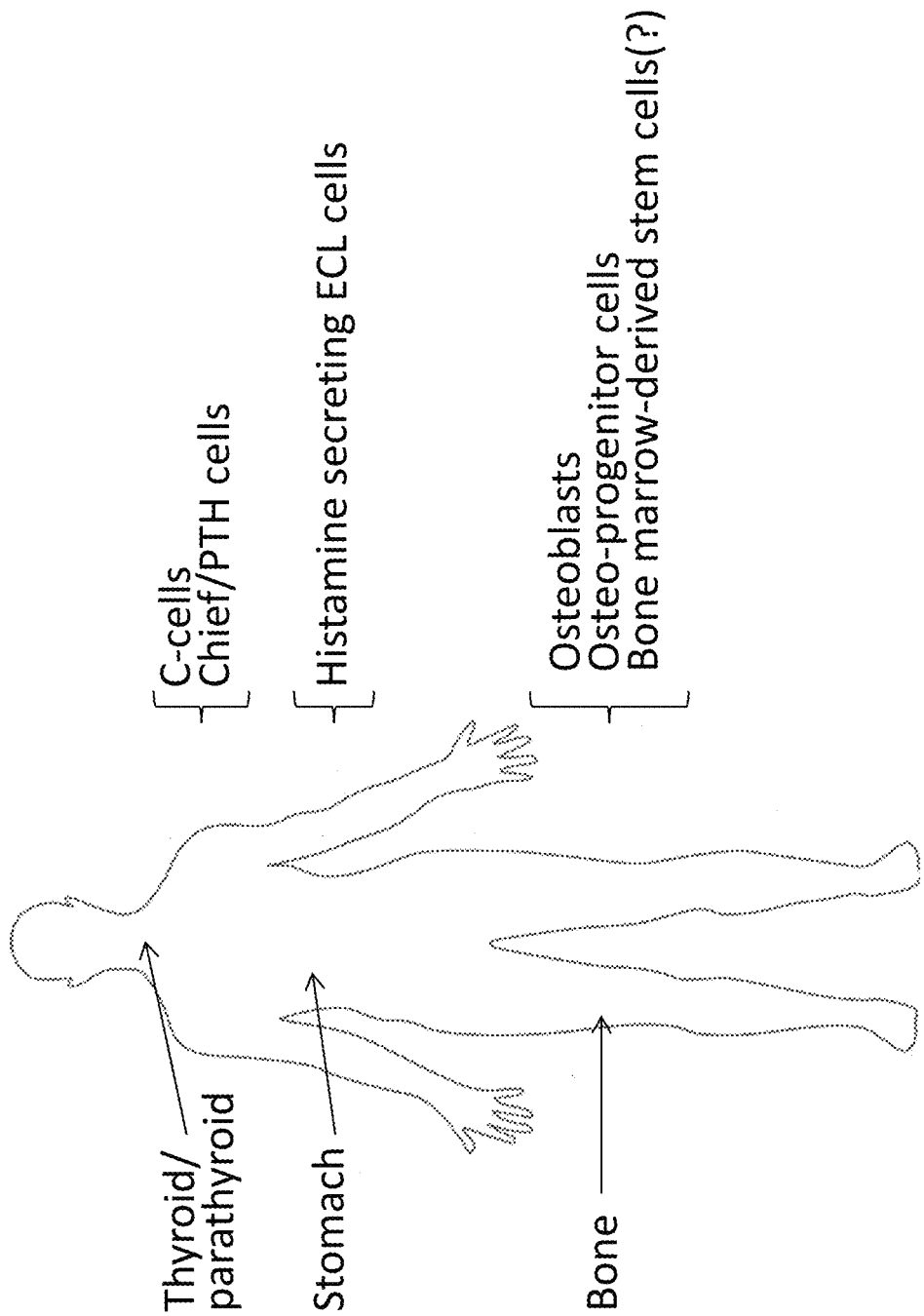
FIG. 58 is a diagram showing the distribution of gastrin/CCK2 receptor targets in the body. The receptor is expressed in the thyroid gland (including parathyroids), within the stomach as well as in the bone. In the thyroid glands, CCK2 is expressed on both calcitonin-secreting C cells as well as on PTH secreting cells in the parathyroids. In the gut, CCK2 is expressed in histamine secreting ECL cells while in the bone, receptor expression may be present on multiple cells including osteoblasts and osteo-progenitor cells. Targeting the gastrin/CCK2 receptor with specific antagonists will inhibit bone diseases, e.g., osteoporosis either directly (bone) or indirectly via the stomach and thyroid/parathyroid axis. PTH=parathyroid.

Accordingly, the present application relates to the use of gastrin-targeting agents, such as gastrin antagonists, or agents that antagonize gastrin activity, to treat bone diseases or conditions (see FIG. 58).

A. Definitions

The term "condition" as used herein refers generally to a disease, event, or change in health status.

The term "bone disease or condition" as used herein refers to a disease or condition associated with abnormality of the bone that can be treated by increasing bone mass and/or bone growth. For instance, the bone disease or condition may include: primary osteoporosis; secondary osteoporosis; osteogenesis imperfecta; osteodystrophy; osteopenia; Paget's disease; osteolytic lesions produced by bone metastasis, radiotherapy, or chemotherapy; periodontal disease; alveolar bone loss; bone loss due to immobilization or sex hormone deficiency; bone loss due to metastatic cancer; bone and cartilage loss caused by an inflammatory disease; osteoarthritis; osteotomy bone loss; childhood idiopathic bone loss; curvature of the spine; and bone fractures. The bone disease or condition may be a bone disease or condition associated with hypergastrinemia. The bone disease or condition may also be exhibited by subjects with specific circumstances, as described in the paragraph below.

The term "subject" as used herein refers to a mammal, preferably a human. For instance, these subject may include subjects who are i) older persons (male or female); ii) females with decreased ovarian function or failure thereof, iii) any individuals with hypergastrinemia—either natural (neoplastic or associated with gastric mucosal atrophy) or iv) as a consequence of the use of acid suppressive pharmacotherapy (classes of agents including all proton pump inhibitors or all short or long acting histamine two receptor antagonists) or v) individuals with gastric resection. In all such cases, the bone disease or condition may be ameliorated in these subjects by the use of a class of gastrin-targeting agent. For example, the class of gastrin-targeting agent is a gastrin antagonist targeting the CCK2 receptor.

The term "gastrin-targeting agent" as used herein means a gastrin antagonist, such as a gastrin-targeting or a gastrin receptor-targeting agent, as well as a gastrin or gastrin receptor antagonist, for example, an agent that targets the CCK2 receptor.

The term "therapeutically effective amount" as used herein means the amount of the gastrin-targeting agent as described in the present application that will achieve the goal of treating, ameliorating the effects of, or preventing the bone disease or condition, or will improve the disease or condition severity and the frequency of incidence. The improvement in bone disease or condition severity includes the reversal of the disease or condition, as well as slowing down the progression of the disease or condition.

The term "treat" or "treatment" as used herein means lessening, inducing stasis of, or postponing or reducing the progression, development, onset, or severity of the disease or condition or of one or more symptoms associated with a disease or disorder or condition described herein, or ameliorating existing uncontrolled or unwanted symptoms, preventing additional symptoms, or ameliorating or preventing the underlying metabolic causes of symptoms. Thus, the terms denote that a beneficial result has been conferred on a subject with a disease or symptom, or with the potential to develop such disease or symptom. A response is achieved when the subject experiences partial or total alleviation, or reduction of one or more signs or symptoms of disease, condition, or illness, such as, but not limited to, reversal or prevention of bone loss, reversal or prevention of loss of bone mass, reversal or prevention of bone fracture or risk thereof, increase or prevention of decrease in bone density, increase in boner remodeling, reduction of bone resorption, and/or bone regeneration.

It will be understood that use the term "about" herein in reference to a recited numerical value includes the recited numerical value and numerical values within plus or minus ten percent of the recited value.

It will be understood that use of the term "between" herein when referring to a range of numerical values encompasses the numerical values at each endpoint of the range. For example, a nucleic acid sequence of between 10 base pairs and 20 base pairs in length is inclusive of a nucleic acid sequence of 10 base pairs in length and a nucleic acid sequence of 20 base pairs in length.

B. Role for G Cells and Gastrin in Calcium Sensing and Bone Disease

Figure 1:
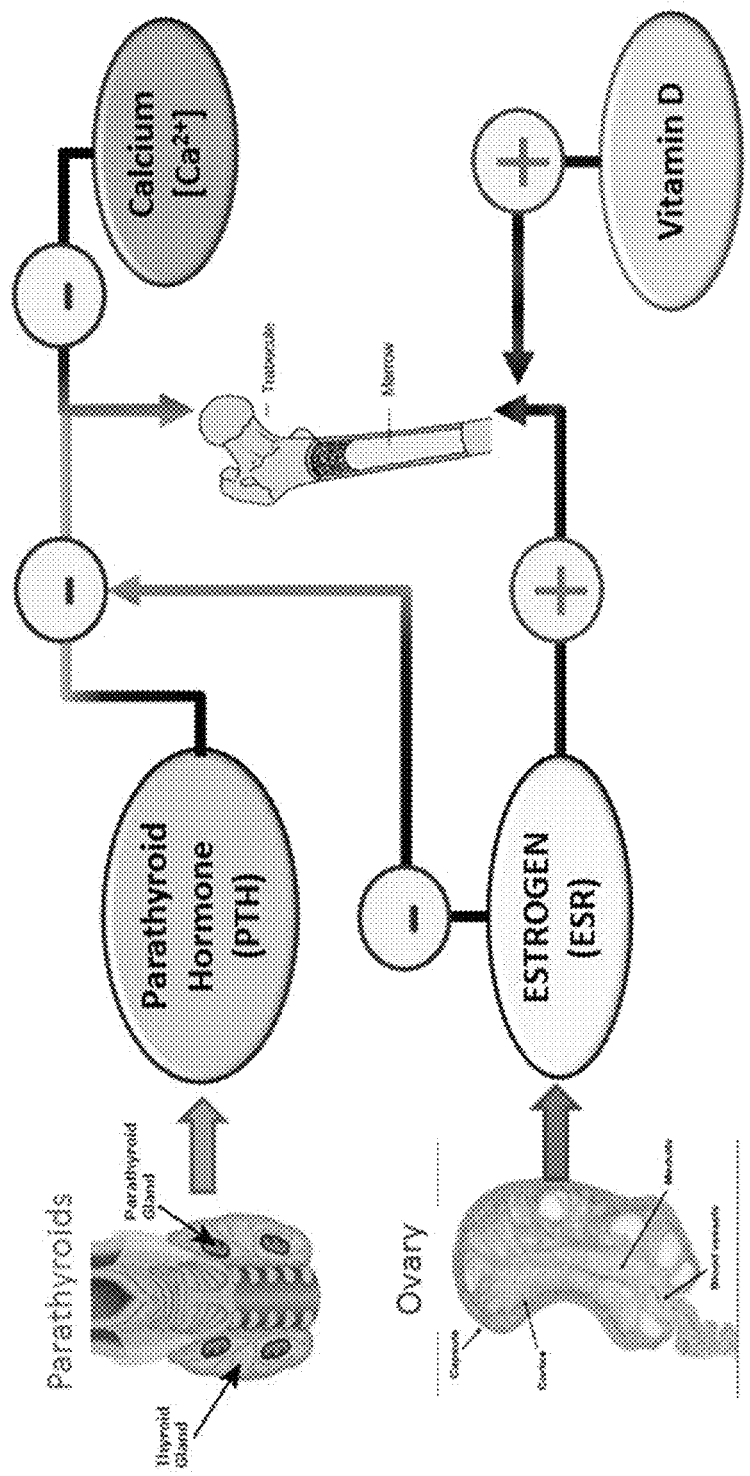
FIG. 1 is a diagram showing regulators of bone remodeling. Ovarian function (and the secretion of estrogen) is positively associated with bone maintenance. Vitamin D is thought to supplement this, but while low vitamin D is associated with osteoporosis, this may be an epiphenomenon as vitamin D receptor mutations are not associated with increased fracture risk. Parathyroid produced PTH negatively regulates bone physiology, an effect amplified by low levels of circulating calcium. Estrogen antagonizes the negative effect of PTH. The role for gastric hormones has not been clear, but removal of the stomach is known to increase bone loss. This is thought to reflect loss of acid and the resultant decrease in calcium uptake.

Osteoporosis, characterized by bone loss and high risk of fractures, is one of the most common diseases, particularly in old age, and is estimated to affect approximately 100 million people worldwide. Although ovarian failure and bone demineralization are well recognized as key elements in this disease, the precise etiology remains incompletely resolved. With reference to FIG. 1, the known hormonal and mineral regulators of bone remodeling are shown.

Under normal circumstances, bone remodeling occurs as physiological or mechanical responses to maintain strength and mineral homeostasis (particularly calcium). These involve inter-related phenomena of formation and resorption affected by osteoblast and osteoclast activity. Typically, this involves four steps including osteoclast precursor activation, active resorption, reversal of resorption and new bone formation. The first two steps take 2-4 weeks, the last step takes 4-6 months to complete.

Bone remodeling increases in peri-menopausal and early postmenopausal women and then slows with further aging, but continues at a faster rate than in premenopausal women. Bone remodeling is also thought to be increased in aging men.

Figure 2:
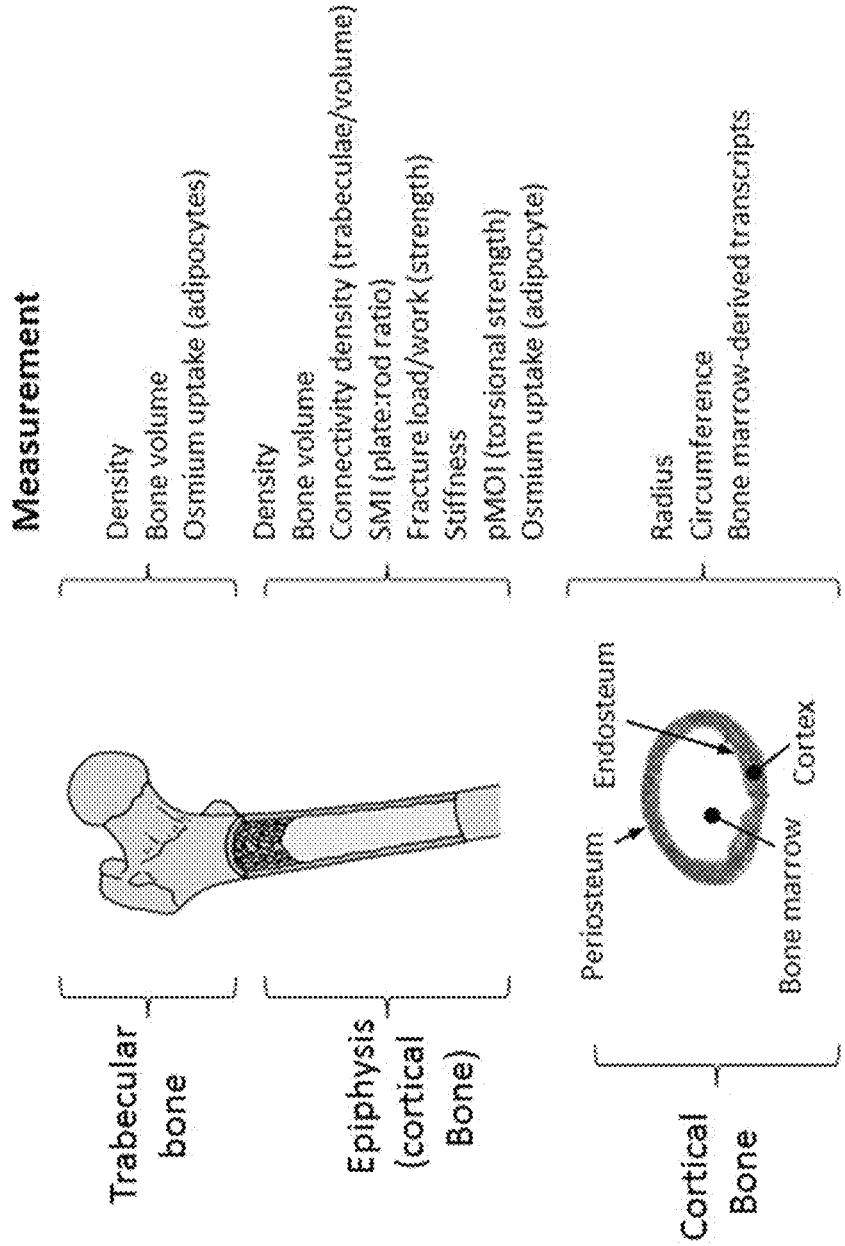
FIG. 2 is an illustration showing bone physiology and structural and strength measurements. Microcomputed tomography (MicroCT) and bone bending as well as osmium uptake and PCR were used to evaluate bone dynamics and osteoporotic features in the different animal models. MicroCT assesses density and volume of both the trabecular and cortical bones. Measurements of the radius and circumference of the cortical bone can be undertaken. Calculations of the connectivity density, the structural model index (SMI) as well as the stiffness (all measures of structure) of the bone can be made. The polar moment of inertia (pMOI) as well as fracture and workloads identify the underlying bone strength. Osmium uptake identifies alterations in adipogenic phenotypes while PCR can assess activation of transcripts involved in osteo-activation.

With reference to FIG. 2, cortical bone is dense and solid and surrounds the marrow space. It has an outer periosteal surface and inner endosteal surface. It is typically less metabolically active than trabecular bone. Periosteal surface activity is important for appositional growth and fracture repair. The endosteal surface has a higher remodeling activity than the periosteal surface, likely the result of greater biomechanical strain or greater exposure to signaling from the adjacent bone marrow compartment.

Increased cortical remodeling causes an increase in cortical porosity and decrease in cortical bone mass. Bone resorption typically exceeds bone formation on the endosteal surface while bone formation typically exceeds bone resorption on the periosteal surface.

Trabecular bone is composed of a honeycomb-like network of trabecular plates and rods interspersed in the bone marrow compartment. It is more metabolically active than cortical bone. Turnover in this bone type appears most important for mineral metabolism and the maintenance of mechanical strength.

The biology of bone remodeling is complex and involves a range of activating factors e.g., PTH, estrogen, growth factors and inflammatory cytokines as well as dietary intake e.g., calcium and vitamin D. This has led to the development of a wide spectrum of therapies that are now available for management. These include hormone replacement therapy, bisphosphonates, diets high in calcium and vitamin D, to the use of statins, fibroblast growth factor-1, or parathyroid hormone (PTH) itself.

PTH is considered the pivotal regulator of bone metabolism since it enhances the release of $Ca^{2+}$ from the bone reservoir through process of resorption. The effect of PTH is, however, indirect since osteoclasts do not have a PTH receptor. PTH instead binds to osteoblasts and results in expression of RANKL. RANKL activates osteoclast precursor cells via the receptor RANK, to fuse, forming new osteoclasts which are responsible for bone resorption.

Evidence supporting a role for PTH in osteoporosis comes from several studies reporting that PTH values are higher in the elderly than in young adults. A number of factors have been proposed to contribute to the higher PTH values including decreased renal function, less efficient intestinal absorption of calcium ($Ca^{2+}$) perhaps due to a loss of motivation to eat, resistance to the calcemic action of PTH, a greater prevalence of vitamin D insufficiency and, more particularly, in the increased gastric pH noted in old age.

The latter reflects both loss of parietal cell mass (mucosal atrophy) with concomitant elevations in gastric pH as well as increased gastrin secretion from the antral neuroendocrine G cell.

Age-related alterations in gastric mucosal integrity and function are considered a major issue in gastroenterological complaints of the elderly as well as being responsible for an increased susceptibility to drugs, bleeding and failure to absorb $Ca^{2+}$ and iron adequately.

A $Ca^{2+}$/PTH/vitamin D axis is thought to maintain systemic $Ca^{2+}$ homeostasis by coordinating the functions of the parathyroid gland, kidney, bone and gastrointestinal tract to increase serum $Ca^{2+}$ without concomitant increases in serum phosphorus levels. This axis is primarily designed to protect against hypocalcemia by mobilizing $Ca^{2+}$ from the skeleton, conserving $Ca^{2+}$ by the kidneys and increasing gastrointestinal $Ca^{2+}$ absorption.

In response to a reduction in serum $Ca^{2+}$ concentration, the calcium sensing receptor (CaSR) in the parathyroid gland increases PTH secretion while the CasR in the kidney reduces renal $Ca^{2+}$ excretion. Calcium sensing is not, however, limited to the parathyroid glands and the CaSR is present in a variety of other cell types, including the antral gastrin-producing G cell. This neuroendocrine cell, given its gastric location is uniquely positioned to sense and respond to dietary $Ca^{2+}$ intake.

CaSR's detect changes in extracellular $Ca^{2+}$ concentration and initiate adaptive hormonal and ion-transport responses to maintain systemic calcium homeostasis. The parathyroid gland, thyroid C-cells and the kidney are currently considered to represent the physiologically relevant sites of CaSR expression. In general, low (<1 mM) circulating extracellular $Ca^{2+}$ is the major stimulus for PTH secretion from parathyroid cells. At higher concentrations, $Ca^{2+}$ inhibits PTH synthesis and secretion through CaSR phosphorylation and subsequent inactivation.

A CaSR has also been identified in ovine parafollicular C-cells and in the medullary thyroid carcinoma (MTC) cell line, TT. The latter responds to $Ca^{2+}$ with calcitonin secretion.

Although a CaSR has been identified in osteoblasts and osteoclasts, a physiological role for $Ca^{2+}$ sensing is unclear as these are expressed at very low levels in these cells. In contrast to bone cells, a physiologically relevant CaSR has been identified in the stomach. A CaSR has recently been cloned and sequenced from human antral G cells and functions at $Ca^{2+}$ concentrations >2 mM.

The following subsections (1-8) provide a brief overview and discussion of the studies demonstrated herein in the Examples. These subsections are provided to further illustrate the Examples and are not intended to limit the results and conclusions contained therein.

1. Isolated G Cell Studies

Figure 3:
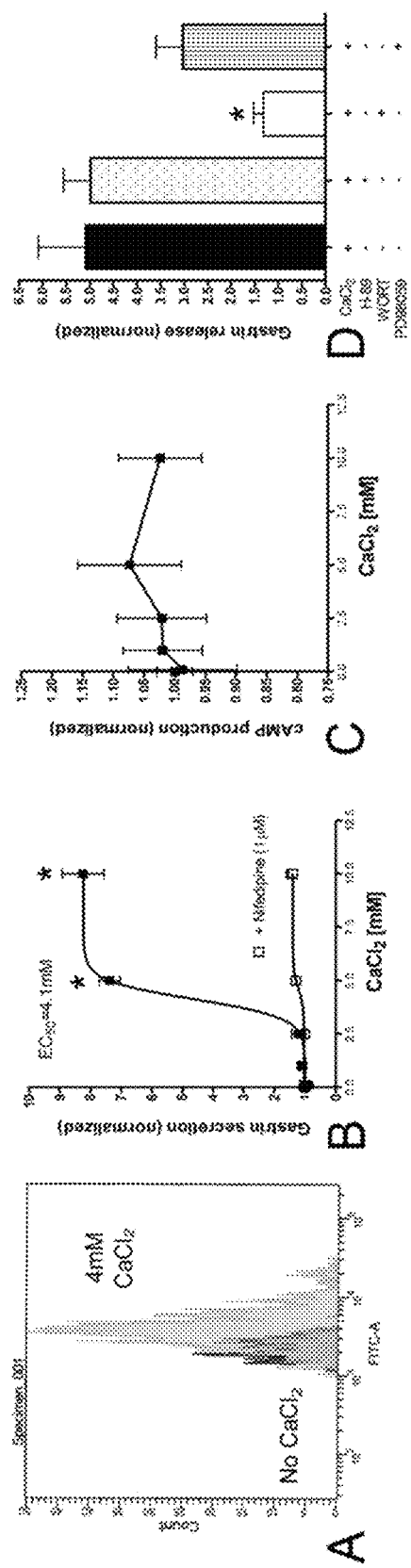
FIG. 3 is a series of graphs (3A-3D) demonstrating that G cells act as calcium sensors. $CaCl_2$ (4 mM) stimulated calcium influx (FITC shift: >5-fold rightwards—measured using flow cytometry) which was not observed in the absence of $CaCl_2$ (3A). $CaCl_2$ dose-dependently stimulated gastrin release ($EC_{50}$=4.1 mM, 8-fold) and was inhibited by preincubation (10 mins) with the calcium channel antagonist, nifedipine (1 µm) (3B). This calcium-mediated gastrin secretion was not associated with cAMP production (3C) and could not be inhibited by either the PKA inhibitor H-89 (10 µM) or the MAPK inhibitor PD98059 (0.1 µM), both associated with cAMP/MAPK-mediated gastrin secretion (3D). In contrast, wortmannin (1 nM), an inhibitor of PI3K signaling, significantly inhibited $CaCl_2$-mediated gastrin release. These results demonstrate that gastrin secretion is coupled to a calcium-channel regulated calcium-sensing mechanism that is transduced via $PI_3K$ signaling. Mean±SEM (n=4 experiments). *p<0.05 vs. unstimulated cells, WORT: Wortmannin.

Demonstrated herein is a physiological role for G cells as $Ca^{2+}$ sensors (see Example 1, FIG. 3). In general, calcium ingested during a meal (1-10 mM) stimulates gastrin release. Mechanistically, extracellular $Ca^{2+}$ is taken up by the gastric CaSR which activates gastrin release through calcium-induced pathways. The results demonstrated herein further identify the G cell as the pivotal neuroendocrine cell in the gut/parathyroid calcium homeostasis.

Figure 4:
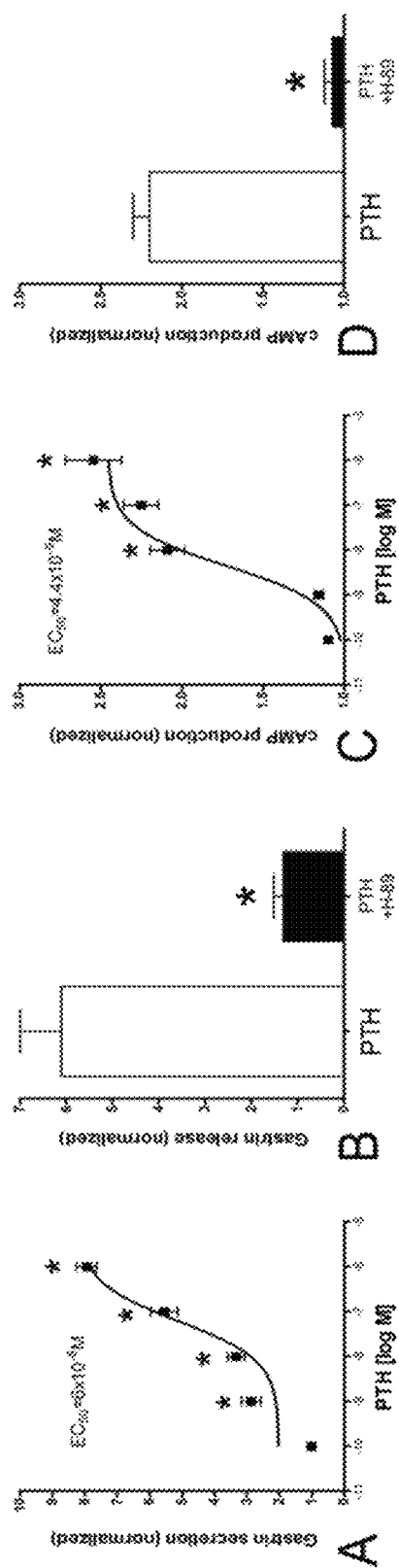
FIG. 4 is a series of graphs (4A-4D) demonstrating PTH stimulation of G cell function. PTH stimulated gastrin release ~8-fold with an estimated $EC_{50}$=60 nM (4A), an effect that could be inhibited by preincubation with the PKA inhibitor, H-89 (10 μM) for 10 mins (4B). PTH also dose dependently stimulated cAMP production ($E_{50}$=4 nM, 250%) (4C), a response that was reversed by H-89 (preincubation: 10 mins-10 μM) (4D). These results demonstrate that gastrin secretion is coupled to PTH receptor-mediated PKA activation and cAMP signaling. Mean±SEM (n=4 experiments). *p<0.05 vs. unstimulated cells or vs. PTH alone.

Investigations were performed to confirm the presence of a PTH receptor on the G-cell and PTH-mediated gastrin release following cAMP activation (see FIG. 4). These investigations are supported by other studies. For example, PTH infusion (40 units/20 min) increased gastrin levels in both antral and mixed venous blood without inducing systemic hypercalcemia in anesthetized pigs. Moreover, native bovine PTH and synthetic human 1-34 PTH (0.02-4 U/min) produced rapid (within 10-30 min) and pronounced (approximately 10-fold) increases in gastrin release in young, anesthetized pigs.

Figure 6:
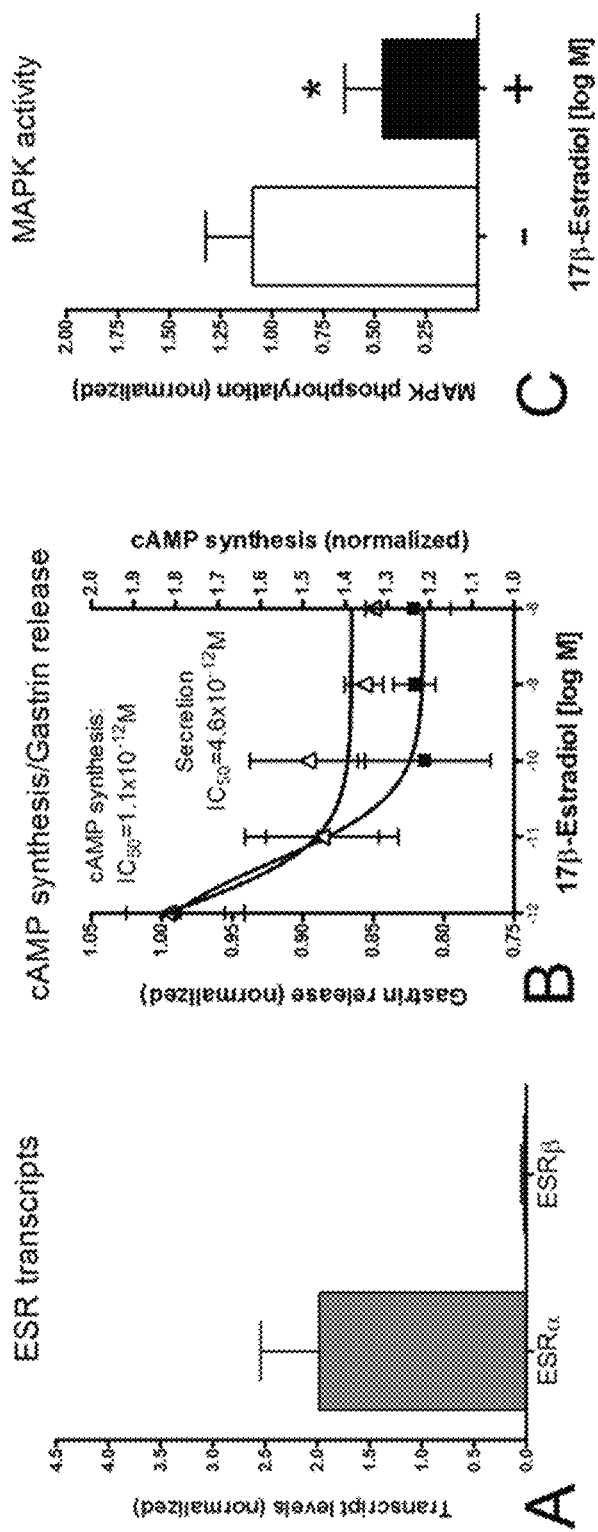
FIG. 6 is a series of graphs (6A-6C) demonstrating estrogen inhibition of G cell function. G cells express ESRα transcripts (6A) and 17β-estradiol inhibits both cAMP synthesis ($IC_{50}$=1.1×10$^{-12}$M, -15%) and gastrin release ($IC_{50}$=4.6×10$^{-12}$M, ~20%) (6B). In addition, preincubation with this ESRα agonist inhibited MAPK phosphorylation (75%, 6C). These results identify gastrin secretion is inhibited by estrogen receptor-α-mediated inhibition of PKA/cAMP production and MAPK signaling. Mean±SEM (n=4 experiments). *p<0.05 vs. 17β-estradiol (1 nM) alone.

Studies were also performed in isolated gastrin cells to show that 17β-estradiol (ESRα agonist) inhibited gastrin release (see FIG. 6). The non-genome targeting effects of estrogen have been well defined in other cell types such as breast tissue. These effects, ERα mediated MAPK signaling, are also demonstrable in the G cell, where estrogen is a potent inhibitor of gastrin secretion.

This information indicates that altering the estrogen milieu consistent with the menopausal state will profoundly alter/stimulate G cell function (signaling and secretion). This is consistent with previous reports in aged rats of the existence of a milieu that includes increased G cell function and a high PTH. This combination is well accepted as related to the development of osteoporosis.

Additional in vitro studies have identified that gastrin secretion may be modulated by the gut production of histamine and serotonin. The proposal of a role for histamine in modulation of the skeletal system is associated with equivocal information. Excess histamine release in mastocytosis and allergic diseases may lead to development of osteoporosis. In contrast, histamine can increase bone resorption both directly through osteoclast precursors and osteoclasts, and indirectly, by increasing the expression of RANKL (the osteoclast activating receptor) in osteoblasts. In addition, in vivo studies, H1 and H2 receptor antagonists can exert protective effects on the bone tissue, although this is not consistently reproduced in all experimental models. Nevertheless, histamine regulates gastrin release both ex vivo as well as in vitro.

The role of serotonin in bone metabolism has not been entirely clear. Injection of serotonin increases bone mineral density in rats via serotonin-mediated osteoblast proliferation (these cells express 5-HT$_2$ receptors). In an animal model, serotonin appeared to inhibit bone formation in an Lrp5-dependent manner. Lrp5 limits serotonin production through inhibition of the rate-limiting serotonin synthesis enzyme, tryptophan hydroxylase 1 (Tph1). In clinical studies, however, LRP5 mutations are associated with no change in circulating serotonin and patients exhibit high bone mass. Serotonin re-uptake inhibitors (SSRIs) have been associated with osteoblast proliferation but in middle-aged women, use of SSRIs was not associated with an increased rate of bone loss. In addition, high circulating serotonin in carcinoid syndrome was not associated with clinically significant lower bone density, poorer bone structure, or lower bone formation markers. Any effect of serotonin may alternatively be via the G cell; gastrin release is stimulated by 5-HT$_3$ receptors. The amine may therefore modulate bone formation through activity on the G cell.

When assessed collectively, data and observations presented herein, e.g., the existence of a luminal calcium sensing receptor, selective expression of receptors for parathyroid and thyroid functional regulation as well as vitamin D, and aminergic receptor expression (positively regulated by histamine and serotonin), identify the G cell as the pivotal neuroendocrine cell in the gut/parathyroid calcium homeostasis axis.

2. Gastrin Target Studies (In Vitro)

Studies demonstrated herein explore which cells may be potential gastrin targets. Additionally, these studies examined whether the gastrin cell could regulate the calcium homeostasis axis through gastrin release (see Example 2).

The presence of CCK$_2$ receptors in the PTH chief cells has not been clear, but has been suggested in a number of physiological studies. In isolated bovine parathyroid cells, gastrin at high concentrations (>1 μM) increased cAMP accumulation (40-60% in ~50% of experiments), a necessary prerequisite for PTH release.

Avian models have also supported this observation. Induction of hypergastrinemia (using the proton pump inhibitor (PPI), omeprazole (400 μM/kg/day) for 5 weeks) in chickens resulted in an increase in the size of the PTH gland as well as in PTH transcription. These effects were recapitulated by gastrin injection (continuous, 5 nmol/kg/hour, for 3 weeks).

Figure 8:
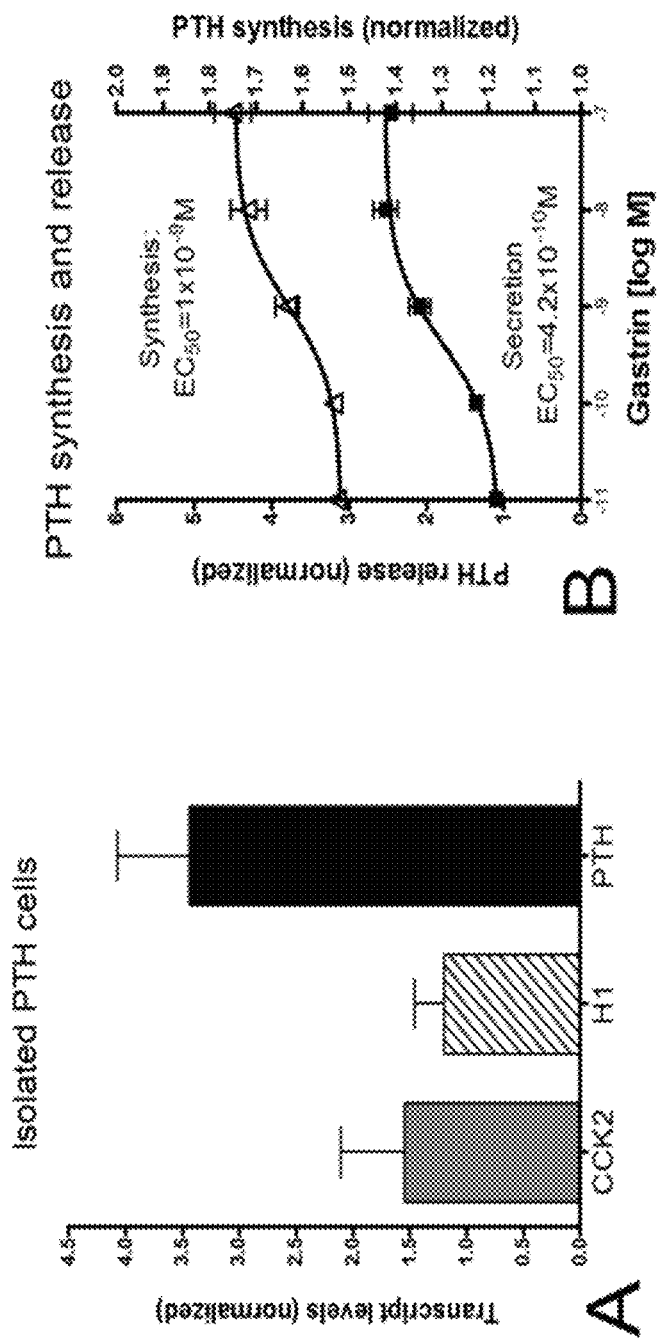
FIG. 8 is two graphs (8A-8B) showing gastrin stimulation of human PTH secretion. Receptors for gastrin (CCK2) and histamine (H1) are expressed in PTH chief cells isolated from clinical surgical resections (8A). These cells express high levels (3-fold) of PTH (5A). Gastrin stimulated PTH synthesis ($EC_{50}$=10$^{-9}$M, 40%) and release ($EC_{50}$=4.2×10$^{-10}$M, 50%) (8B). These results demonstrate that PTH synthesis and secretion is coupled to a gastrin receptor (CCK2)-mediated activation. Mean±SEM (n=4 experiments).

Studies described herein demonstrate the expression of gastrin/CCK$_2$ receptors on isolated human PTH chief cells (from human surgical specimens) and that gastrin has a stimulatory effect on human PTH synthesis and release (see FIG. 8). Accordingly, it is demonstrated herein that parathyroid cells are gastrin targets. Since PTH stimulates gastrin release (see FIG. 4), activating parathyroid (PTH) secretion indicates a feed-forward stimulatory loop (G cell to PTH). Expression of the stimulatory histamine H$_1$ receptor was also identified on these cells in studies presented herein.

The expression of stimulatory histamine H$_1$ receptor was also identified on G cells. Histamine is a known activator of cAMP production and PTH secretion in normal and hyperplastic PTH glands. C-cells and C-cell-derived tumors (medullary thyroid carcinomas) express gastrin/CCK$_2$ receptors. In addition, gastrin induces cAMP production and calcitonin release in human thyroid slices.

3. Identification of Functional Gastrin Targets in Bone

In order to evaluate the direct effects of gastrin on bone itself, the presence of gastrin receptors on bone cells and whether gastrin had an effect on bone-derived cells was evaluated (See Example 3).

The effects of gastrin was examined in three different models, 1) mouse calvarial osteoblasts; 2) the human fetal osteoblast cell line, hFOB 1.19; 3) human bone-marrow-derived mesenchymal stem cells (BMMSC). Calvarial osteoblasts are known models to study osteoblast function including proliferation, mineralization and cell signaling. hFOB is a SV40 large T antigen transfected human cell line used as a model to study normal human osteoblast differentiation, osteoblast physiology, and hormonal, growth factor, and other cytokine effects on osteoblast function and differentiation. BMMSC are multipotential marrow stromal cells that can differentiate into a variety of cell types required for tissue regeneration including osteoblasts and chondrocytes and appear to play a pathological role in age-related osteoarthritis.

The results demonstrated herein show that multiple cell types within the bone can be activated/regulated by gastrin. As circulating blood containing gastrin percolates through the bone marrow, alterations in the levels of circulating gastrin are biologically relevant to any bone-derived cell that expresses the CCK2 receptor.

As gastrin is a known proliferative regulator, the effect of gastrin on proliferation (BrdU uptake) in the three different cell models was also studied. The results demonstrated therein show, among other things, that gastrin stimulates proliferation of osteoblast and BMMSCs which is not reversed by a selective gastrin antagonist (GA). The results further indicate that gastrin causes osteoblast dedifferentiation with loss of mineralization. The GA antagonist does not reduce proliferation but the osteo-phenotype remains. Gastrin is shown by the results demonstrated herein to directly affect bone cell function at two levels: the osteoblast and bone marrow-derived stem cells and likely has an effect at the growth plate through the regulation of chondrocyte behavior.

4. Gastrin Studies: Effects of Proton Pump Inhibitors on G-Cell Function

Gastrin secretion is a dynamic physiological response that is regulated by two aspects of aging that are associated with osteoporosis—aging and gastric mucosal atrophy—which is associated with prolonged elevated gastric pH due to loss of acid secreting parietal cells. Sustained elevations in gastric pH which results in elevated levels of circulating gastrin are also associated with long term PPI or H2 receptor antagonist usage. These agents are often used to treat dyspeptic gastric symptoms or gastroesophageal reflux, both of which are relevant particularly in the aging female population.

An acidic gastric environment (low gastric pH) is also important to facilitate the production of ionized calcium that is optimally absorbed by the GI tract.

In humans, both gastrectomy (lack of acid) and pernicious anemia (loss of parietal cells culminating in a low acid state) are well documented as associated with increased risk of osteopenia and fracture. Gastrectomy usually involves resection of the acid secreting cells with significant diminution of gastric acid, pernicious anemia is associated with loss of parietal cells (acid producing), elevated gastric pH (>4) but the stomach retains functional neuroendocrine cells in both the fundus (ECL cells) and antrum (gastrin cells).

Elevated gastric pH and elevated gastrin levels also occurs in both the aged-stomach as well as in long term long-term PPI usage. PPIs have been implicated in an increase in bone resorption and the risk of fracture. Roles of acid inhibition (elevated gastric pH) on G cell function and gastrin secretion are demonstrated herein (see Example 4). The results show, among other indications, that increasing gastric pH significantly affects G cell function. In particular, G cell $Ca^{2+}$ sensing activity and response to physiological regulation is affected.

5. Effects of Acid Blockade on Bone Dynamics: Mastomys Hypergastrinemic Model

The advent of potent acid suppressive medications such as PPIs has revolutionized the management of acid-related diseases. Many millions of individuals use these medications on a continuous or long-term basis.

Significant hypochlorhydria (high gastric pH), particularly among the elderly population who also exhibit a decreased PPI clearance and have a higher prevalence of *Helicobacter pylori* infection, is well known to result in calcium malabsorption. This is supported by a number of studies which have shown that PPI therapy decreases both insoluble calcium absorption as well as bone density. A significant increased risk of hip fracture is therefore associated with long-term PPI therapy, particularly among long-term users of high-dose PPI.

Considering the above-noted problems with PPIs, the results demonstrated herein investigate the effect of acid suppression on the stomach, circulating hormones, the parathyroids, as well as bone physiology in the Mastomys model (see Example 5). The results confirm, among other indications, that hypergastrinemia induced by acid suppressive medications is associated with bone alterations that are similar to the morphological appearances identified with osteoporosis.

6. Effects of Acid Blockade on Bone Dynamics in Ovariectomized Mastomys

Ovariectomy was performed on the Mastomys model to generate a "post-menopausal" phenotype for bone studies. As estrogen loss has been shown herein to regulate G-cells, the specific role of estrogen loss on bone phenotype was evaluated (see Example 6). The results support, among other indications, that circulating gastrin levels amplify estrogen-loss mediated bone changes.

7. Effects on Gastric Neuroendocrine Function and Bone Dynamics: Gene Knockout Mice Models (with and without Ovariectomy)

In rats, gastrectomy (removal of the entire stomach including both the antral G cell and the fundic histamine-secreting ECL cell) or use of PPIs, e.g., omeprazole, leads to malabsorption of calcium phosphate and impaired bone mineral density and osteopenia. A further observation is that the infusion of Gastrin-17 induces hypocalcemia in rats.

In experimental animals, partial and total gastrectomy and gastric vagotomy (truncal/selective etc) (which alter neuroendocrine cell secretion), influence extracellular mineral homeostasis and result in osteopenia as a late sequel.

The mechanisms underlying post vagotomy or post-gastrectomy osteopenia are unknown. Presumably they reflect either direct effects of gastrin on the PTH/$Ca^{2+}$ axis or on bone function or an indirect effect e.g., by histamine. Of note is the observation that ipsilateral vagotomy is curative for hypertrophic pulmonary osteoarthropathy (HPOA) associated with lung cancer. Similarly, vagotomy induced by invasive apical neoplastic lung lesions (Pancoast syndrome) is associated with ipsilateral bone changes in the arm.

Histamine is secreted by the gastric fundic enterochromaffin-like cell (ECL) and is a major regulator of acid secretion since its secretion is primarily driven by circulating gastrin. The ECL cell of the oxyntic (gastric fundic) mucosa is a "closed" endocrine cell localized—i.e. it has no access to the gastric lumen, and therefore does not respond directly to dietary calcium.

The secretory products of the ECL cell include histamine, chromogranin A and pancreastatin, and the calcium-binding protein, calbindin. ECL cells express gastrin and histamine receptors and function chiefly to transduce the gastrin signal (by secretion of histamine) to regulate adjacent parietal cell-mediated acid (HCL) secretion.

Histamine per se has been demonstrated to exhibit an independent influence on bone cell function. Studies, however, are equivocal regarding whether histamine is protective or osteopenic. Excess histamine release in mastocytosis and allergic diseases has been noted to be associated with the development of osteoporosis. This suggests histamine plays a negative role in bone remodeling. Further support of this suggestion is provided by the observation that surgical resection of the acid-producing part of the stomach (oxyntic/fundic mucosa) that contains the ECL cell reduces bone mass in the rat. These observations are further supported by in vitro studies. Thus, in osteoblastic MC3T3-El (El) cells which express histamine $H_{1-3}$ receptors, histamine increases expression of RANKL transcript and protein production. These effects are inhibited by $H_1$ receptor antagonists. In co-cultures, with bone marrow cells (MC3T3-El (El) cells derived from mouse calvaria), histamine stimulated osteoclastogenesis in the presence of vitamin $D_3$. This effect is blocked by preincubation with the neutralizing antibody against ODF/RANKL. Using a microarray approach to investigate differentiation of bone marrow hematopoietic precursor cells into bone-resorbing osteoclasts, it was noted that RANKL stimulated 70 target genes including the $H_1$ receptor. Studies with the $H_2$ receptor antagonist, famotidine, in ovariectomized rats demonstrated inhibition of vertebral bone mass loss through decrease in osteoclast activity. These effects were short-term and were lost by 6 months. A summation of these data indicates that histamine has an active role in the regulation of bone resorption. This observation and is supported by data from a large register-based case: control study demonstrating that long term usage of histamine H1 receptor antagonists reduced the risk of bone fracture.

In ECL cells the critical enzyme responsible for the regulation of histamine secretion is histidine decarboxylase (HDC). HDC null mice are characterized by complete lack of histamine synthesis as well as decreased basal gastric acid secretion and gastrin resistance. These animals exhibit significantly increased femoral thickness and thoracic vertebrae thickness associated with elevated bone mineral content and decreased bone resorption. Osteoclasts were decreased both in number as well as in activity. When HDC null mice are ovariectomized cortical and trabecular bone loss is reduced by 50% indicating that histamine deficiency protects the skeleton from estrogen-driven osteoporosis. The inference is therefore that histamine acts to augments estrogen-mediated bone remodeling.

Although it is plausible to consider that the ECL cell produces an alternative osteotropic amine or peptide, no such hormone has been identified. It therefore seems probable that the role for histamine is as a linkage factor between gastrin, the ECL cell and bone pathophysiology since synthesis and secretion of this amine is so inextricably linked to gastrin.

Studies herein demonstrate a relationship between histamine and gastrin in the mediation of bone metabolism (integrity) using knockout models of gastrin and histamine (see Example 7).

Targeting the gastrin/CCK2 receptor has been studied at a pharmacological level in diseases including pancreatic cancer, gastric neuroendocrine tumors and peptic ulcer. The genesis of the latter relates to the acid-stimulating function of ECL cells through synthesis and release of histamine and the concept that suppression of histamine secretion by blockade of gastrin receptors would decrease acid secretion. One such antagonist is YF476, a 1,4-benzodiazepin-2-one-based gastrin/CCK2 receptor antagonist related to the archetypal analogue L365,260. YF476 has demonstrated efficacy on ECL cell histamine synthesis and release both in vitro and in vivo. Since histamine secretion is activated by gastrin-mediated CCK2 receptor stimulation, a separate physiological event from the acid secretory effects would involve the ability of a CCK2 receptor antagonist to not only block histamine release-related effects on bone but any direct effects of gastrin on bone itself 8. Proof of Principle Studies: Effects of a Gastrin Antagonist on the Ovariectomy-Mediated Bone Phenotype in Three Rodent Models Studied described herein evaluated the effects of the gastrin antagonist, YF476, on OVX-mediated bone density loss/bone alterations in three rodent models with a focus on bone strength studies, morphology and circulating biomarkers (see Example 8).

C. Treatment of Bone Disease or Condition Using Gastrin-Targeting Agents

Studies presented herein demonstrate, among other indications, the presence of CCK2 receptors in bone and the efficacy of gastrin-targeting agents in treating bone disease. Provided are methods and compositions for use of such gastrin-targeting agents for the treatment and prevention of bone diseases or conditions, including those characterized as osteoporosis.

In some embodiments, suitable gastrin-targeting agents include, but are not limited to, gastrin regulators including: gastrin-releasing peptide (GRP) (bombesin), somatostatin, and somatostatin analogs including octreotide (OCTR) and RC-160. In other embodiments, suitable gastrin-targeting agents include CCK2 receptor antagonists include netazepide (YF476) and other 1,4-benzodiazepin-2-one-bastin gastrin/CCK2 receptor agonists. In some embodiments, the gastrin targeting agent is selected from CCK2 receptor agonists: Z-360, L-740093, YM022, RP73870, JB93182, AG041R, proglumide (and analogs), JNJ-2607109 (and derivatives), CI-988, PD-135158, L-365260, LY-288513, L-364718, GW-5823, Lorglumide, CR 2194 (Spiroglumide), PD-149164, PD-135666, CI-1015, RP-69758, TP-680, PD-140548 and Itriglumide (and derivates).

The gastrin-targeting agent may be administered to a subject through either subcutaneous means of administration. In some embodiments, the gastrin-targeting agent is administered via shallow intramuscular injection. In other embodiments, the gastrin-targeting agent is administered intravenously or orally.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1: Isolated G Cell Studies

With reference to FIG. 3, studies were carried out demonstrating a physiological role for the G cell as a $Ca^{2+}$-sensor. Increasing external $Ca^{2+}$ concentration stimulated gastrin release from isolated G cells by mechanisms involving the PKC pathway and $Ca^{2+}$ influx via dihydropyridine-sensitive calcium channels. The $EC_{50}$ was 4.1 mM, and this occurred principally via a PKC-regulated pathway. These results are consistent with the G cell functioning as a dietary (luminal) calcium sensor.

Furthermore, the presence of a PTH receptor was identified on the G cell. With reference to FIG. 4, PTH-mediated gastrin release was demonstrated following cAMP activation. PTH significantly stimulated gastrin release ($EC_{50}$=60 nM) through PKA activation and production of intracellular cAMP demonstrating that the PTH receptor on G cells is functional and that secretion of gastrin by this luminal calcium-sensing antral cell can be regulated by PTH.

Figure 5:
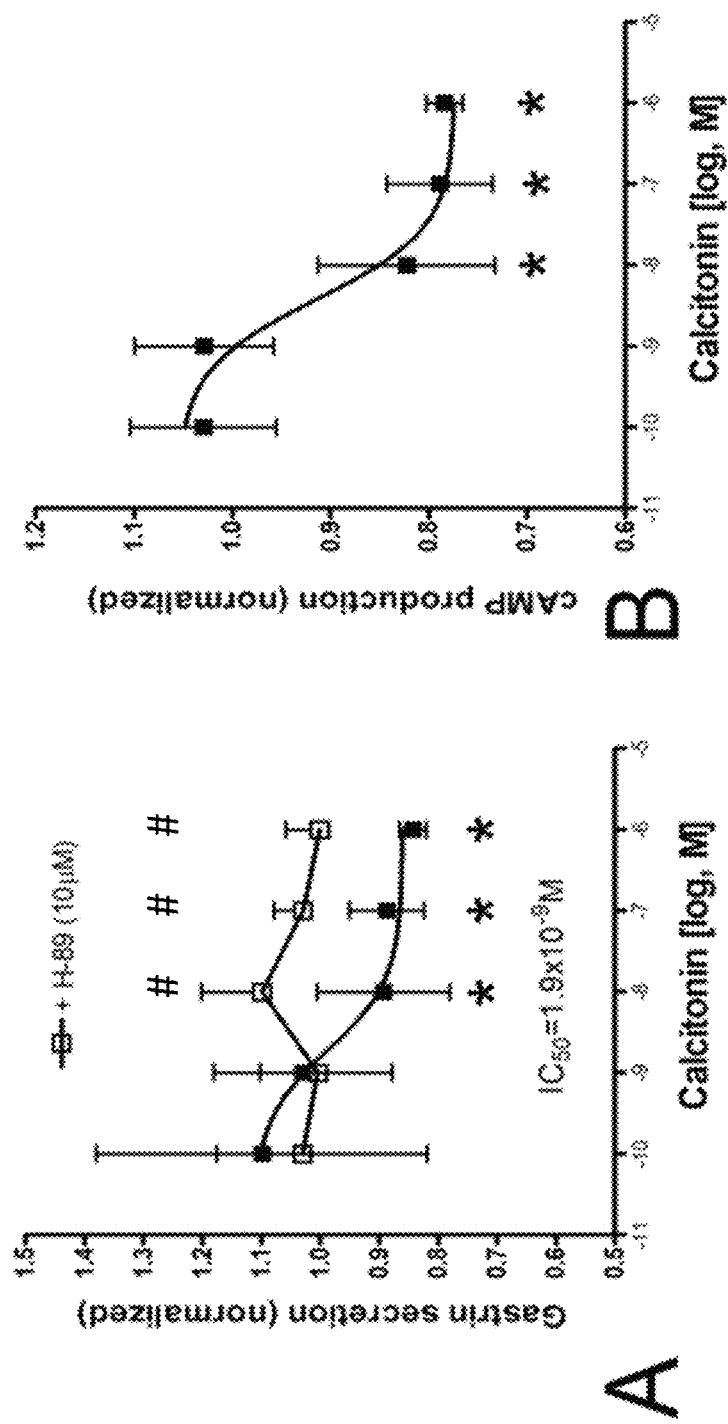
FIG. 5 is two graphs (5A-5B) demonstrating that calcitonin inhibits G cell function. Calcitonin inhibited gastrin release with an estimated $IC_{50}$=1.9 nM (~20%, 5A), an effect that was reversed by preincubation with the PKA inhibitor, H-89 (10 μM). Calcitonin dose-dependently inhibited cAMP production ($I_{50}$=3.8 nM, 20%) (5B). These results demonstrate that gastrin secretion is coupled to a calcitonin receptor-mediated PKA inhibition of cAMP signaling. Mean±SEM (n=4 experiments). *p<0.05 vs. unstimulated, # p<0.05 vs. calcitonin mediated-inhibition.

The calcitonin receptor in G cells was also identified. With reference to FIG. 5, it was shown that calcitonin (from thyroid C cells), in contrast to PTH, inhibited gastrin release through inhibition of cAMP production.

This demonstrates that the G cell, like other PTH/calcitonin targets (e.g. osteoblasts), can be stimulated (PTH) or inhibited (calcitonin) by neuroendocrine cell systems that are not present in the stomach.

These observations provide evidence that the known regulators of calcium homeostasis (through sensing plasma $Ca^{2+}$ levels—PTH/thyroid cells) can directly affect a luminal calcium-sensing cell of the stomach—the gastrin-producing G cell—and modify its secretory profile.

The effect of the ovarian hormone, estrogen on G cell function was evaluated. With reference to FIG. 6, the presence of the estrogen receptor (ESRα) transcript on the gastrin cell was identified using real-time PCR. It further was demonstrated in isolated gastrin cells that 17-estradiol (ESRa agonist) inhibited gastrin release ($IC_{50}$=4.6×10$^{-12}$M), cAMP production ($IC_{50}$=1.1×10$^{-12}$M) and MAPK activity (FIG. 6).

This information indicates that altering the estrogen milieu consistent with the menopausal state will profoundly alter/stimulate G cell function (signaling and secretion). This is consistent with previous reports in aged rats of the existence of a milieu that includes increased G cell function and a high PTH. This combination is well accepted as related to the development of osteoporosis.

Figure 7:
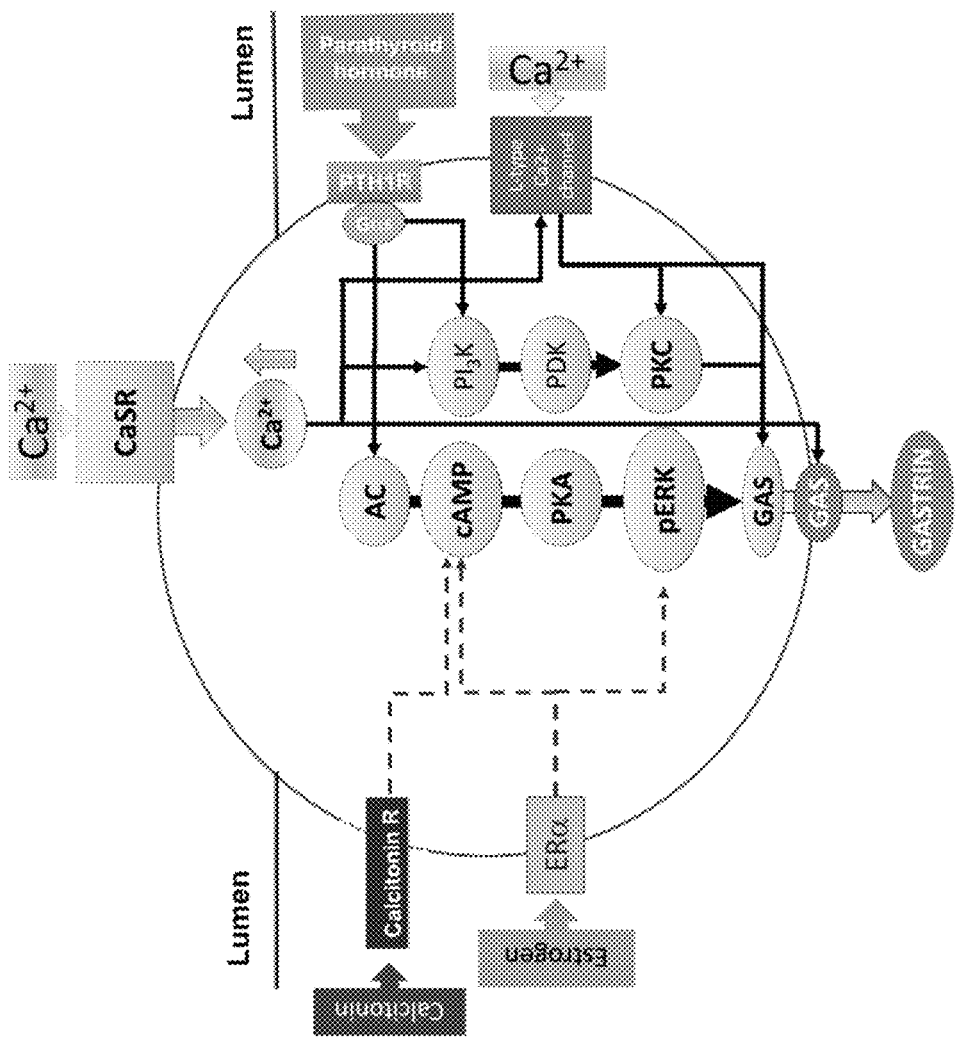
FIG. 7 is a model of G-cell regulation. Luminal agents including dietary calcium either directly or indirectly induce ERK phosphorylation through activation of adenylate cyclase (AC) via coupling to Gas which results in gastrin secretion. PTH through the G-protein coupled PTH1 receptor also stimulates gastrin release through this pathway. ERK phosphorylation may positively affect Ca2+ influx which is directly increased by the diet. L-type calcium channels similarly regulate secretion via activation of PKC. Inhibitors of gastrin secretion include calcitonin (via inhibition of cAMP) and estrogens that activate ERα to inhibit both cAMP and the MAPK pathway. AC: adenylate cyclase; GAS: gastrin; PDK: phosphoinositide dependent kinase; PKA: protein kinase A; Dashed lines reflect inhibition, solid lines stimulation.

With reference to TABLE 1, a comparison of transcripts with isolated preparations of neuroendocrine EC and ECL cells demonstrates that the G cell is the only cell that can sense luminal calcium since it is the only neuroendocrine cell that expresses CaSR but not calbindin. With reference to FIG. 7, this indicates that G cell gastrin secretion may be directly regulated by PTH secreted by the parathyroid chief cells, calcitonin from thyroid C-cells and estrogen from ovarian cells.

TABLE 1

Comparison of the presence of calcium metabolism-associated transcripts and neuroendocrine receptors in G cells, EC cells and ECL cells as measured by transcriptome (U133A microarrays) analysis

| | G cell | EC cell | ECL cell |
|---|---|---|---|
| Calcium metabolism | | | |
| PTH receptor | YES | NO | NO |
| Calcitonin receptor | YES | NO | NO |
| Vitamin D receptor | YES | NO | NO |
| CaSR | YES | NO | NO |
| ESRα | YES | YES | YES |
| Intracellular calcium translocation | | | |
| Calbindin | NO | YES | YES |
| Neuroendocrine receptors | | | |
| Histamine H3 receptor | YES | NO | YES |
| Serotonin 5-HT3 receptor | YES | NO | NO |

CaSR: calcium sensing receptor;
ESRα = estrogen alpha;
H3 = histamine subtype 3;
5-HT3: serotonin subtype 3;
PTH: parathyroid The results identify the G cell as the pivotal neuroendocrine cell in the gut/parathyroid calcium homeostasis axis.

Example 2: Gastrin Target Studies (In Vitro)

Cell types were evaluated as potential gastrin targets. Regulation by the gastrin cell of the calcium homeostasis axis through gastrin release was assessed.

The expression of gastrin/$CCK_2$ receptors on isolated human PTH chief cells (from human surgical specimens) has been demonstrated. With reference to FIG. 8, it was further demonstrated that gastrin has a stimulatory effect on human PTH synthesis and release. These results indicate that parathyroid cells are a gastrin target. Since PTH stimulates gastrin release (see FIG. 4), activating parathyroid (PTH) secretion indicates a feed-forward stimulatory loop (G cell to PTH). Expression of the stimulatory histamine $H_1$ receptor was also identified on these cells.

Figure 9:
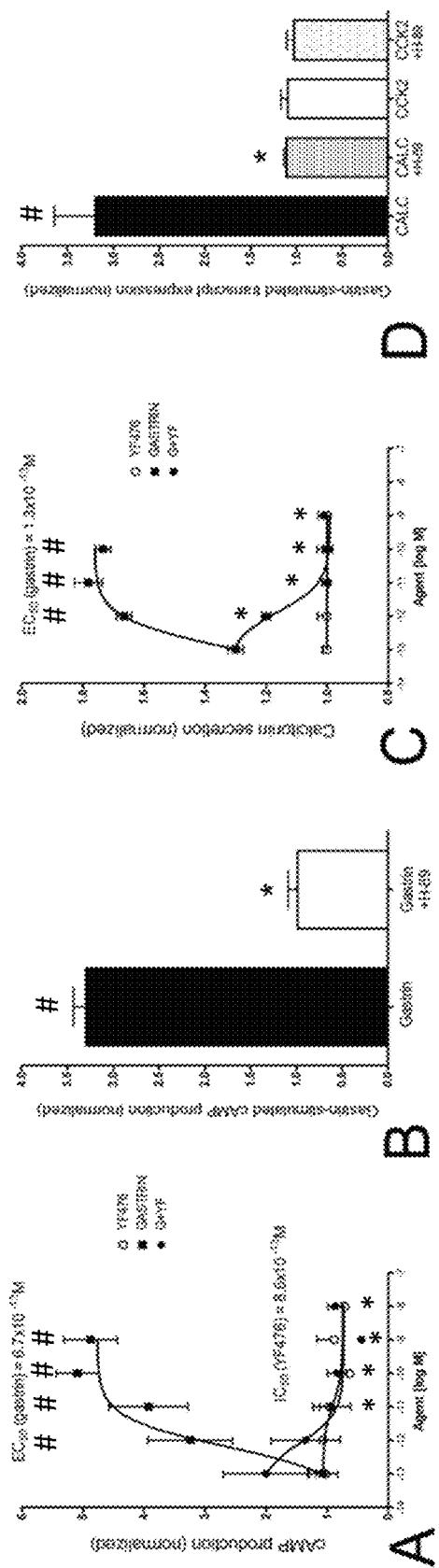
FIG. 9 is a series of graphs (9A-9D) showing that gastrin stimulates thyroid C-cell (MTC-SK) function. Gastrin stimulated cAMP production ($EC_{50}$=6.7×10$^{-13}$M, ~5-fold) was reversed by the selective $CCK_2$ receptor antagonist, YF476 (9A). YF476 alone had no significant effect. The gastrin-stimulatory effect on cAMP could be inhibited by preincubation with the PKA inhibitor, H-89 (10 μM) (9B). Calcitonin secretion was dose-dependently affected by gastrin, an effect reversed by YF476 (9C). Gastrin (0.1 nM) stimulated (~3-fold) calcitonin gene transcription, an effect reversed by preincubation with H-89 (10 μM) (9D). CCK2 receptor expression was not inhibited by H-89 (9D). These results identify that calcitonin synthesis and release is regulated by gastrin receptor (CCK2)-mediated PKA activation and cAMP signaling. Mean±SEM (n=4 experiments). # p<0.05 vs. unstimulated, *p<0.05 vs. gastrin (0.1 nM) alone.

With reference to FIG. 9, Gastrin stimulated both cAMP as well as calcitonin release from the well-differentiated human MTC cell line, MTC-SK, effects that were reversed by the selective $CCK_2$ antagonist, YF476 ($IC_{50}$=8.6×10$^{-13}$M). These results indicate that thyroid C cells represent a gastrin target. Since calcitonin inhibits gastrin release (see FIG. 5) C-cell activation would provide a feedback inhibitory loop.

In order to assess the overall responsiveness (stimulatory or inhibitory) of the thyroid/parathyroid system to gastrin, the effects of gastrin on parathyroid/MTC-SK co-culture systems were evaluated. It was assessed whether Gastrin was either a stimulator of bone resorption (through increased PTH synthesis and release) or an inhibitor of this process through calcitonin release.

Figure 10:
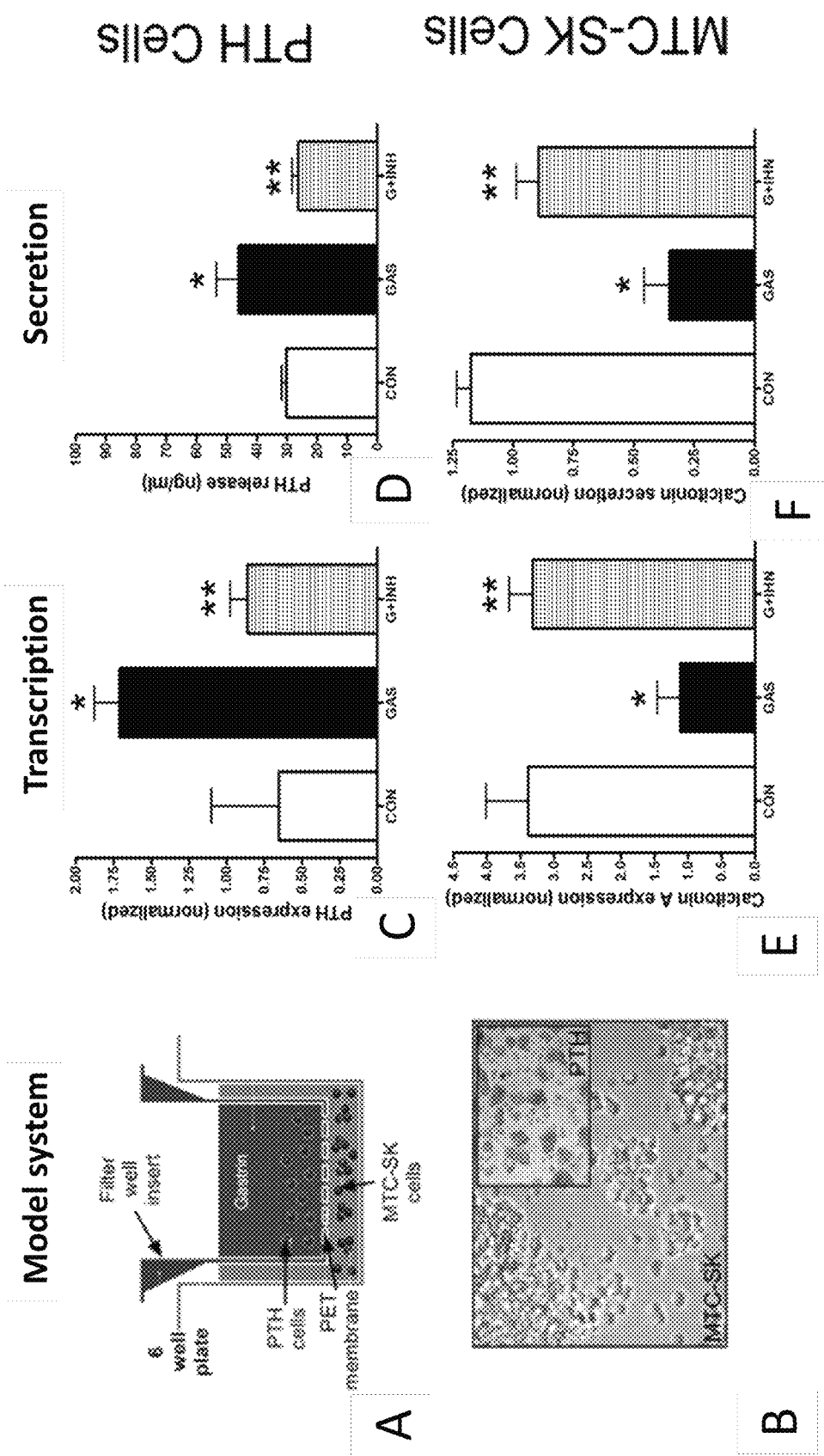
FIG. 10 is an illustration (10A), photomicrograph (10B) and series of graphs (10C-10F) showing an effect of gastrin on PTH and MTC-SK synthesis and secretion—a co-culture model system. Human PTH cells isolated from surgical specimens were co-cultured with the MTC-SK cell line. A diagram detailing the cell locations and target location site is included in 10A while photomicrographs demonstrate growth of each of these cell types (10B). Addition of gastrin to the co-culture system significantly stimulated PTH transcription (~75%, 10C) and secretion (~60%, 10D). These effects could be reversed by preincubation (10 mins) with the selective $CCK_2$ receptor antagonist, YF476 (10 nM). In contrast, gastrin inhibited both calcitonin transcription (to basal—10E) and release (~70%—10F). These results identify that the principal effect of gastrin in a model system is to stimulate PTH and inhibit calcitonin. The latter effect is in contrast to the stimulatory effect of gastrin in single-culture (MTC-SK cells alone) experiments. CON=control, GAS=gastrin (10$^{-10}$M), G+INH=gastrin+YF476 (10$^{-11}$M). PET=polyester membrane (0.4 mm). Mean±SEM, n=3. *p<0.05 vs. control (unstimulated), **p<0.05 vs. gastrin (10$^{-10}$M).

With reference to FIG. 10, stimulation of the $CCK_2$ receptor (expressed in both parathyroid and thyroid C-cells), resulted in a significant elevation in PTH transcription and secretion from the cultured PTH cells. In contrast, gastrin resulted in significant inhibition of calcitonin synthesis and release. These effects were reversed by preincubation with the selective $CCK_2$ antagonist, YF476.

These results indicate that gastrin-stimulation of thyroid C cells is reversed by PTH released from the parathyroid cells. This is evidence that within this model co-culture system, the effects of gastrin is predominantly a PTH-mediated effect. In healthy volunteers, the effect of gastrin infusion is to increase PTH secretion rather than calcitonin (significantly lower release). This suggests that any in vivo effect of gastrin on the thyroid gland is principally related to the parathyroids and PTH release.

These results support that a gut (gastric) hormone release by a luminal-sensing cell (the G cell) directly regulates the parathyroid and indirectly, thyroid C-cell calcitonin secretion.

Example 3: Identification of Functional Gastrin Targets in Bone

In order to evaluate the direct effects of gastrin on bone itself, the presence of gastrin receptors on bone cells and whether gastrin had an effect on bone-derived cells was evaluated. QPCR, western blot and immunohistochemistry techniques were used to identify receptor expression in bone. Thereafter, the effects of gastrin was examined in three different models, 1) mouse calvarial osteoblasts; 2) the human fetal osteoblast cell line, hFOB 1.19; 3) human bone-marrow-derived mesenchymal stem cells (BMMSC).

Figure 11:
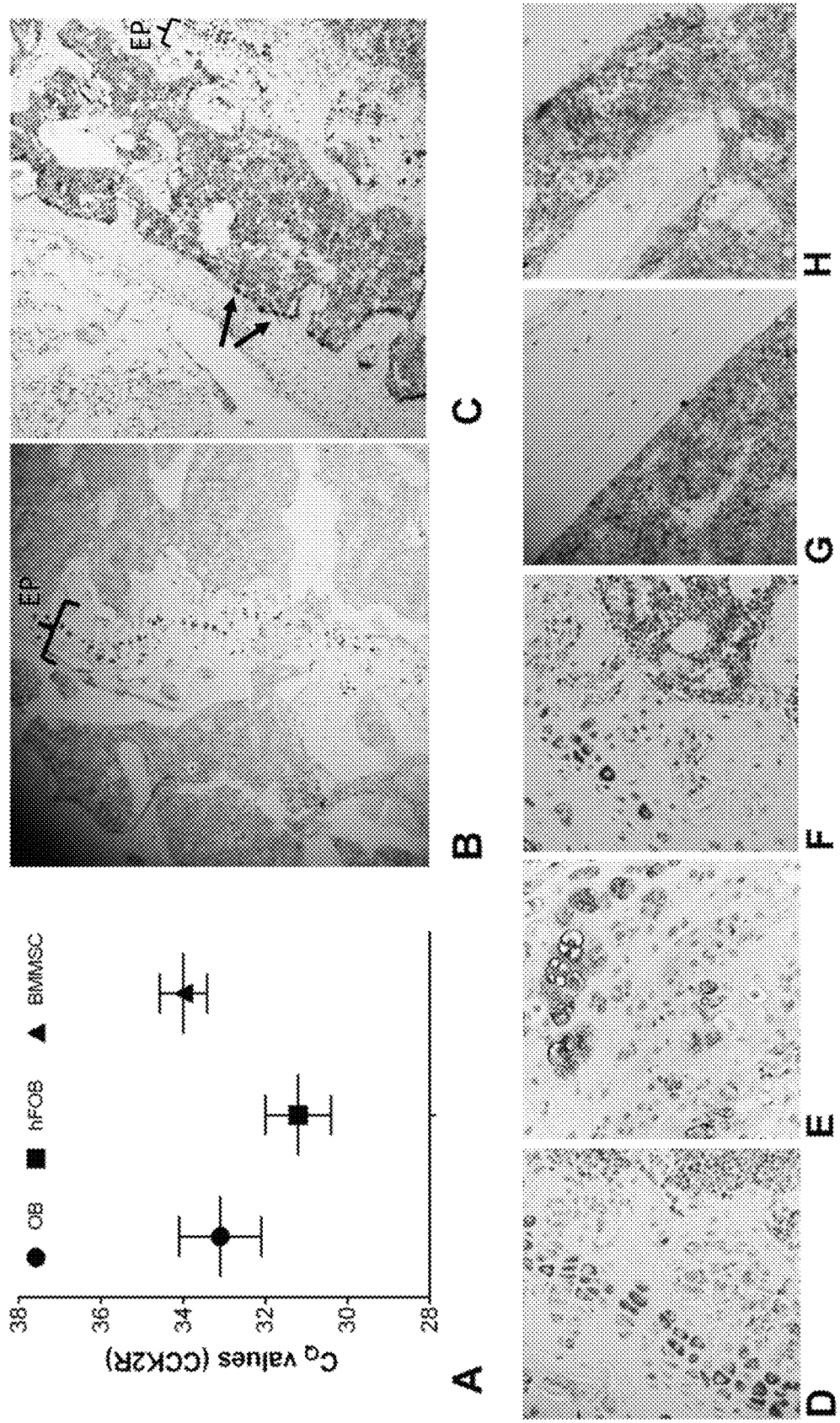
FIG. 11 is a graph (11A) and a series of photomicrographs (11B-11H) demonstrating CCK2 receptor expression in isolated bone-derived cells and in bone. Transcript levels of the CCK2 receptor was identified in calvarial osteoblasts (OB), the hFOB cell line (hFOB) and in human bone marrow derived mesenchymal stem cells (BMMSCs) (11A). Using immunohistochemistry, specific immunostaining was identified in the epiphyseal plate (EP) as well as in marrow cells (arrows) (11B, 11C—100× magnification). Cells involved in endochondral ossification express receptors (11D, E, F) as do osteoblasts (11F). There was evidence of CCK2R-positive osteoblast cells lining the endosteum (11G) as well as in healing bone (11H). We interpret these results to indicate that the CCK2R is expressed on chondrocytes, osteoblasts and mesenchymal marrow cells and the CCK2R is involved in the regulation of ossification and bone healing. Targeting the receptor likely regulate these phenomena. CCK2R immunostaining=brown cells (DAB), counterstain=hematoxylin. 11D-H: magnification=400×.
Figure 12:
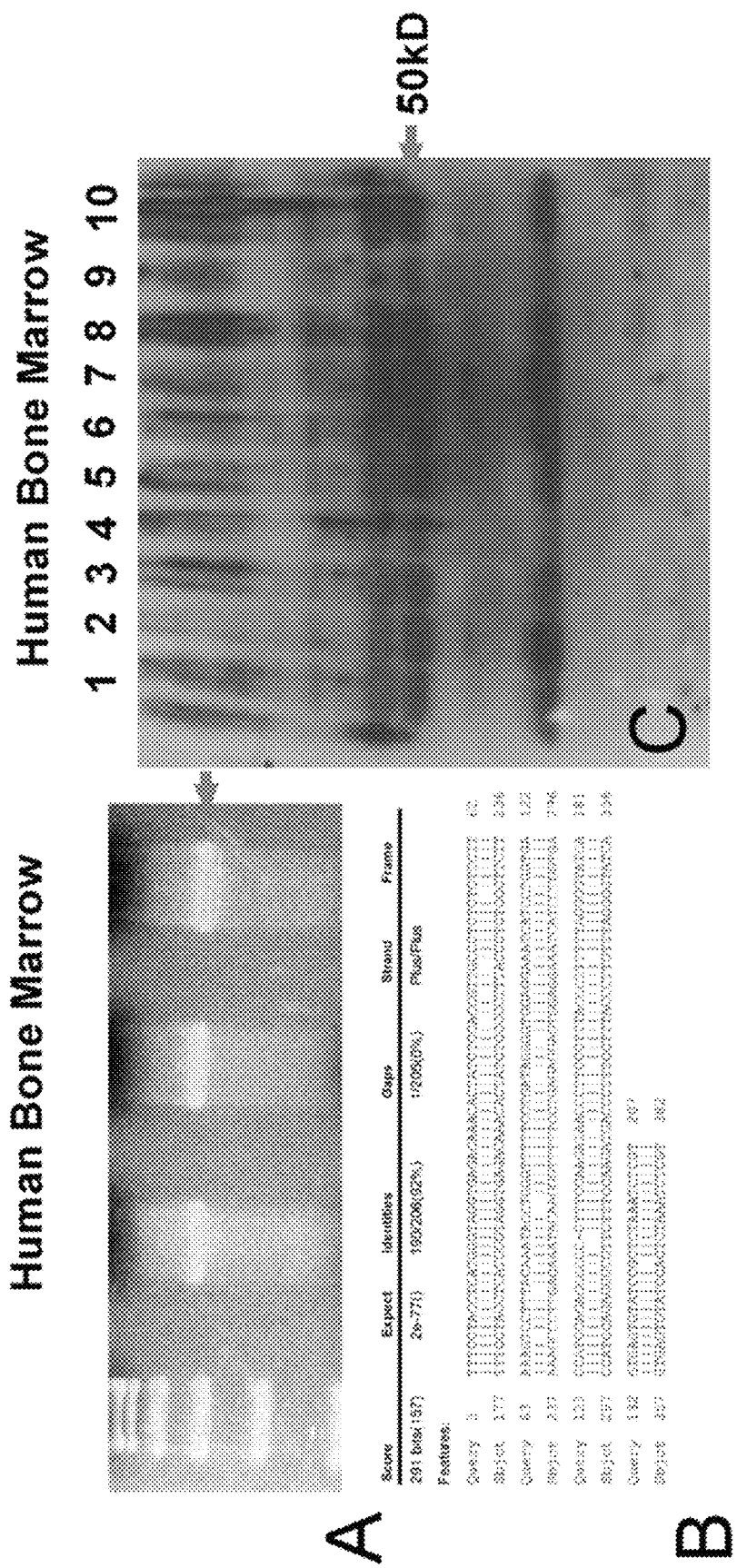
FIG. 12 is a photograph (12A), sequence analysis (12B), and photograph (12C) showing expression of the gastrin/CCK2 in human bone marrow samples. Standard PCR identified a band of ~320 base pairs (arrow) in isolated cortical bone marrow—samples derived from amputation for atherosclerosis induced limb ischemia (no evidence of osteomyelitis) (12A). Sequence analysis (BioEdit) between Query (SEQ ID NO: 1) and Sbjct (SEQ ID NO: 2) sequence strands identified a 92% homology with the canonical CCK2 gene (12B). Western blot confirmed expression of CCK2 in the 10 samples studied (arrow—50 kD) (12C).

CCK2 Receptor:

Using qRT-PCR, the expression of the CCK2 receptor was identified in calvarial osteoblasts, the hFOB cell line and human BMMSCs (FIG. 11A). Expression was identified in all models, with CQ values ranging from 31.2-34. Immunohistochemistry (IHC) identified gastrin receptors in mouse bone—specific immunostaining was identified in chondrocytes in the growth plate. Some expression was identified in osteoblasts as well as in cells that lined the endosteum (FIG. 11B-C). Standard PCR and western blot was also undertaken in human cortical bone marrow-samples derived from 10 bone marrows (collected following amputation for atherosclerosis induced limb ischemia (no evidence of osteomyelitis). PCR identified a band of the size corresponding to the CCK2 receptor (FIG. 12A). This was sequenced (Sanger) and identified to exhibit 92% homology with the CCK2R (FIG. 12B). Western blot confirmed CCK2 receptor protein expression in all the human samples (FIG. 12C).

Summary:

A gastrin target was identifiable in mouse calvarial osteoblast cells, in the hFOB and BMMSC cell lines as well as in bone including the growth plate (chondrocytes) and in human bone marrow (endosteal collections) indicating that multiple cell types within the bone can be activated/regulated by gastrin. Since circulating blood containing gastrin percolates through the bone marrow, alterations in the levels of circulating gastrin are biologically relevant to any bone-derived cell that expresses the CCK2 receptor.

Figure 13:
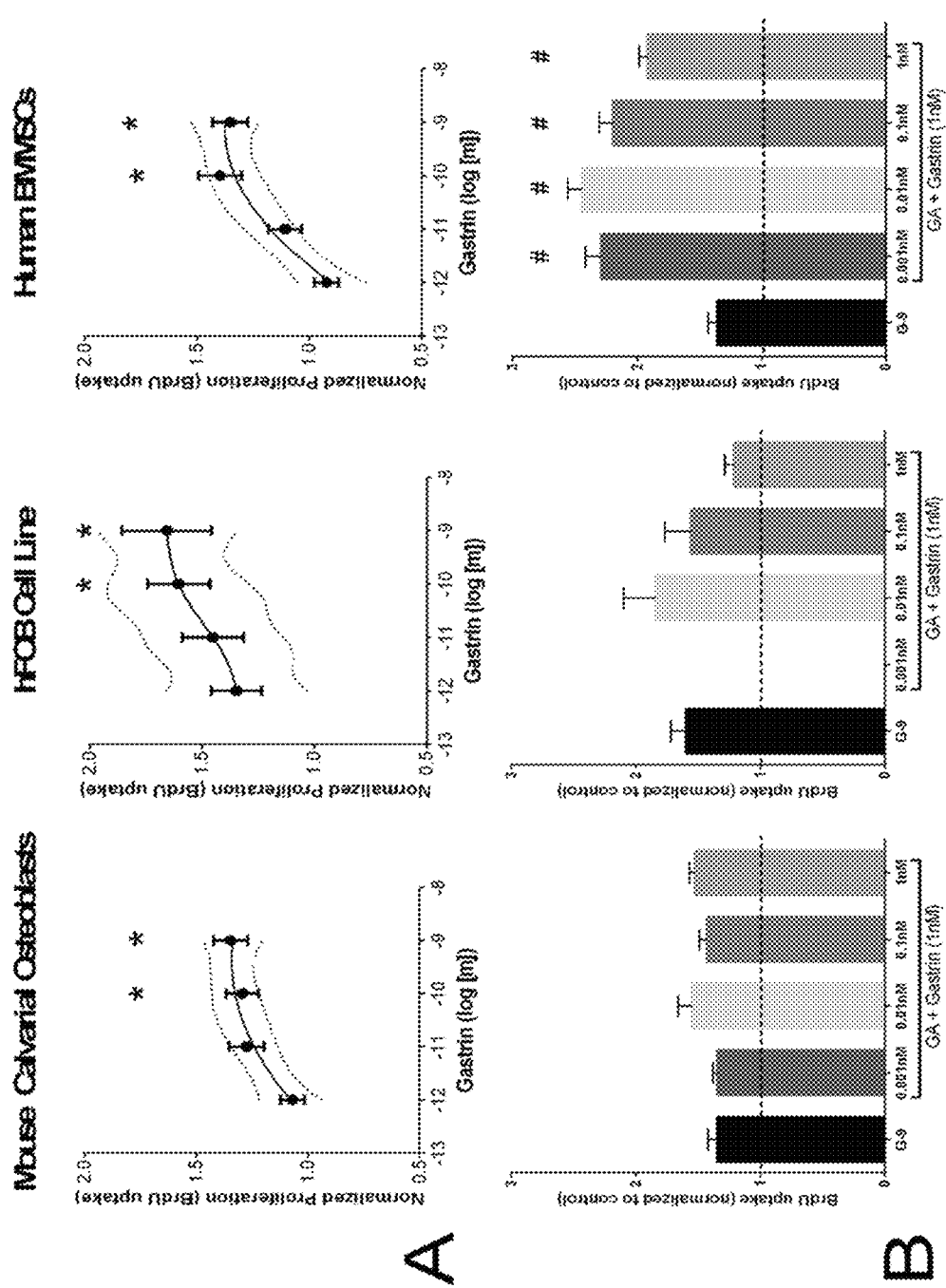
FIG. 13 is a set of graphs (13A and 13B) demonstrating the effect of gastrin and targeting CCK2 on bone-derived cell proliferation. Gastrin dose-dependently stimulated BrdU uptake in all cell types with an $EC_{50}$=1-2×10$^{-11}$M (13A). This was not reversed by the selective CCK2 receptor antagonist, YF476, which did appear to augment proliferation, particularly in BMMSCs (13B). Mean±SEM (n=4 experiments). *p<0.05 vs. unstimulated, # p<0.05 vs. gastrin (0.1 nM).
Figure 14:
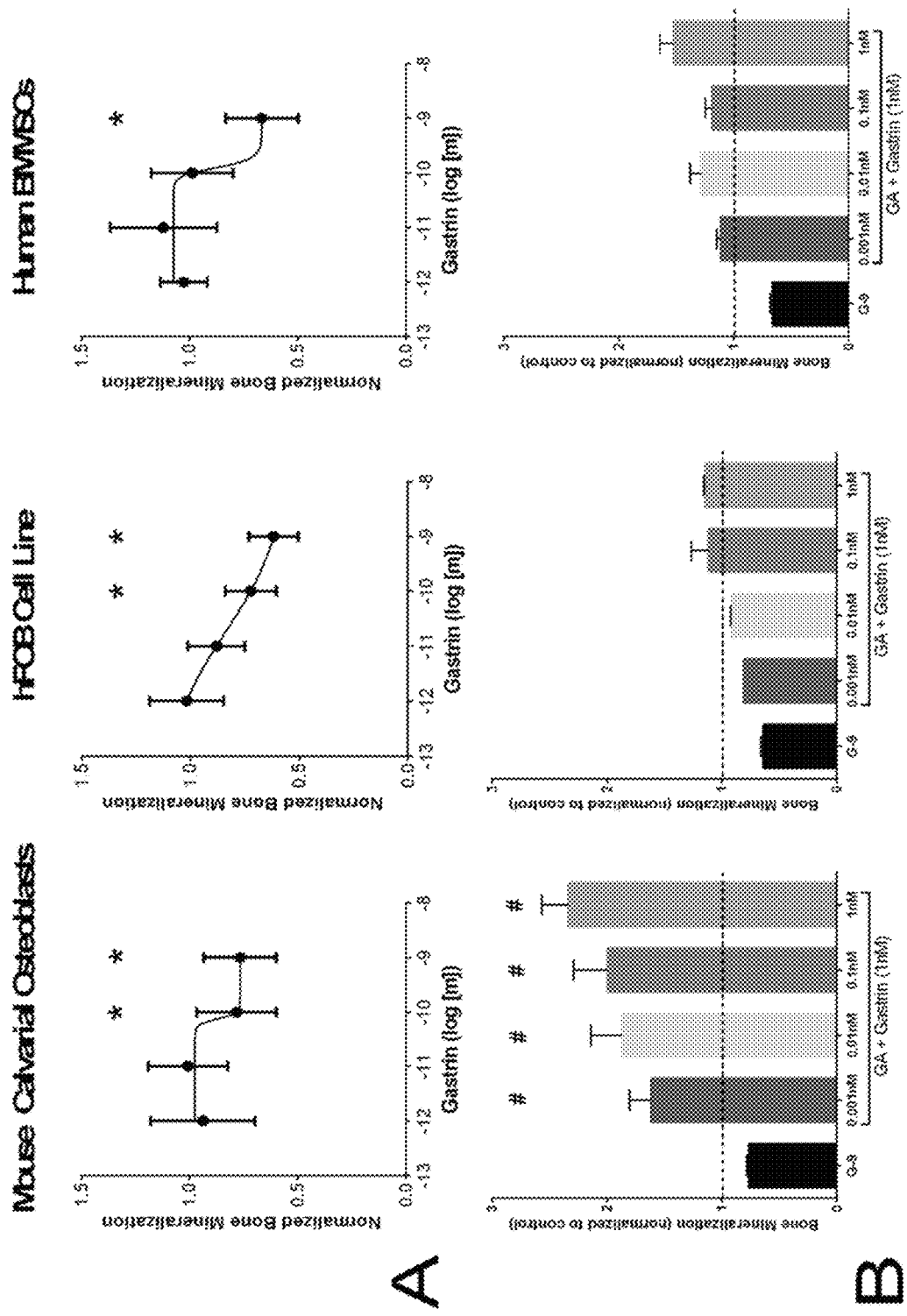
FIG. 14 is a set of graphs (14A and 14B) demonstrating the effect of gastrin and targeting CCK2 on bone-derived cell mineralization. Gastrin dose-dependently inhibited bone mineralization (measured using Ostemalge) in all cell types with an $IC_{50}=3.2\times10^{-11}-1.3\times10^{-10}$M (14A). This was not reversed by the selective CCK2 receptor antagonist, YF476, which augmented mineralization, particularly in calvarial osteoblasts (14B). Mean±SEM (n=4 experiments). *p<0.05 vs. unstimulated, # p<0.05 vs. gastrin (0.1 nM).

Gastrin Effects In Vitro:

Gastrin is a known proliferative regulator, so the effect of gastrin on proliferation (BrdU uptake) was initially studied in the three different cell models. Gastrin stimulated proliferation in all three cell types with an $EC_{50}$ of $1-2\times10^{-11}$M (FIG. 13A) and a maximal effect of ~50% (1 nM). These stimulatory effects on proliferation were not inhibited by pre-incubation with the selective gastrin antagonist, YF476 (FIG. 13B). This compound appeared to augment proliferation in BMMSC cells. In order to assess the biological implication of gastrin activation of osteoblasts and BMMSCs, studies were performed to evaluate whether these gastrin-mediated effects resulted in bone mineralization. The binding of fluorescent Osteomalge to the hydroxyapatite portion of mineralized nodules was measured. Gastrin inhibited bone mineralization in all three cell types with an $IC_{50}$ of $3.2\times10^{-11}$–$1.3\times10^{-10}$M (FIG. 14A) and a maximal inhibitor effect of ~30-50% (1 nM). These inhibitory effects on mineralization were inhibited by pre-incubation with the selective gastrin antagonist, YF476 (FIG. 14B). This compound appeared to specifically augment mineralization in mouse osteoblast calvarial cells.

Summary:

Gastrin stimulates proliferation of osteoblast and BMMSCs which is not reversed by the gastrin antagonist. Gastrin-mediated proliferation is associated with a loss of mineralization indicating a reversal of the osteoblast phenotype. The GA reversed this gastrin inhibitory effect. These results indicate that gastrin causes osteoblast dedifferentiation with loss of mineralization. The antagonist does not reduce proliferation but the osteo-phenotype remains. This effect was most marked in calvarial osteoblasts.

In order to further assess the biological implication of gastrin activation, studies were performed to evaluate whether these gastrin-mediated effects increased expression of bone morphogenetic protein 2 (BMP2—involved in osteoblast differentiation), RANKL (the osteoclast activating receptor expressed on osteoblasts) and Macrophage colony-stimulating factor (M-CSF—involved in regulation of bone marrow progenitor cells and activator of osteoclast activity).

Figure 15:
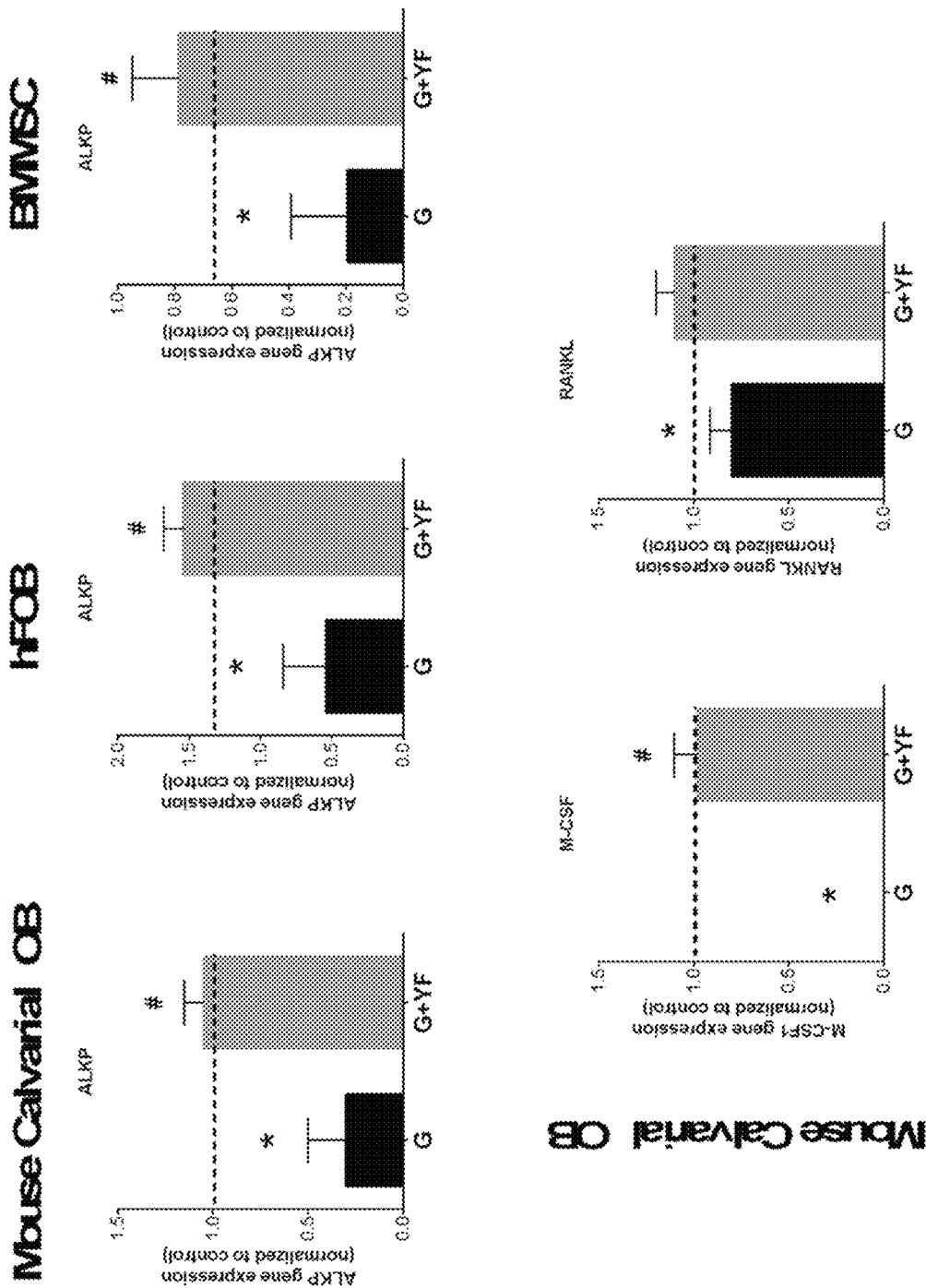
FIG. 15 is a set of graphs demonstrating the effect of gastrin and targeting CCK2 on bone-derived cell gene expression. Gastrin (1 nM) inhibited expression of the osteoblast-differentiation gene, alkaline phosphatase (ALKP) in all cell types (top row). This was reversed by the selective CCK2 receptor antagonist, YF476 (1 nM). Gastrin also inhibited M-CSH and RANKL in osteoblasts, which was normalized by YF476 (bottom row). Mean±SEM (n=4 experiments). *p<0.05 vs. unstimulated, # p<0.05 vs. gastrin (1 nM).

In mouse calvarial cultures, gastrin (1 nM) completely inhibited MSCF-1 gene expression as well as inhibited RANKL transcription (0.8-fold) and ALKP (FIG. 15). In hFOB, gastrin also inhibited these transcripts. Preincubation with YF476 reversed and normalized these effects. Neither of these genes were identified in BMMSC, but the gastrin effects were noted for ALKP while BMP2 was not identified in any cell type. This identifies that gastrin effects are catabolic and inhibiting them with YF476 results both in a normalization of osteoblast function as well as engenders an anabolic phenotype.

These data indicate that gastrin regulates not only osteoblast proliferation and differentiation but is also involved in the regulation of progenitor cells. In addition, gastrin affects BMMSCs to proliferate. The YF compound reversed the phenotypic effects without inhibiting proliferation. Gastrin therefore directly affects bone cell function at two levels: the osteoblast and bone marrow-derived stem cells and likely has an effect at the growth plate through the regulation of chondrocyte behavior.

Example 4: Gastrin Studies: Effects of Proton Pump Inhibitors on G-Cell Function As PPIs have been implicated in an increase in bone resorption and the risk of fracture, the role of acid inhibition (elevated gastric pH) on G cell function and gastrin secretion was assessed. G cells were isolated from the antral mucosa of mice (Mastomys—*Praomys natalensis*) that had been treated with the irreversible H2 receptor antagonist—Loxtidine 1 mg/L—in drinking water to generate sustained hypergastrinemia. This animal has been extensively studied as a model of gastric acid pathophysiology relevant to long-term pharmacological inhibition of acid secretion (low acid state pathobiology).

Mastomys (6-9 months) treated for 30 days with irreversible gastric acid suppression, exhibited elevated plasma gastrin levels (104±23 pg/ml versus 28±13 pg/ml in untreated animals, p<0.05). This is a reflection of the loss of low pH-inhibited gastrin release (consequent elevated gastric pH levels). Such treatment therefore results in an achlorhydric and hypergastrinemic animal model.

The gastrin content, gastrin transcript levels as well as basal gastrin release were all significantly (p<0.05) elevated in G cells isolated from achlorhydric (high pH stomachs—low acid exposure G cells) compared to G cells isolated from non-treated animals (TABLE 2).

TABLE 2

Summary of differences between normal gastric pH and elevated gastric pH (low acid) in isolated rodent G cells

| | Gastrin Content (pg/ng protein) | Gastrin Transcript* | Basal/ release pg/10³ cells/ | GRP ($EC_{50}$) | Calcium ($EC_{50}$) | OCTR ($IC_{50}$) |
|---|---|---|---|---|---|---|
| Normal G-cells | 137,343 ± 83,540 | 0.12 ± 0.06 | 16.7 ± 3.2 | 0.13 mM | 4 mM | 28 pM |
| Low acid G-cells | 283,179* ± 46,371 | 0.58* ± 0.27 | 139* ± 36 | 1.0 nM | 10 mM | 140 pM |

*p < 0.05 vs. normal G cells.
normalized to βActin, GAPDH and HPRT.
GRP = gastrin releasing peptide,
OCTR = octreotide With reference to TABLE 2, elevated gastric pH (low acid states) stimulates G cell gastrin content (>2-fold), transcription (>4-fold) and secretion (>8-fold). The physiological response of these cells to stimulatory ligands e.g., GRP and calcium is decreased—the $EC_{50}$s are increased. Similarly, these cells are less sensitive to inhibitors e.g., Octreotide (OCTR), the $IC_{50}$ is increased ~5-fold.

Regulators of gastrin release, GRP (bombesin) and somatostatin (OCTR) exhibited an increased (GRP: $EC_{50}$: 1.1 pM versus 1 nM respectively) and decreased efficacy (somatostatin analog, octreotide: 28 pM to 140 pM), respectively (TABLE 2). In addition, "hypergastrinemic" G cells were ~100% less sensitive at detecting calcium ($EC_{50}$=10 mM vs. 4 mM in normogastrinemic cells).

These data demonstrate that increasing the gastric (pH) milieu in vivo significantly affects G cell function. Increasing gastric pH (as would be present in aged individuals or patients on PPIs) specifically altered the G cell $Ca^{2+}$ sensing sensitivity and response to physiological regulation. This demonstrates that long-term inhibition of parietal cell function and decrease of acid secretion substantially alters the antral G cell response to the luminal environment.

This observation is of clinical relevance since under conditions of a high luminal pH more gastrin is produced. Hypergastrinemia is important since gastrin both stimulates PTH release and has a direct effect on bone cells (see FIGS. 8, 10, 11).

Example 5: Effects of Acid Blockade on Bone Dynamics: Mastomys Hypergastrinemic Model The effects of acid suppression on the stomach, circulating hormones, the parathyroids as well as on bone physiology were examined in the Mastomys model.

Very little is known regarding bone biology in these animals. One study identified degeneration of intervertebral disks in the majority (~80%) of animals >9 months and severe osteo-arthritic changes in diarthrodial joints (elbows, knees).

Among laboratory rodents, the Mastomys, with the exception of a single strain of inbred mice (STR/IN), appears to be most susceptible to osteo-arthritis.

Animals (females) 4-6 months old were treated with Loxtidine for 60 or 120 days. Age- and sex-matched untreated animals provided a control group.

Figure 16:
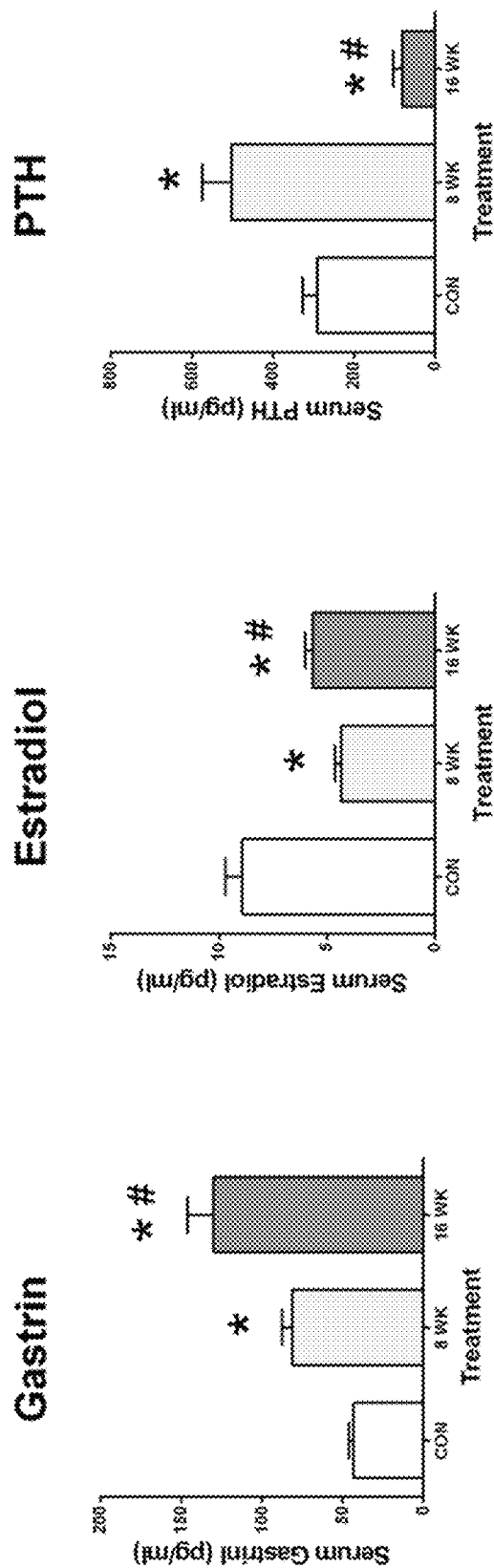
FIG. 16 demonstrates the effects of short-term and chronic hypergastrinemia on circulating hormone levels in the Mastomys models. Gastrin levels were significantly elevated at both 8 (~2-fold) and 16 weeks (~3.5-fold) of treatment. Estrogen (estradiol) was decreased (~50%) in both short- and long-term hypergastrinemic animals. PTH was significantly elevated at 8 weeks (~75%) but significantly reduced at 16 weeks (~3-fold). These results demonstrate that short-term hypergastrinemia in an in vivo model inhibits estrogen release with reciprocal activation of PTH secretion. Long-term hypergastrinemia is also associated with a reduction in estradiol, but this does not result in elevated PTH. The mechanism for the latter is not known but may reflect down-regulation of the CCK2 receptor or its signaling responses in the PTH gland exposed to long-term gastrin stimulation. Mean±SEM, *p<0.05 vs. control animals. # p<0.05 vs. 8 week treated animals. CON=control animals, 8 wk=short-term hypergastrinemia, 16 wk=long-term hypergastrinemia.

Circulating hormones: Hormone analysis (ELISA) confirmed gastrin/PTH and estradiol alterations as function of $H_2$ receptor blockade. Specifically, a short-term elevation in gastrin secretion (8 weeks of Loxtidine treatment) was associated with elevated PTH secretion and estradiol/estrogen inhibition (FIG. 16). Longer term (16 weeks), chronic hypergastrinemia was associated with inhibition of PTH and estradiol.

The Stomach:

Activation of ECL histamine (histidine decarboxylase—HDC) (FIG. 17A) and G cell gastrin (at an mRNA level) during hypergastrinemia (FIG. 17B) was demonstrated. This was associated with activation of PTH1R (at mRNA and protein levels), and selective decreases in gastric ERα (at mRNA and protein levels) during short-term hypergastrinemia; this then increased at 16 weeks and was associated with activation of CaSR (at mRNA and protein levels) during hypergastrinemia (FIG. 17A-C).

Figure 18:
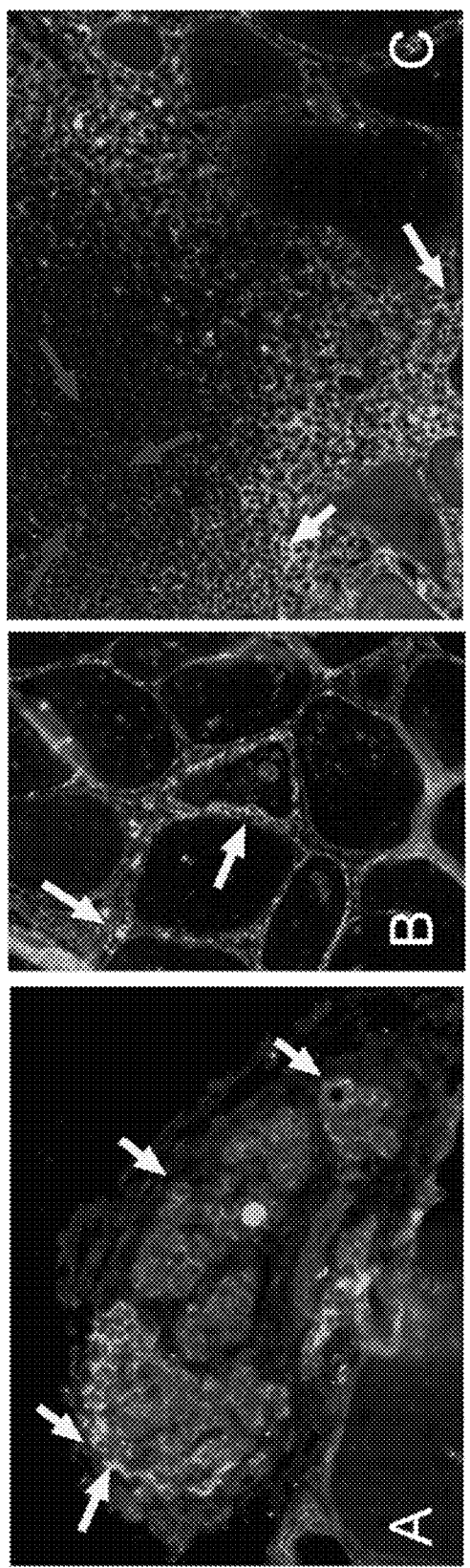
FIG. 18 demonstrates CCK2 receptor expression in the parathyroid and thyroids. Immunostaining for the CCK2 receptor identified that the majority of parathyroid cells within a parathyroid gland are CCK2 positive (different stains reflect membrane-bound expression [arrows] and cell nuclei] 18A). Within the thyroid, individual C cells can be identified that are stained by CCK2 antibodies (staining reflects membrane-bound expression [arrows]—18B, 18C (lower two arrows)). In contrast, infiltrating immune cells within the Mastomys thyroid gland are CCK2 negative (upper three arrows, blue nuclei only) (18C). These results demonstrate membrane-expression of the CCK2 receptor in both PTH and thyroid cells. This is consistent with in vitro results showing the effects of gastrin on cells isolated from these structures. Nuclei stain=DAPI, other stain=FITC labeled CCK2. Antibody from Abeam (ab14439, rabbit polyclonal, 1:100 dilution).

The Parathyroid:

Using immunohistochemistry, CCK2 receptor expression in the parathyroid and thyroid of Mastomys was demonstrated (FIG. 18). The results identify that both parathyroid cells as well as thyroid C-cells express the gastrin receptor. The CCK2 receptor in the parathyroids provides the basis for a G-cell: PTH axis whereby parathyroid secretion (e.g., of PTH) may be regulated by gastrin.

Figure 19:
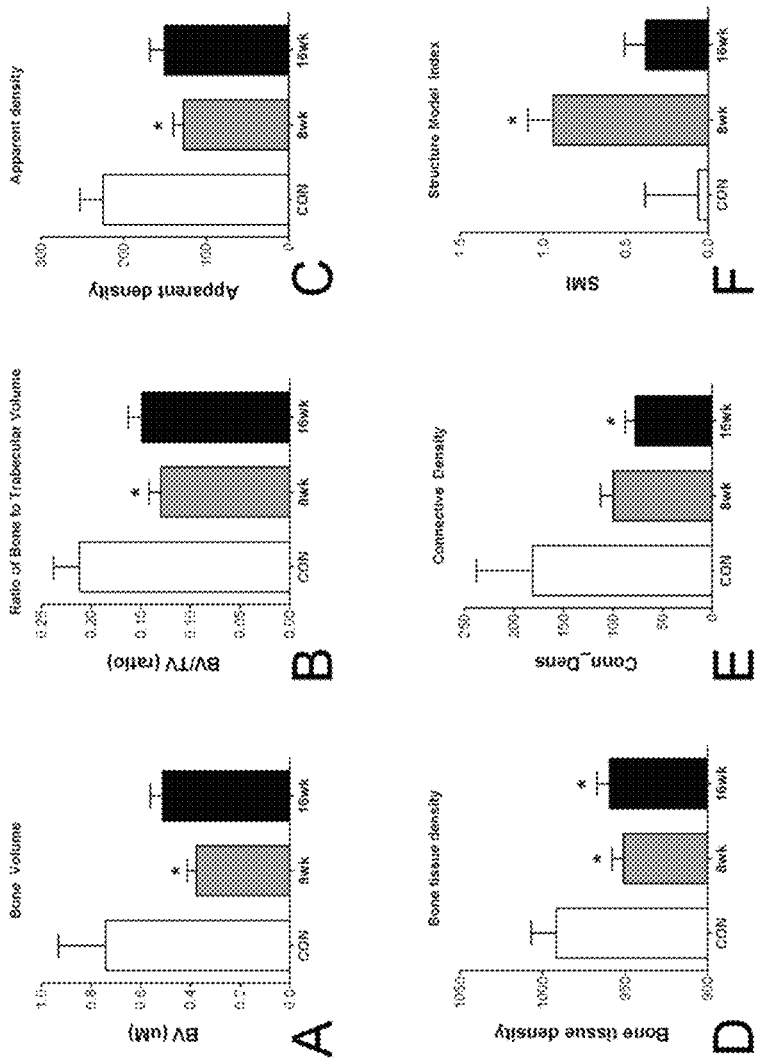
FIG. 19 shows trabecular bone changes in short-term and chronic hypergastrinemic animal models measured using microcomputed tomography (microCT). The bone volume (19A) and ratio of bone volume to trabecular volume (19B) were reduced in both short- and long-term hypergastrinemic animals, but this was more pronounced in short-term treated animals (50% vs. 30%). Two measures of density, the apparent density (19C) and tissue density (19D) were significantly reduced in both gastrin groups (~100%). The connectivity density (a measure of the number of trabeculae per unit volume) was significantly decreased (~60%) in the long-term hypergastrinemic group (19E). Short-term gastrin was associated with the conversion of bone from a more plate like structure (SMI close to 0) to a more rod-like structure (SMI increasing >1) (19F). This was not as apparent in long-term hypergastrinemic animals. These results demonstrate that gastrin significantly alters the bone phenotype in the Mastomys model. The alterations are consistent with an "osteoporotic" phenotype. BV=bone volume, TV=trabecular volume, ConnDens=connectivity density, SMI=structure model index (measure of rod:plate geometry). Mean±SEM, *p<0.05 vs. control animals. CON=control animals, 8 wk=short-term hypergastrinemia, 16 wk=long-term hypergastrinemia.

Bone Morphology and Dynamics:

Micro CT assessment was used to develop bone morphometric analyses (FIG. 19) of rodent femurs in hypergastrinemic animals. These demonstrated lower bone volumes and a decreased density and tensile strength. These data demonstrate that elevated gastrin levels stimulated bone resorption.

The structural model index (SMI) identified a shift in the ratio of plates/rods which demonstrates an alteration in femur geometry. Thus, gastrin increased the SMI indicating a change in the bone phenotype, through remodeling, toward a more rod-like formation. The latter is associated with weaker and stiffer bones and the bone fragility noted in osteoporotic women.

In contrast to normal Mastomys, chronic hypergastrinemic animals exhibited an osteo-arthritic phenotype with the following features: thickening of the epiphyseal plate, fragility of the bone (abnormal bone reconstitution due to increased adipocyte formation) and identification of abnormal immunogenic features.

Marrow was isolated from femurs and evaluated for osteoclastogenesis. Both osteoclasts and osteoblasts could be cultured at an abnormally early time-period compared to cells isolated from ovariectomized mice. This is evidence of activation of these two populations of cells in the hypergastrinemic model. This is consistent with the activation of a CCK2 receptor induced event.

In comparison to ovariectomized mice, hypergastrinemic Mastomys exhibit exaggerated morphological bone remodeling. The presence of an abnormal bone marrow phenotype was further confirmed by qPCR-based identification of pathway activation in the hypergastrinemic animals. This included down-regulation of ALOX5 and PTGS2 (inflammation), a down-regulation of PPARγ (adipocyte activation), and upregulated TNFSR11 (RANKL) (osteocyte activity). The PCR results are consistent, particularly the activation of osteocyte activity, with the macroscopic bone marrow alterations observed (epiphyseal growth, bone friability).

Figure 20:
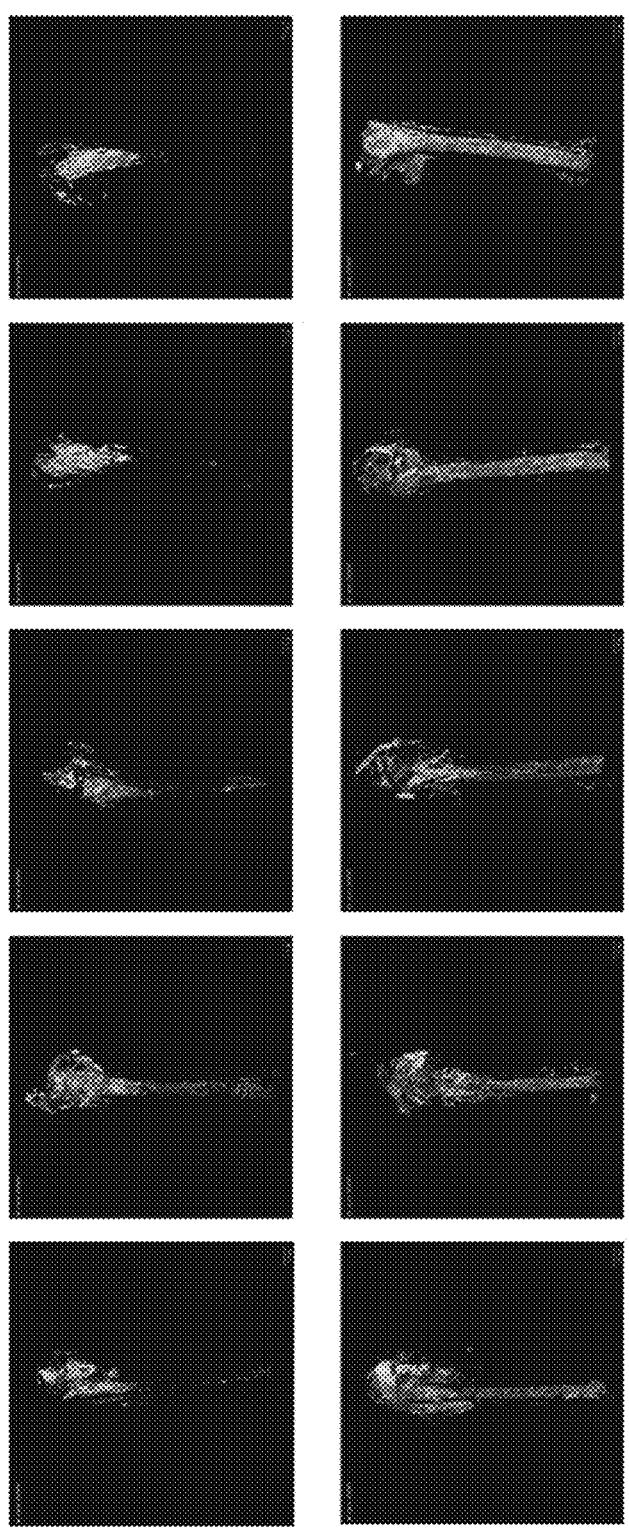
FIG. 20 is a series of photographs showing osmium-based staining for bone adipose tissue activation. Adipocytes take up osmium and are readily identified in bone. Control animals (right femur, n=5, top panel) predominantly exhibited osmium uptake in the tibial epiphysis. Short-term hypergastrinemic animals also exhibited osmium uptake in the epiphysis but significant uptake was also noted in the metaphysis (n=5, bottom panel). These results are consistent with a gastrin-activation of adipose tissue and an "aged" phenotype.

In order to further assess the bone marrow phenotype and evaluate whether bone adipose-tissue was activated (a measure of bone metabolism and integrity) an osmium-based staining protocol was used in age-sex matched controls and short-term hypergastrinemic animals. A significant increase in uptake was noted in treated animals (FIG. 20). This is consistent with an "aged" bone/osteoporotic phenotype.

These results confirm that short-term hypergastrinemia is associated with bone alterations that are similar to the morphological appearances identified with osteoporosis.

Figure 21:
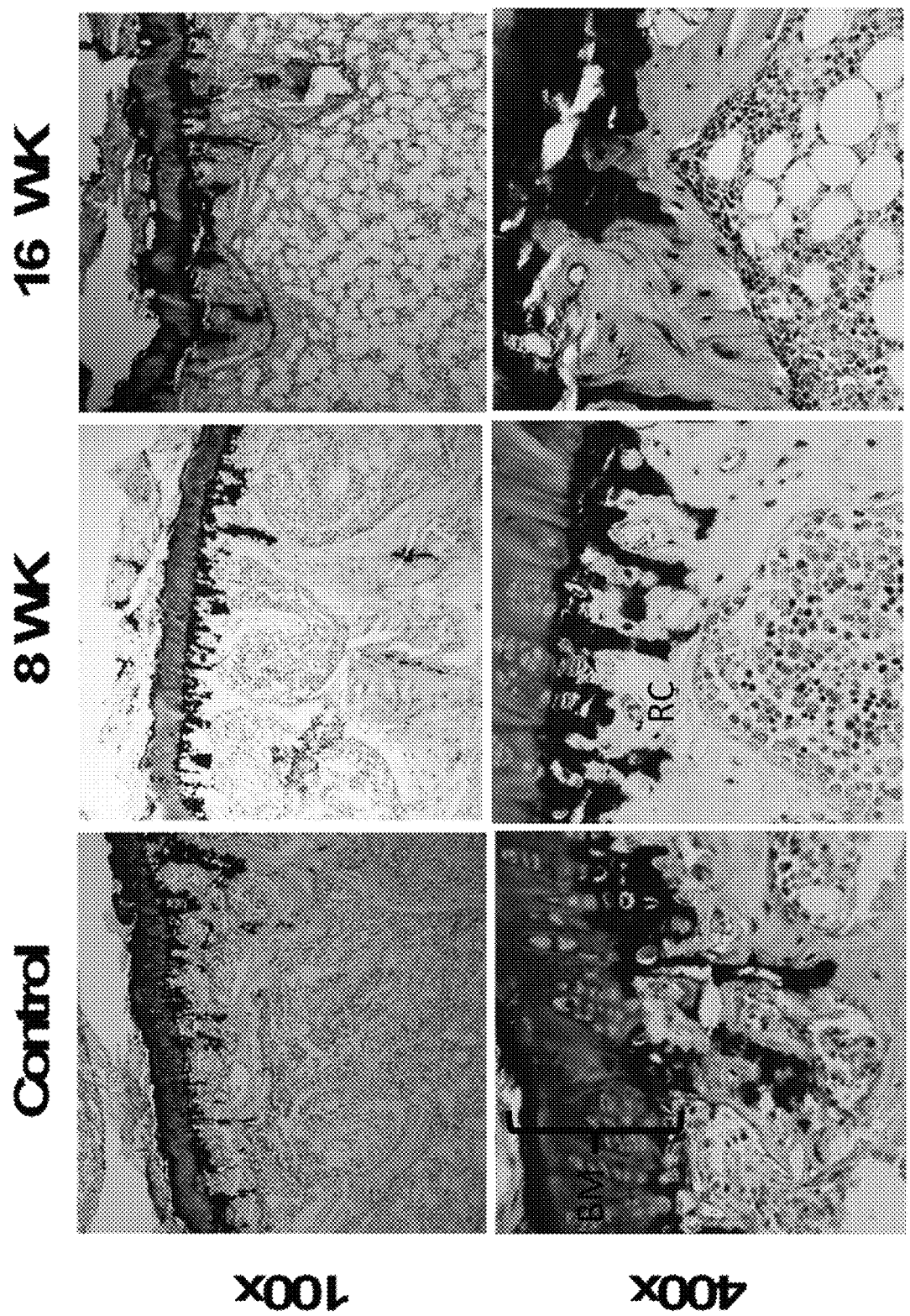
FIG. 21 is a series of photomicrographs showing toluidine-blue, TRAP-stained femurs from control, 8 week and 16 week loxtidine-treated Mastomys demonstrating patterns of bone mineralization and resorption cavities. In one aspect, the changes in loxtidine-treated animals reflect loss of bone mineralization and increased resorption—features consistent with osteoporotic phenotypes. BM=bone mineralization, RC=resorption cavity.
Figure 22:
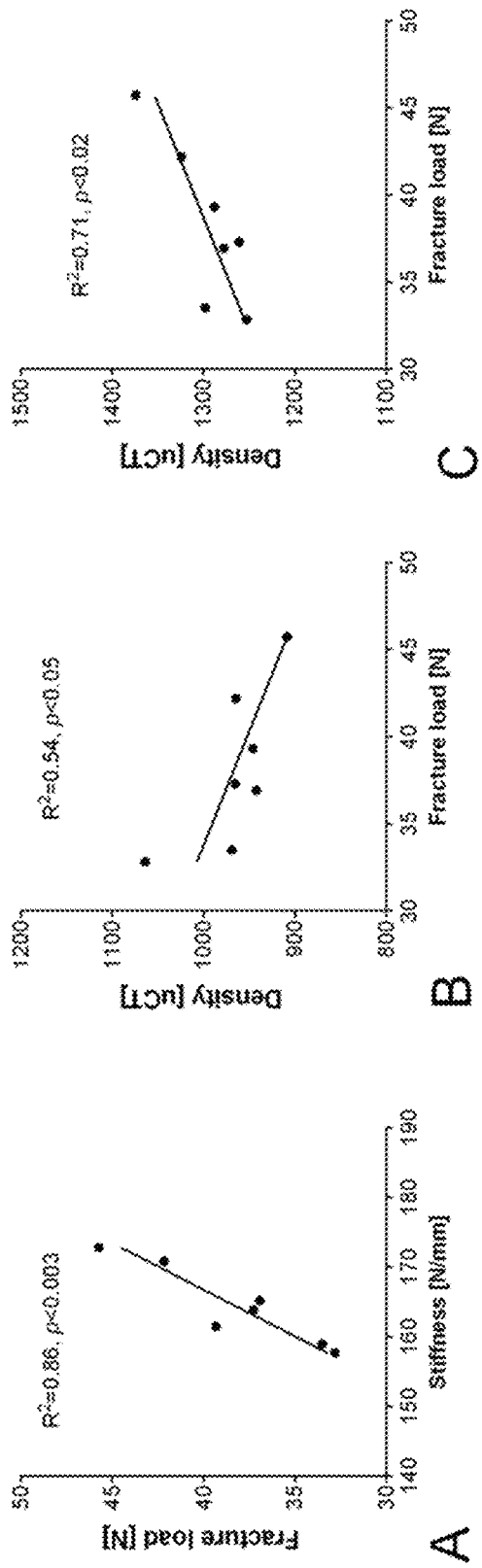
FIG. 22 is a series of graphs (22A-22C) showing a comparison between microCT and bone breaking in the Mastomys models. Femurs were loaded to failure (four-point bending) using a servohydraulic testing machine (Instron model 8874). A significant correlation ($R^2=0.86$, p<0.01) was noted between the stiffness of the bone and the fracture load (22A) demonstrating that increasing bone stiffness would require a greater fracture load. We assessed the relationship between bone-bending and microCT measures for both trabecular and cortical density. These identified that the trabecular density was inversely correlated ($R^2=-0.54$) to the force required to fracture bone (22B), while increasing cortical density was related to higher fracture loads ($R^2=0.71$, 22C). These results demonstrate that the mechanical force required to break bone relates to bone structure and density and that a combination of these two approaches provides physiologically relevant information in this model. N=7 animals, uCT=microCT.

Thereafter, bone histomorphometry was examined. These studies identified decreased bone mineralization with an increased resorption cavities as well as significantly increased (p<0.05) numbers of TRAP-positive osteoclasts (15±6 p<0.05 and 16±4.5 p<0.05, vs 9±3 in controls) in the 8-week and 16-week treated Mastomys. Evidence of osteoid seams and osteomalacia was also noted (FIG. 21).

Finally, bone strength was examined in Mastomys using an Instron device. Femurs were loaded to failure in four-point bending. Tests were conducted with a deflection rate of 0.05 mm/sec using a servohydraulic testing machine (Instron model 8874; Instron Corp., Norwood, Mass., USA).

Finally, bone strength was examined in Mastomys using an Instron device. Femurs were loaded to failure in four-point bending. Tests were conducted with a deflection rate of 0.05 mm/sec using a servohydraulic testing machine (Instron model 8874; Instron Corp., Norwood, Mass., USA).

The stiffness ranged from 158-173 N/mm. The maximum load required to fracture the bone ranged from 32.8-45.7 N/mm. These values were strongly correlated with each other (FIG. 17A, $R^2=0.86$, p<0.003, linear regression analysis).

Comparisons of bone density (micro CT) and the fracture force identified correlations for both trabecular ($R^2=0.54$, 22B) and cortical ($R^2=0.71$, 22C) bones.

Thus, measurements of bone strength using the Instron device provide additional information consistent with the development of an abnormal and fragile bone phenotype during hypergastrinemia. These mechanical data support the evidence for the biological basis of a gastrin-driven "osteoporotic" phenotype in the hypergastrinemic model.

Summary (FIG. 23, 24): Short-term hypergastrinemia (8 weeks) causes demonstrable and measurable osteoporotic changes in the femur. In the gastric antrum, short term hypergastrinemia was associated with active G cell (transcript), increased PTH1R and decreased estrogen responsiveness (ERα/β and AR) with no change in CaSR expression. The bone-analysis observations are analogous to those evident in the human post-menopausal condition.

Figure 17:
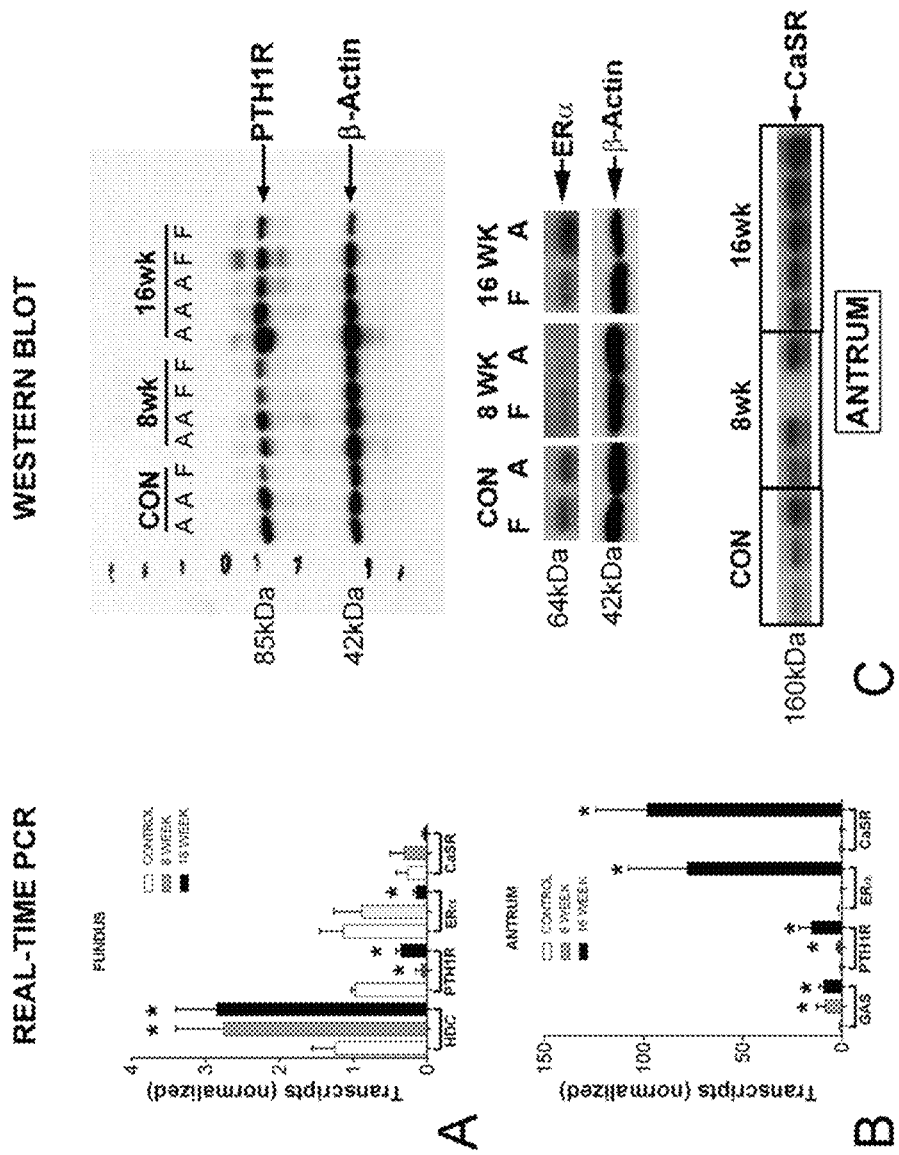
FIG. 17 is a pair of graphs (17A and 17B) and photographs (17C) showing the expression of calcium axis-related receptors, PTH1R, ERα and CaSR in the stomach of the Mastomys models. PCR and western blot results of gastric mucosa from normal (n=4) compared to animals treated with loxtidine for 8 (n=4) and 16 (n=5) weeks, respectively. In the fundus, both short (8 wk) and long (16 wk)-term hypergastrinemia significantly increased HDC but decreased PTH1R and ERα expression respectively (17A). In the antrum, hypergastrinemia was associated with significant increases in gastrin transcripts as well as in elevations in PTH1R, ERα and CaSR expression (17B). These effects were more pronounced in long-term hypergastrinemia. The RNA effects were recapitulated at a protein level (Western blot—17C). Specifically, PTH1R expression was decreased in the fundus (F) but increased in the antrum (A)—top panel. Antral ERα expression was elevated at 16 weeks (center panel) as was CaSR (bottom panel). These results demonstrate that the fundus and antrum respond to short- and long-term hypergastrinemia with differential synthesis and expression of receptors related to the calcium:bone axis. Specifically, functional receptors are down-regulated in the histamine synthesizing portion of the stomach (fundus) but these are increased in the gastrin-secreting (antral) stomach. In some aspects, this reflects sensitization of the antrum and the calcium-sensing G cells. Mean±SEM, *p<0.05 vs. control (untreated) animals. CON=control animals, 8 wk=short-term hypergastrinemia, 16 wk=long-term hypergastrinemia.

Extending hypergastrinemia to 16 weeks (chronic model) resulted in measurable osteoporotic changes in the femur and was associated with an increased antral CaSR and ERα as well as PTH1R expression (FIG. 17).

The combination of elevated circulating gastrin and increased PTH1R expression on G-cells was the consistent feature associated with an osteoporotic phenotype.

These results indicate that the hypergastrinemic Mastomys is suitable model for evaluating the effects of gastrin on bone pathophysiology and demonstrate the significant pro-osteoporotic effects of hypergastrinemia on bone.

Example 6: Effects of Acid Blockade on Bone Dynamics in Ovariectomized Mastomys

Ovariectomy is a standard procedure to generate a "post-menopausal" phenotype for bone studies. Since estrogen exhibits an G-cell regulatory effect (see FIG. 6), it next was evaluated the specific role of estrogen loss on the bone phenotype in untreated animals, in ovariectomized animals as well as in ovariectomized animals with short term (8 weeks) and long term (16 weeks) hypergastrinemia. Bilateral ovariectomy (OVX) and tubal ligation was performed using a posterior approach in the Mastomys. Animals were studied after 8 weeks.

Figure 25:
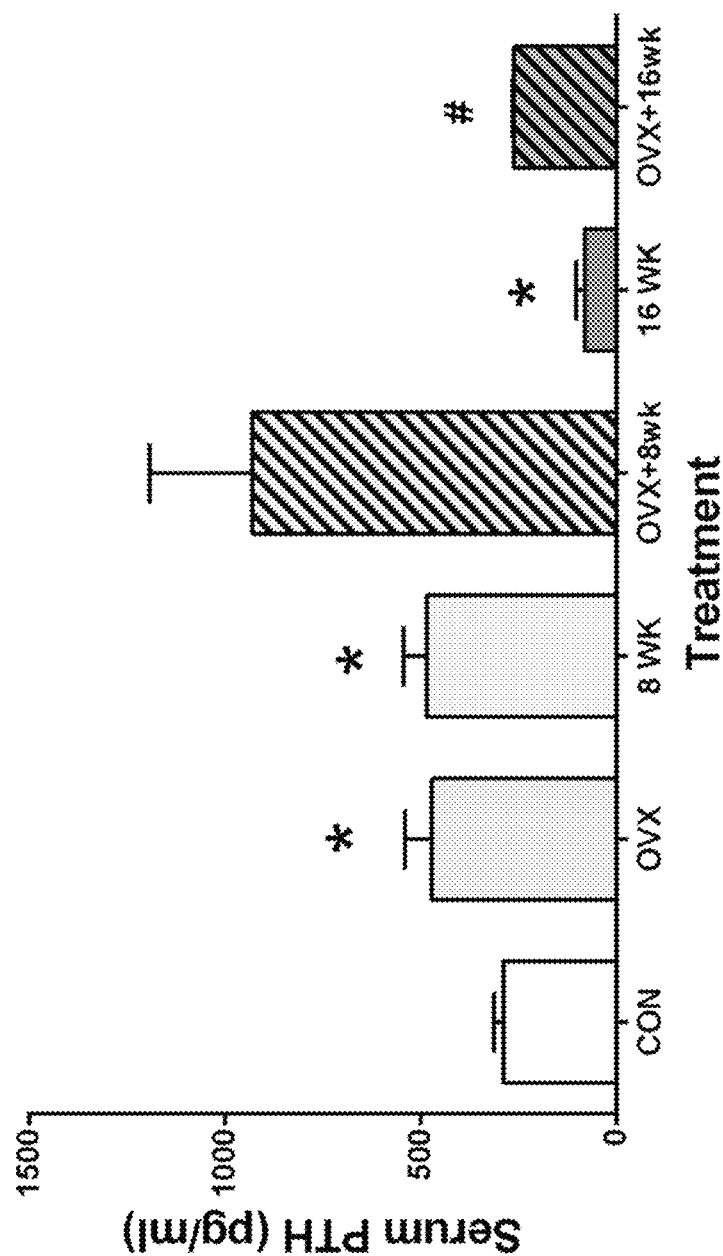
FIG. 25 is a graph showing the effects of ovariectomy on short-term and chronic hypergastrinemia-mediated circulating PTH levels in the Mastomys model. Ovariectomy increased PTH levels ~100%. Short-term hypergastrinemia similarly elevated PTH levels. This was increased (300% above control) in the OVX/8 week treated animals. Long-term gastrin treatment significantly reduced levels by ~60%. Ovariectomy reversed this, normalizing PTH levels. These results confirm ovariectomy-mediated activation of PTH release (consistent with loss of estrogen) and that this is amplified by short-term hypergastrinemia in an in vivo model. Long-term hypergastrinemia appears to reduce PTH release, an effect that is also seen in ovariectomized animals. The mechanism may reflect down-regulation of the CCK2 receptor or its signaling responses in the PTH gland exposed to long-term gastrin stimulation. Such an effect overrides the loss of estrogen, indicating gastrin may play a role in PTH gland function. Mean±SEM, *$p<0.05$ vs. control animals, # $p<0.05$ vs. OVX alone. CON=control animals, OVX=ovariectomized animals, 8 wk=short-term hypergastrinemia, 16 wk=long-term hypergastrinemia.

Circulating Hormones:

After 8 weeks, estrogen was reduced by ovariectomy. Serum PTH, however, increased ~2-fold (FIG. 25).

Figure 26:
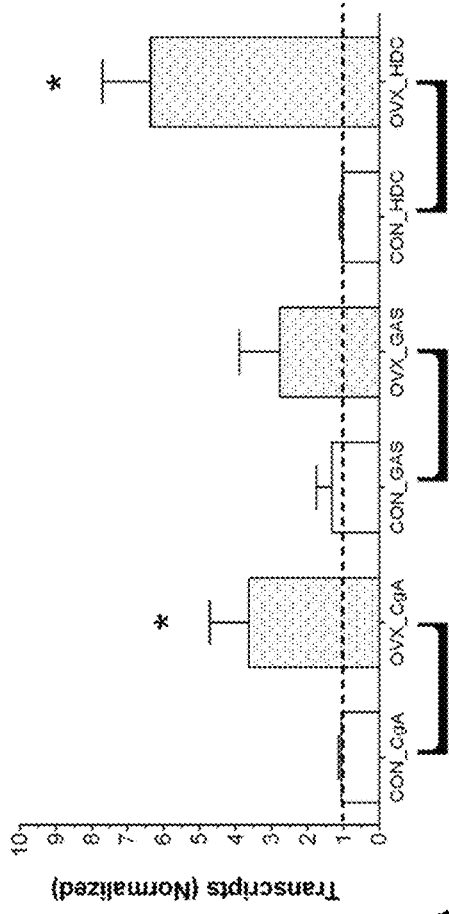
FIG. 26 is a series of graphs (26A-26D) showing the expression of neuroendocrine-related transcripts in the stomach of normo- and hypergastrinemic Mastomys ovariectomy models. PCR results of gastric mucosa from normal (n=11) compared to ovariectomized (OVX; n=8) Mastomys (TOP) and between OVX and short-term (n=4) and long-term (n=4) hypergastrinemic OVX-animals (BOTTOM). Ovariectomy significantly increased gastric mucosal CgA (4-fold) and HDC (~6-fold) expression (26A). Neither short- nor long-term hypergastrinemia had any additional effect on OVX-mediated CgA synthesis (2.8-4.2-fold compared to 4.3-fold) (26B). Short-term hypergastrinemia elevated gastrin expression (~40-fold—26C) and HDC (~40—fold-26D). Long-term hypergastrinemia elevated both gastrin as well as HDC, but the effect was most pronounced for ECL cell-derived HDC expression (~45-fold—26D). These results confirm the estrogen regulates ECL cell transcription of HDC (and thereby histamine synthesis) and that gastrin synthesis is similarly regulated by estrogen. Circulating gastrin further up-regulates expression. Mean±SEM, *$p<0.05$ vs. non-ovariectomized animals. # $p<0.05$ vs. OVX. CON=control animals, OVX=ovariectomized animals, 8 wk=short-term hypergastrinemia, 16 wk=long-term hypergastrinemia.
Figure 26:
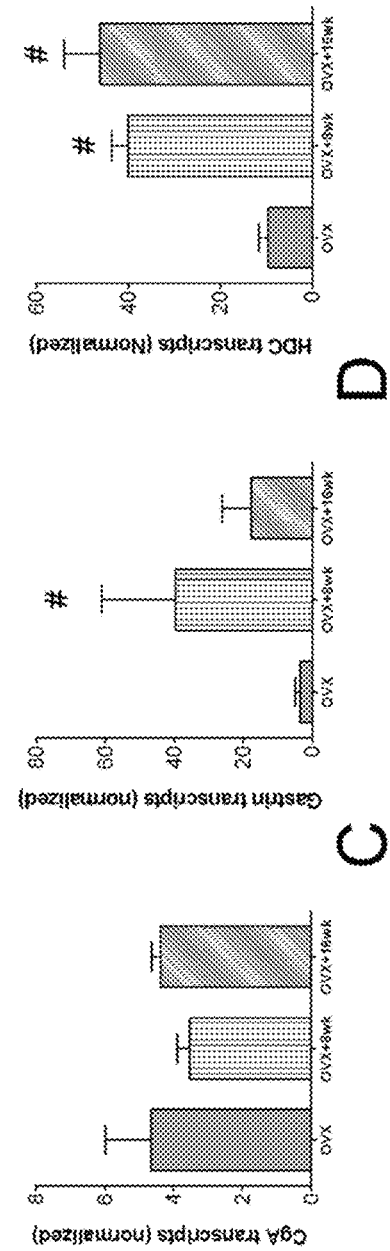

The Stomach:

Ovariectomy was associated with a significant increase in chromogranin A (CgA) and HDC transcription, but gastrin expression was not altered (FIG. 26). This demonstrates that one effect of estrogen in the stomach is to down regulate ECL cell histamine synthesis.

Figure 27:
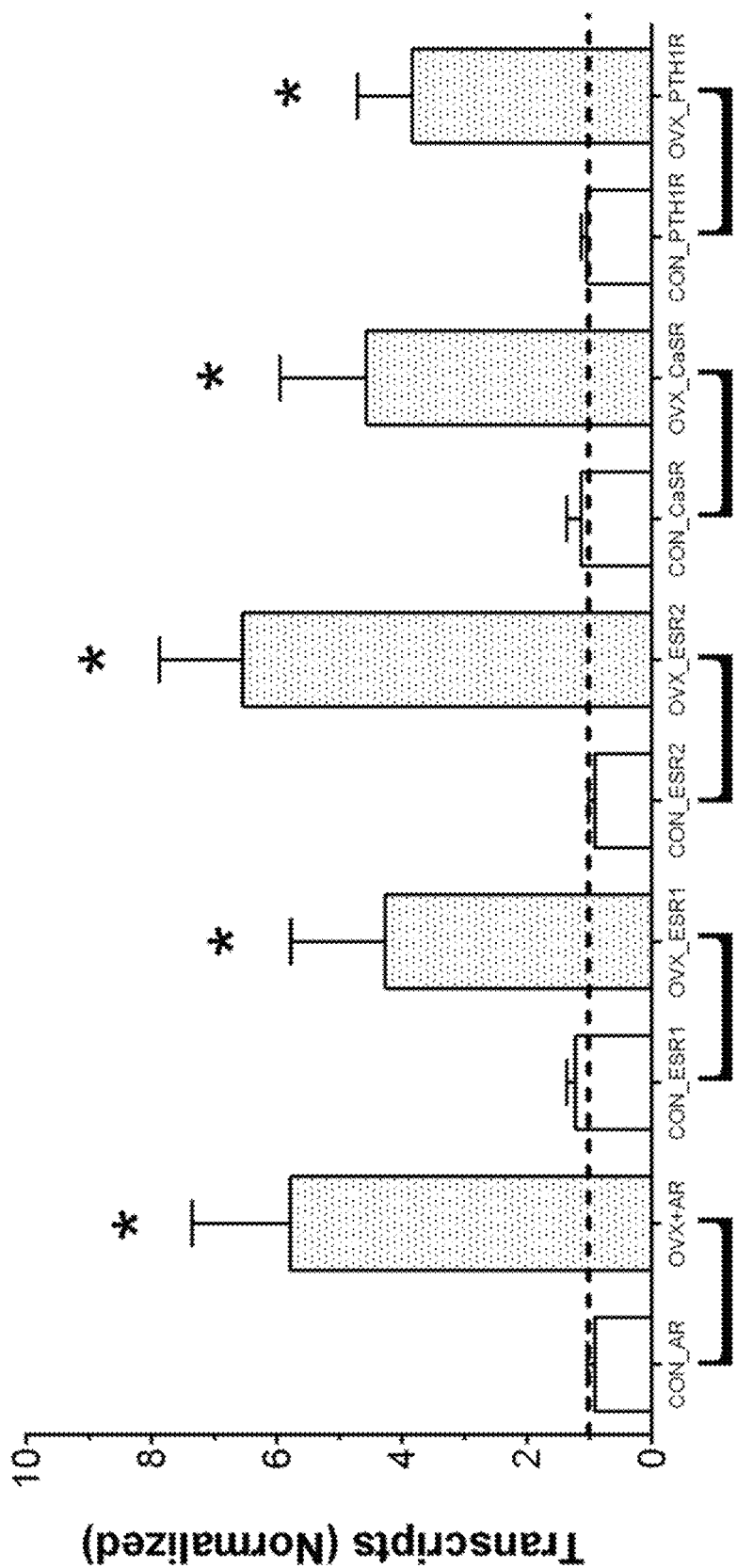
FIG. 27 is a graph showing the expression of calcium axis-related receptors, PTH1R, ERα and CaSR in the stomach of the normo-gastrinemic Mastomys ovariectomy model. PCR results of gastric mucosa from normal compared to ovariectomized (OVX) Mastomys. Ovariectomy increased gastric mucosal expression of the androgen receptor (~6-fold) as well as both estrogen receptors (ESR1 and ESR2, both ~4-fold). CaSR and PTH1R were also increased by loss of estrogen (5- and 4-fold, respectively). These results confirm that loss of estrogen is associated with up-regulation of transcripts related to calcium sensing and the parathyroid:ovarian axis. Circulating gastrin further up-regulates expression. Mean±SEM, *$p<0.05$ vs. non-ovariectomized animals. CON=sham-operated control animals (n=11), OVX=ovariectomy (n=8). AR=androgen receptor, ESR=estrogen receptor, CaSR=calcium sensing receptor, PTH1R=parathyroid type 1 receptor.

Ovariectomy increased gastric mucosal transcription of androgen (6-fold) and estrogen receptors (both ESRα/β: 4-7-fold) as well as CaSR (5-fold) and PTH1R (4-fold) (FIG. 27). Thus, removal of estrogen resulted in detectable alterations in gastric cell receptors involved in sensing and responding to dietary calcium i.e., CaSR and the parathyroid axis (PTH1R).

Figure 28:
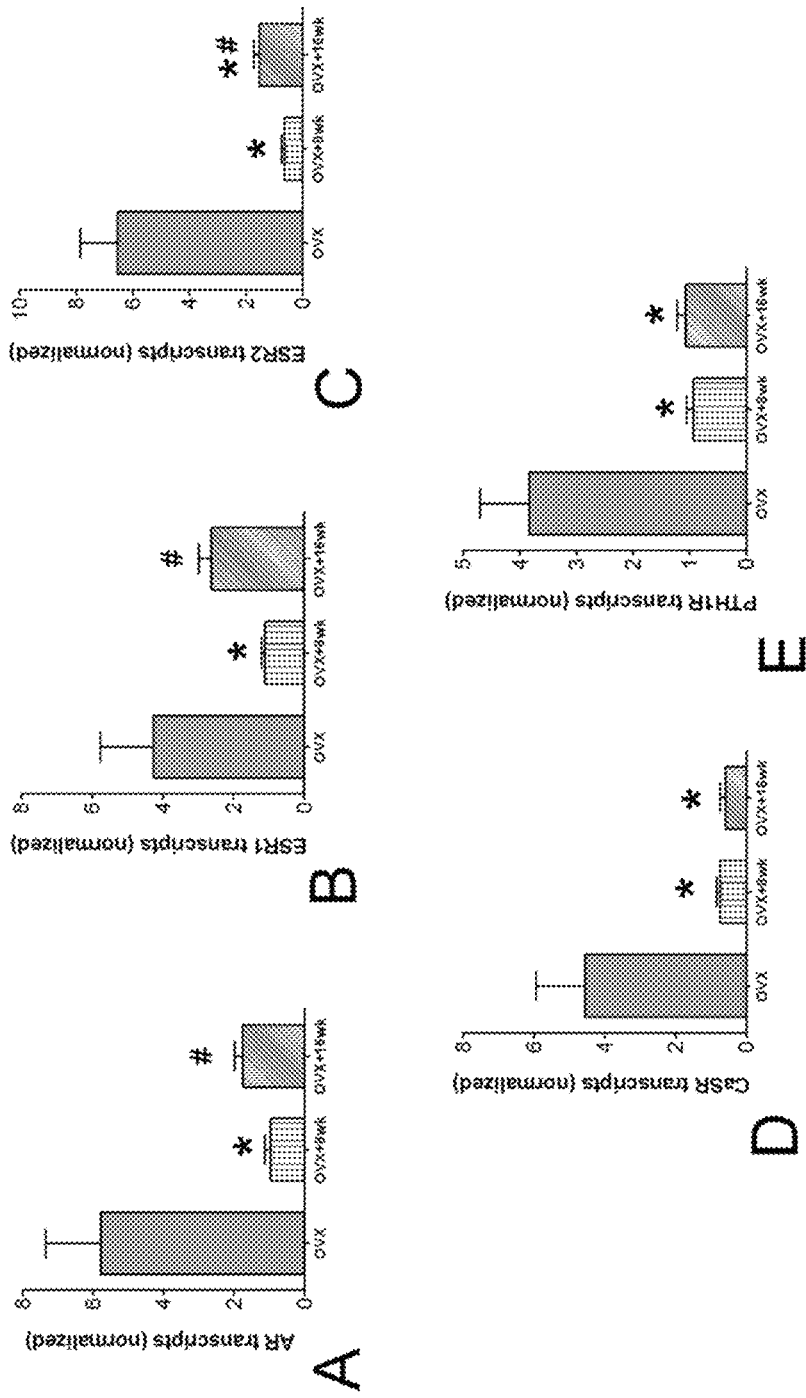
FIG. 28 is a series of graphs (28A-E) showing the expression of calcium axis-related receptors, PTH1R, AR, ERα and CaSR in the stomach of the hypergastrinemic Mastomys ovariectomy models. PCR results of gastric mucosa from OVX and short-term (n=4) and long-term (n=4) hypergastrinemic OVX-animals. Ovariectomy-induced elevations in androgen receptors was normalized in both short-term and long-term hypergastrinemic animals, an effect more pronounced in short-term animals (28A). A similar result was noted for both estrogen receptors (28B, C). Both CaSR (28D) and PTH1R (28E) were significantly reduced by hypergastrinemia. These results identify that expression of receptors related to the calcium:bone axis that are up-regulated by ovariectomy in the gastric mucosa are "normalized" by both short- and long-term hypergastrinemia. This reflects a physiological attempt to regulate or recalibrate calcium-sensing in a high-gastrin milieu. Mean±SEM, *$p<0.05$ vs. ovariectomized animals, # $p<0.05$ vs. short-term hypergastrinemic animals. CON=control animals, OVX=ovariectomized animals, 8 wk=short-term hypergastrinemia, 16 wk=long-term hypergastrinemia. AR=androgen receptor, ESR=estrogen receptor, CaSR=calcium sensing receptor, PTH1R=parathyroid type 1 receptor.

Short-Term Hypergastrinemia/OVX Model:

Short-term hypergastrinemia in the ovariectomy model increased circulating PTH (FIG. 25). In the stomach, both gastrin and HDC transcripts were elevated by a combination of acid suppression (8 weeks Loxtidine) and OVX (FIG. 26B-D). The increased expression of receptors viz. AR/ESRα/β, CaSR and PTH1R that occurred following OVX (viz. FIG. 27) was not identified in hypergastrinemic animals. Levels were reduced and were no longer different to control (FIG. 28). This indicates that pharmacological suppression of acid secretion (with rises in gastric pH and gastrin) normalizes gastric expression of receptors involved in calcium sensing even when estrogen was removed.

Figure 30:
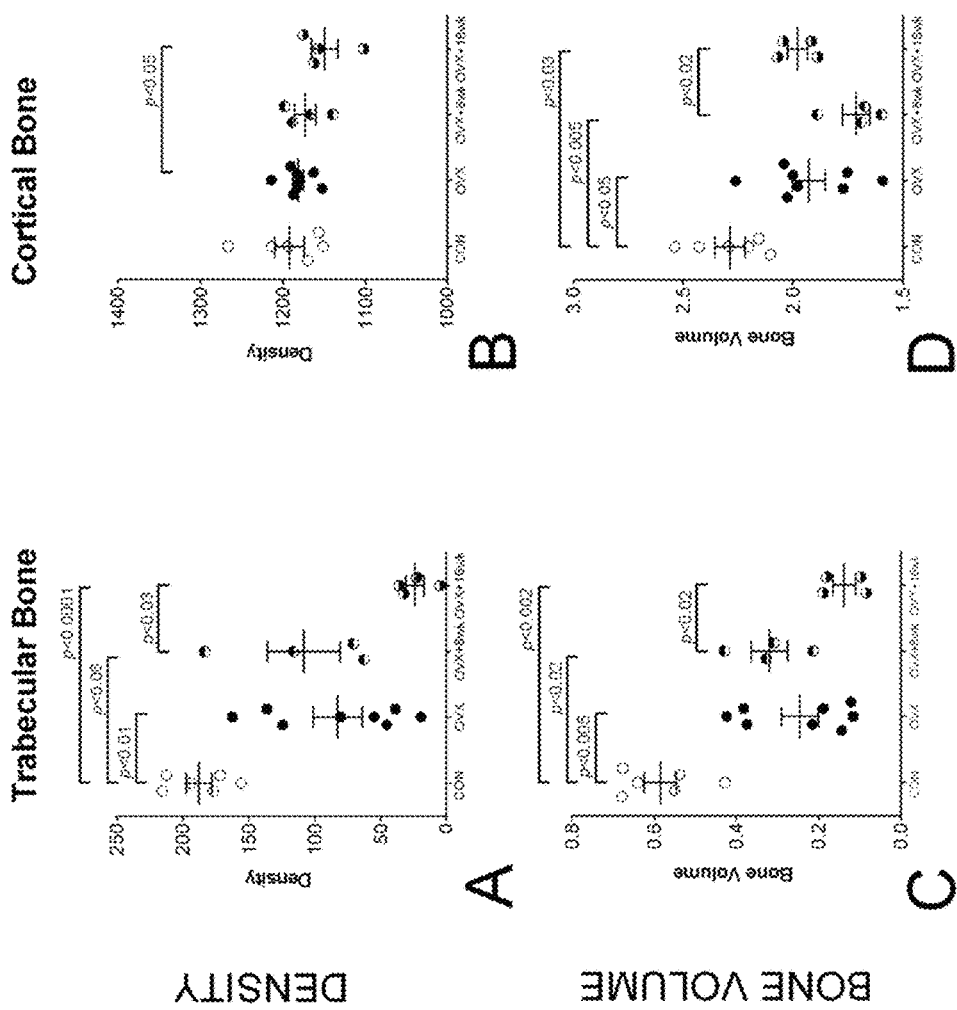
FIG. 30 is a series of graphs (30A-D) showing MicroCT measurements in trabecular and cortical bone in the normo- and hypergastrinemic Mastomys ovariectomy models. Trabecular density was significantly decreased by ovariectomy (~50%) compared to normal animals (30A). This was amplified by long-term hypergastrinemia (85%). Trabecular volume was also significantly decreased by ovariectomy (~50%) (30B). This was amplified by long-term hypergastrinemia (~70%). Cortical bone density was not decreased by ovariectomy, but was significantly lower in the long-term hypergastrinemic animals (~5%, 30C). Cortical volume was significantly decreased by ovariectomy (~30%) (30D). This was amplified by short-term hypergastrinemia (~30%). These results demonstrate that gastrin amplifies bone loss in the ovariectomy model and results in microCT features consistent with an osteoporotic phenotype. The effects of long-term hypergastrinemia are reflected principally in trabecular alterations. CON=control animals, OVX=ovariectomized animals, 8 wk=short-term hypergastrinemia, 16 wk=long-term hypergastrinemia.

Long-Term Hypergastrinemia/OVX Model:

16 week-hypergastrinemia was associated with normalization of plasma PTH levels (FIG. 30). In the stomach, HDC was elevated (FIG. 26). Levels of AR/ESRα/, CaSR and PTH1R in 16 week treated animals were not different to control (FIG. 28). Gastric expression of receptors involved in calcium sensing in the long-term model, as in the short-term model were normal during estrogen removal.

Figure 29:
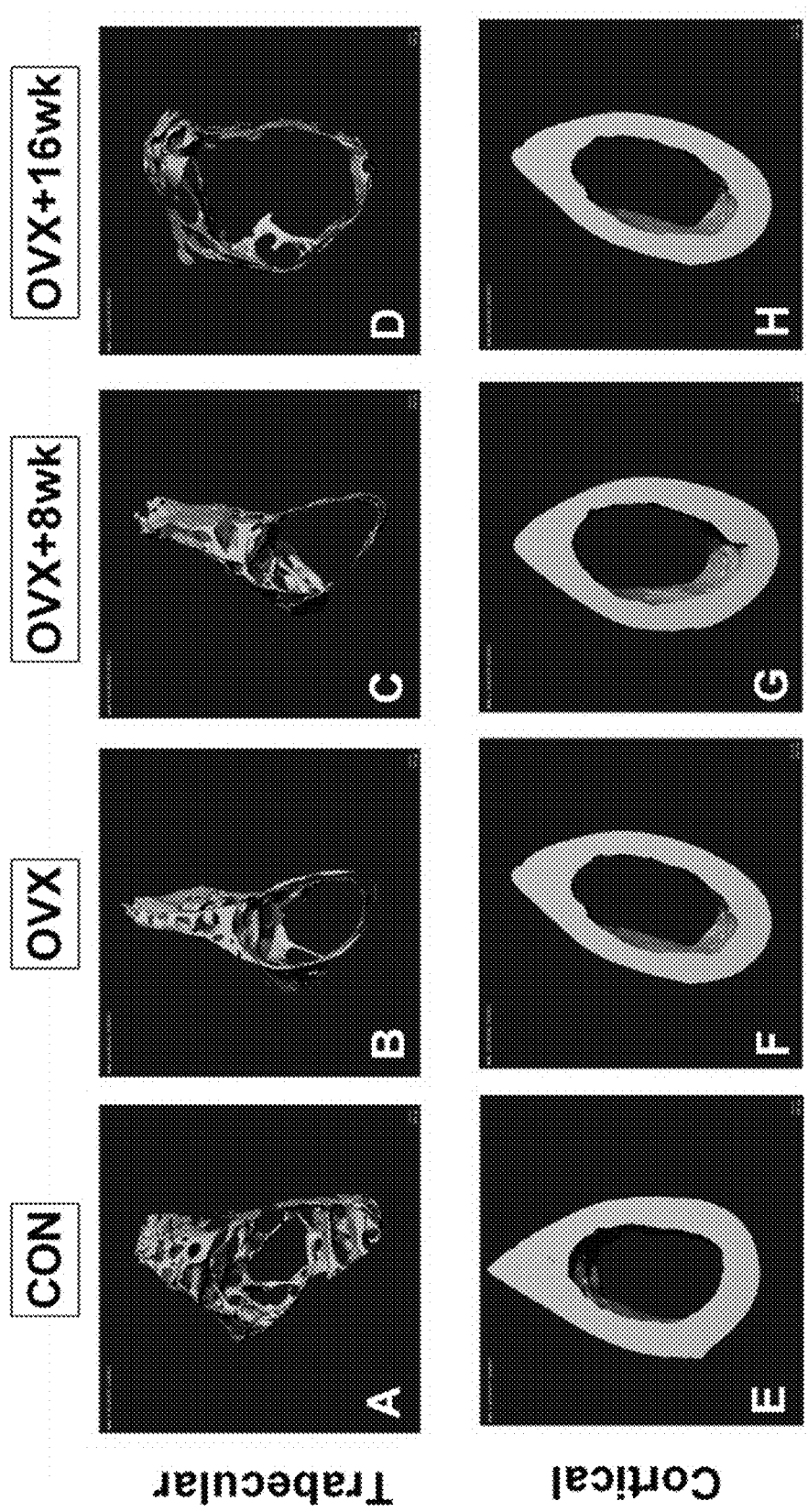
FIG. 29 is a series of screenshots (29A-H) showing microcomputed tomography (microCT) features of trabecular and cortical bone. Trabecular bone from ovariectomized animals exhibited significant loss (29B) compared to control bone (29A). Both short-term (29C) and long-term (29D) hypergastrinemia reduced this—the effects were more evident in long-term hypergastrinemic animals. In the cortical bone, ovariectomy was associated with images of trabecular and cortical bone from normal, ovariectomized (OVX) and OVX-animals treated with loxtidine for 8 and 16 weeks, respectively. Bone loss, particularly in the trabecular region of the femur is noted following OVX. This can in some aspects be increased by gastrin elevations. CON=control animals, OVX=ovariectomized animals, 8 wk=short-term hypergastrinemia, 16 wk=long-term hypergastrinemia.

Bone Morphology and Dynamics in the OVX and Hypergastrinemic OVX Model:

Micro CT Analyses:

Trabecular topography is represented in FIG. 29. Bone measurements identified that density and volume were decreased ~50% following ovariectomy. This is consistent with previous reports in rodent ovariectomy models (FIG. 30A, C). Gastrin-mediated reductions were most significant ($p<0.005$) in long-term hypergastrinemic animals (80-85% decreased). The latter animals also exhibited decreases (~5%, $p<0.05$) in cortical density (FIG. 30B). Cortical bone volume was decreased in all OVX animals (~15%) but most significantly ($p<0.005$, ~30%) in the short-term hypergastrinemic animals (FIG. 30D).

Further measurements of the cortical bone identified significant decreases in the endosteum and periosteum. OVX decreased both the radius (20%) and circumference (18%) (FIG. 31A-D). More significant reductions were identified in short-term hypergastrinemic animals (radius: 25-30%; circumference 27%). These were less than decreases measured during OVX alone ($p<0.02$). Measurements in long-term hypergastrinemic animals were not different to OVX alone.

These results identify that elevated circulating gastrin levels amplify estrogen-loss mediated bone changes. The most significant effects of short-term hypergastrinemia were at the level of the cortical bone and the endosteum/periosteum, while long-term hypergastrinemic effects were predominant in the trabecular bone, identifying a role for the latter also in the regulation of bone metabolism and strength. To assess the latter, strength testing studies were performed.

Figure 32:
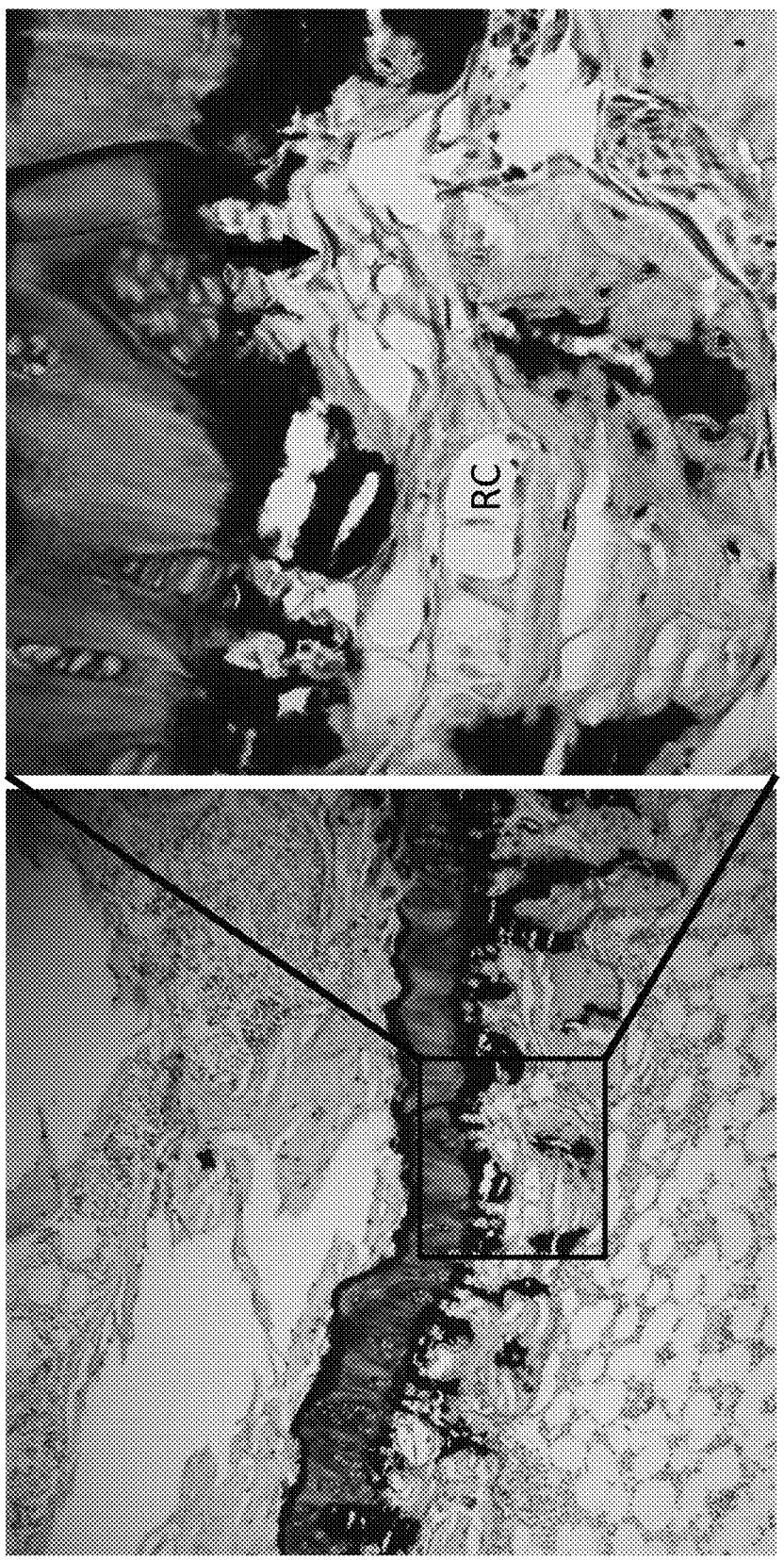
FIG. 32 is a pair of photomicrographs showing Toluidine-blue, TRAP-stained femurs from ovariectomized Mastomys identifying patterns of bone mineralization and resorption cavities as well as the number and position of osteoclast cells. TRAP staining is indicated by red cells; osteoclasts are the red-stained multinuclear cells (yellow arrow). Left panel (100× mag), Right panel (400× mag). RC=resorption cavity.

Bone Histomorphometry:

Ovariectomy was associated with a decreased bone mineralization with an increased resorption cavities as well as significantly increased ($p<0.05$) numbers of TRAP-positive osteoclasts (26.8±11 vs 9±3 in controls, $p<0.05$) (FIG. 32).

Figure 31:
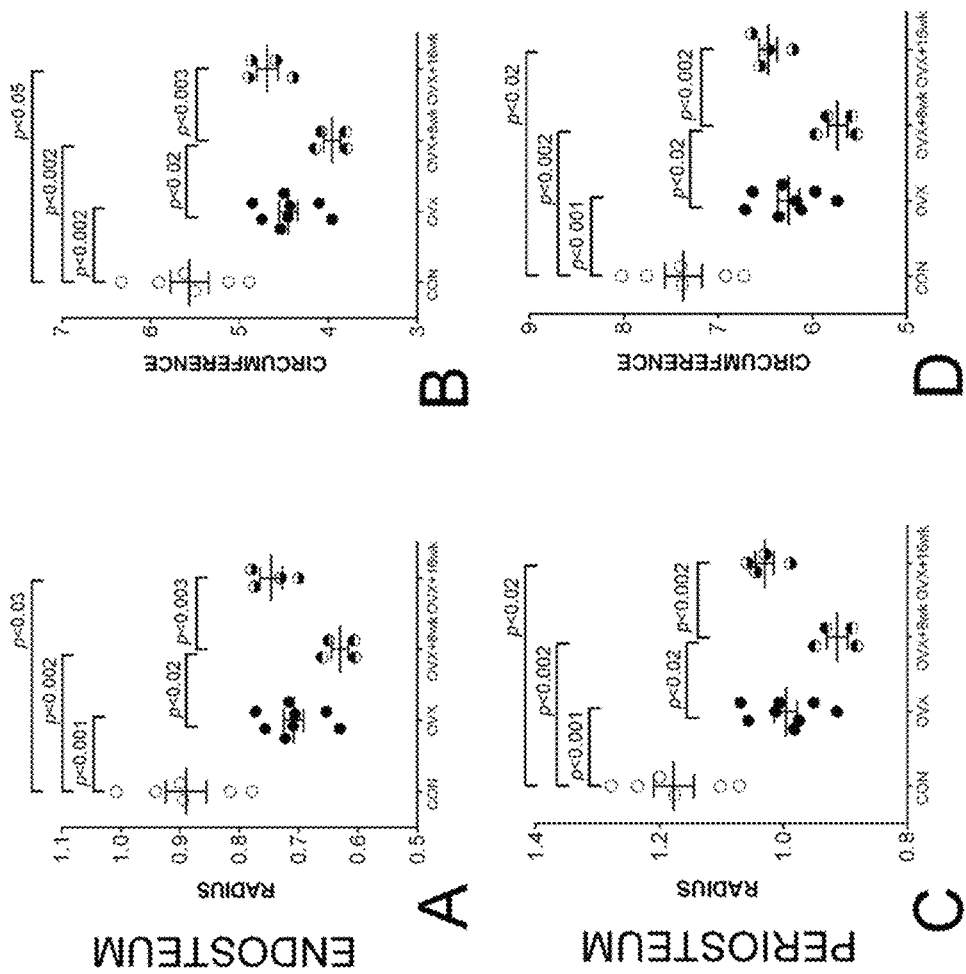
FIG. 31 is a series of graphs (31A-D) showing MicroCT measurements of endosteal and periosteal dimensions in cortical bone in the normo- and hypergastrinemic Mastomys ovariectomy models. The endosteal radius was significantly decreased by ovariectomy (~20%) compared to normal animals (31A). This was significantly amplified by short-term hypergastrinemia (30%). The endosteal circumference was also significantly decreased by ovariectomy (~18%) (31B). This was significantly amplified by short-term hypergastrinemia (~27%). The periosteal radius, likewise was reduced in ovariectomized animals (~20%, 31C), an effect significantly amplified by short-term hypergastrinemia (~30%). The periosteal circumference was also reduced by ovariectomy (~20%), an effect amplified by short-term hypergastrinemia (~30%) (31D). These results demonstrate that gastrin amplifies cortical bone dimensions, effects principally accentuated by short-term hypergastrinemia. CON=control animals, OVX=ovariectomized animals, 8 wk=short-term hypergastrinemia, 16 wk=long-term hypergastrinemia.
Figure 33:
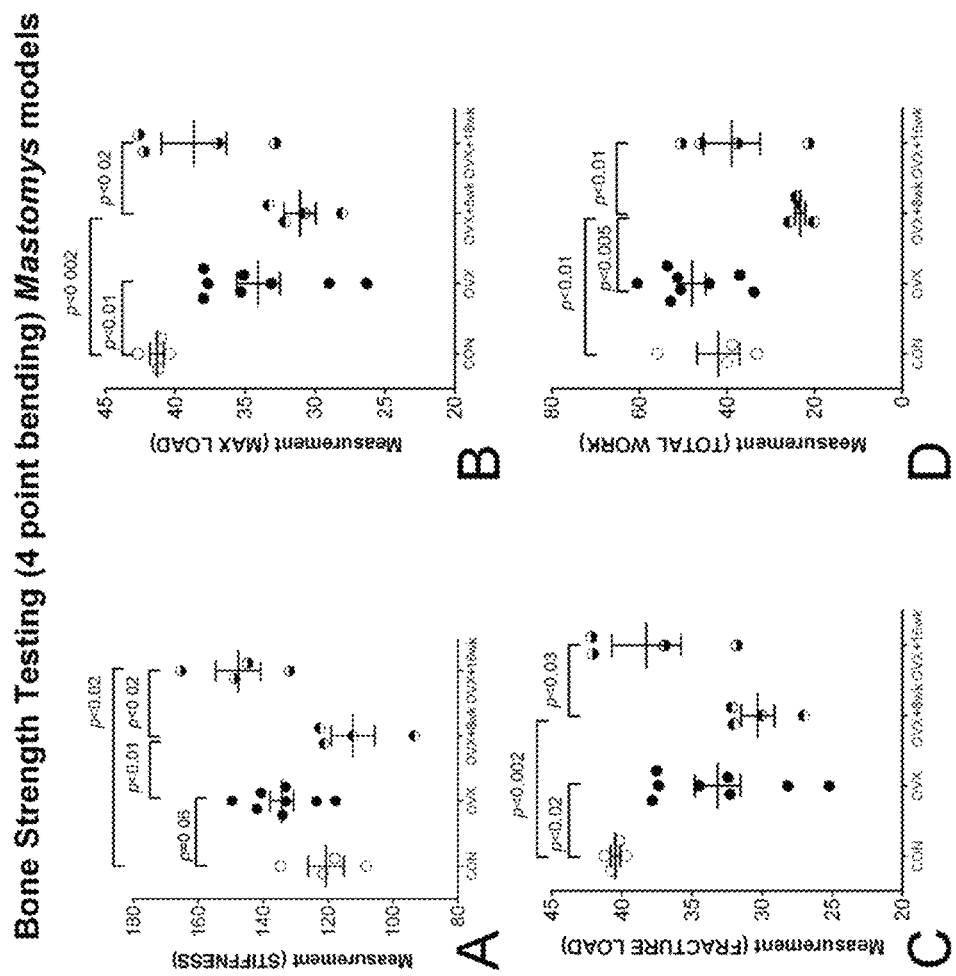
FIG. 33 is a series of graphs (33A-D) showing Instron 4-point bending results of femurs from normo- and hypergastrinemic Mastomys ovariectomy models. Stiffness was increased by ovariectomy (~15%), an effect that was significantly amplified by long-term hypergastrinemia (33A). Short-term hypergastrinemia was associated with a reduction in stiffness to normal levels. The maximum load to fracture the bone was significantly lower in the ovariectomized animals (~20%~33B). Hypergastrinemia did no alter this, but long-term hypergastrinemic animals required a greater load to fracture bone compared to short-term animals. The fracture load was similarly decreased in ovariectomized animals (~25%) and was not altered by gastrin (33C). Long-term hypergastrinemic animals, did however, require a higher load to fracture than short-term hypergastrinemic animals. The total work required to fracture bone was increased in ovariectomized animals (~20%) (33D). While long-term hypergastrinemia did not alter work, bones from short-term hypergastrinemic animals required ~50% less work to fracture. These results demonstrate that the strength of bones following ovariectomy is differentially affected by short-term gastrin (resulting in weak bones) and long-term gastrin (stiff bones). CON=control animals, OVX=ovariectomized animals, 8 wk=short-term hypergastrinemia, 16 wk=long-term hypergastrinemia.

Bone Mechanical Strength Testing:

Four-point bending analysis of the femur identified an increase in stiffness in OVX animals (FIG. 33A). OVX also decreased both the maximal load and fracture load (FIG. 33B, C). This indicates that estrogen loss, per se, decreased the strength of the bone (a cortical effect) while increasing its stiffness (a trabecular effect related to alterations in rod/plates). Short-term hypergastrinemia decreased the amount of work required to fracture bone (FIG. 33D). These parameters represent an effect consistent with weak, damaged cortical bone (FIG. 30-31). The OVX-generated bone stiffness was reversed by short-term hypergastrinemia suggesting that these gastrin effects are limited to activation and resorption phases of bone remodeling. Long-term hypergastrinemia reversed the load and work required to fracture the bone. However, bone stiffness was increased in these animals consistent with trabecular alterations (FIG. 30). This is consistent with a bone remodeling phenotype that includes the reversal and formation phases of bone formation but is abnormal in that the bone is stiff and therefore weak.

Figure 34:
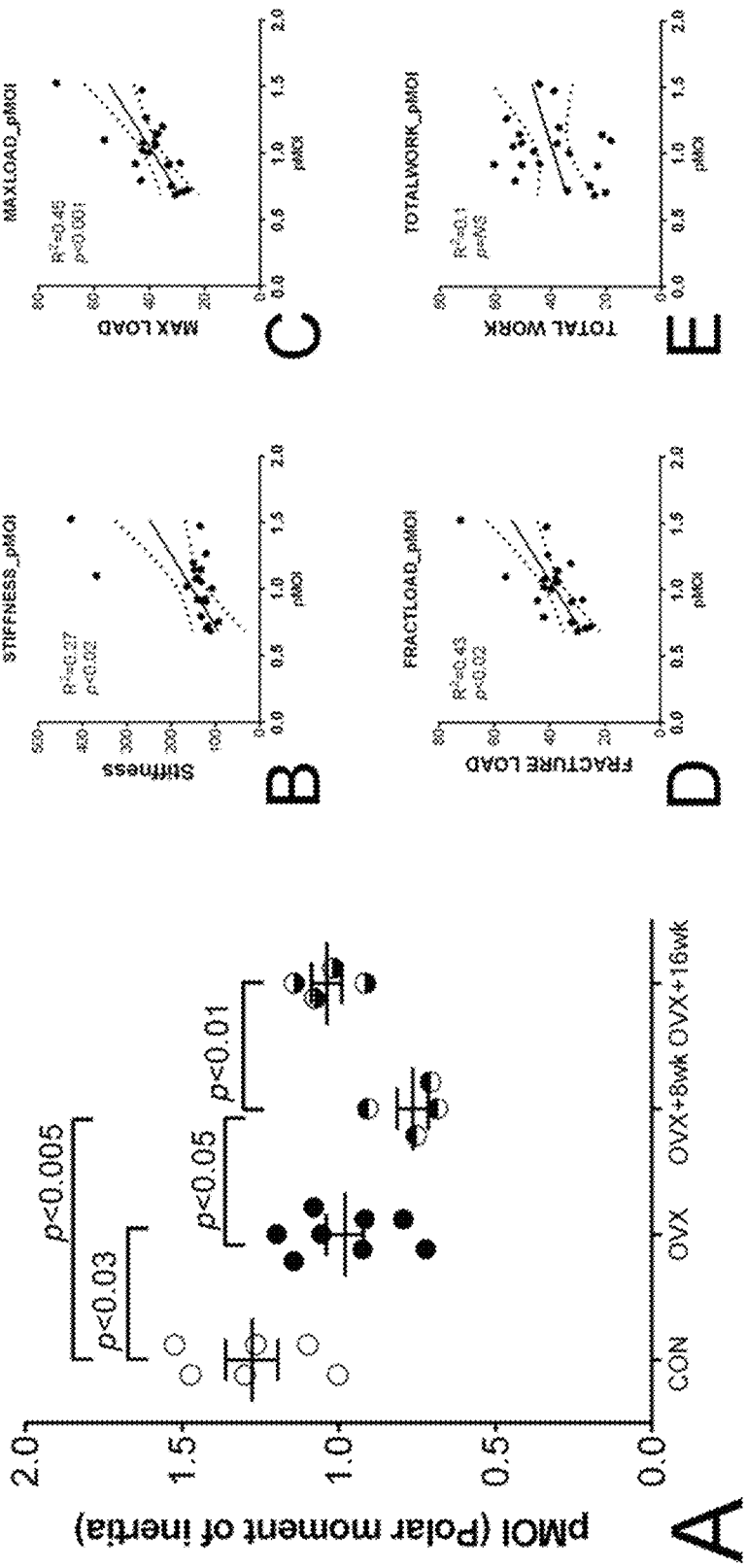
FIG. 34 is a series of graphs (34A-E) showing overall strength of bone in normo- and hypergastrinemic Mastomys ovariectomy models. The polar moment of inertia (pMOI) was significantly decreased in ovariectomized animals (25%, 34A). This measure of torsional load failure was specifically amplified by short-term hypergastrinemia (~50%). The pMOI was significantly correlated with stiffness ($R^2$=0.23—34B), the maximum load ($R^2$=0.33—34C) and the fracture load ($R^2$=0.3—34D). The total work was not correlated with the pMOI (34E). These results confirm that the torsional strength of bones following ovariectomy is decreased and that short-term gastrin specifically amplifies this parameter. The overall correlation with stiffness and maximal/fracture loads is a reflection of the effects of ovariectomy on the Mastomys. CON=control animals, OVX=ovariectomized animals, 8 wk=short-term hypergastrinemia, 16 wk=long-term hypergastrinemia.

Mechanical Strength Assessment:

pMOI (polar moment of inertia) is a measure of the overall strength (and stiffness) of the bone and is proportional to the load failure (in torsion). It is increased in abnormal healing. This parameter was evaluated to provide an additional measure of bone strength since it specifically represents a measure of bone weakness. OVX decreased the pMOI which was further significantly reduced by short-term hypergastrinemia (FIG. 34A). This confirms that ovariectomy weakens bones and demonstrates that an increase in gastrin exacerbates bone weakness. Long-term hypergastrinemia was associated with a decreased pMOI (compared to controls) but was not different to OVX alone. This is consistent with the 4-point bending data (see above) and emphasizes the effects of gastrin during both short-term (abnormal activation and remodeling) and long-term (abnormal reversal and bone formation) exposure.

Figure 35:
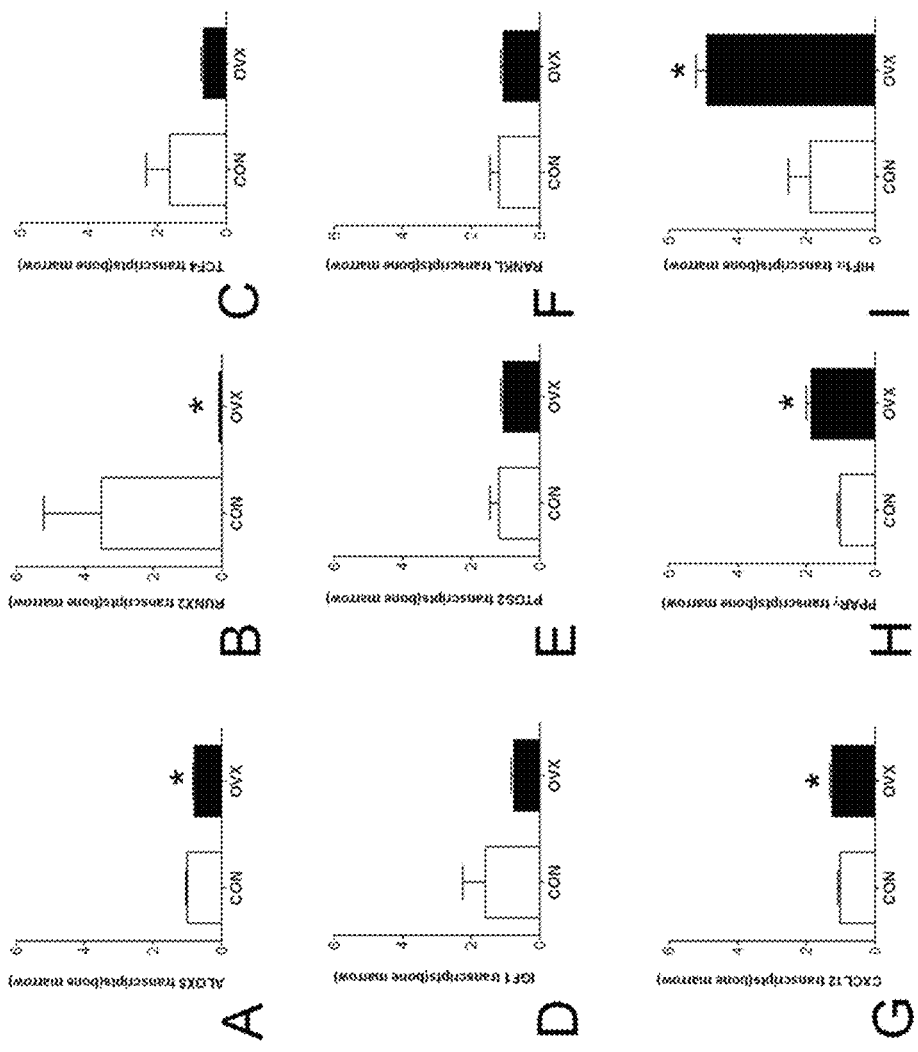
FIG. 35 is a series of graphs (35A-I) showing the expression of bone-remodeling related transcripts in cortical-derived bone marrow in the normo-gastrinemic Mastomys ovariectomy model. PCR results of bone marrow cells from normal compared to ovariectomized (OVX) Mastomys. Ovariectomy significantly decreased expression of ALOX5 (35A—inflammation: ~20%) and RUNX2 (29B—osteoblast differentiation: ~100%—35B) but not TCF4 (35C—involved in TGFβ-mediated bone formation), IGF-1 (35D—bone formation), PTGS2 (35E—inflammation) or RANKL (35F—bone loss). Increases were noted in CXCL12 (35G—osteoblast activation: ~20%), PPARg (35H—adipocyte differentiation: ~60%) and HIF-1a (35I—hypoxia-mediated bone damage: ~250%). These results confirm that loss of estrogen is associated with up-regulation of bone marrow-derived transcripts related to remodeling and bone loss. Mean±SEM, *p<0.05 vs. non-ovariectomized animals. CON=sham-operated control animals (n=11), OVX=ovariectomy (n=8).

Real-Time PCR Analysis of Bone Marrow:

Five genes associated with bone remodeling were significantly altered (two decreased and three elevated) by OVX. Specifically, cortical bone marrow-derived ALOX5 (inflammation) and RUNX2 (osteoblast differentiation) were significantly decreased (FIG. 35). Expression of CXCL12, PPARγ and HIF-1α were increased. CXCL12 is associated with PTH-mediated osteoblast activation, PPARγ with adipocyte differentiation (bone protection mechanism) and HIF-1α with hypoxia-mediated bone damage (negatively regulates RUNX2 expression, related to periosteal osteoprogenitor activation). This is consistent with inhibition of osteoblast differentiation and osteoclast activation.

Neither short-term (8 week) nor long-term (16 week) hypergastrinemia significantly altered (amplified or inhibited) OVX-mediated gene expression alterations in bone remodeling. However, PTGS2 (or inducible COX2) was significantly decreased by gastrin. This is a bone injury response and consistent with a biological response associated with protection.

Figure 36:
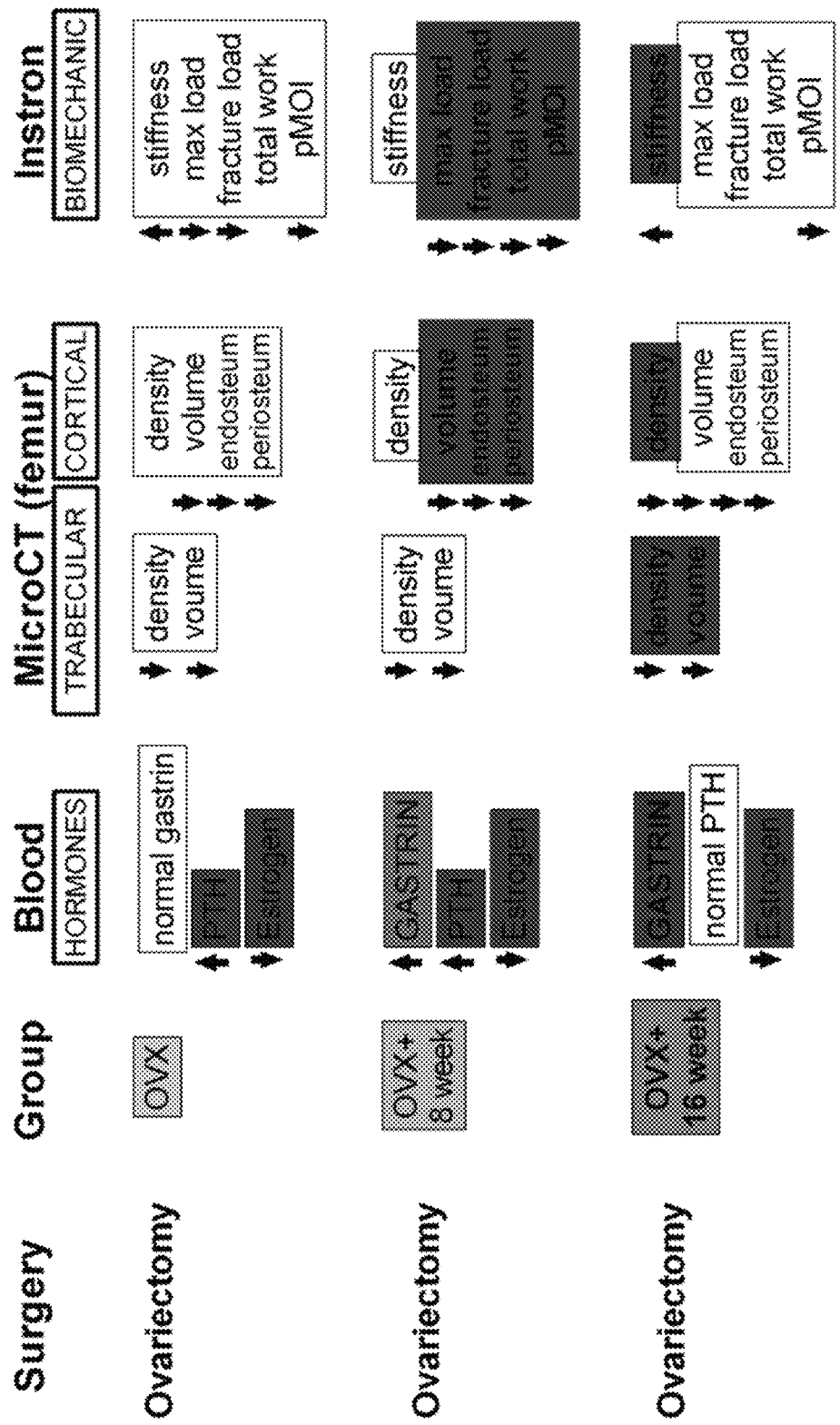
FIG. 36 is a chart showing an overview of Gastrin-mediated bone phenotype alterations in the ovariectomized Mastomys model. In comparison to ovariectomy alone (normo-gastrinemic animals, with decreased estrogen, elevated PTH and an osteoporotic features e.g., stiff, weak bone), short-term hypergastrinemic animals exhibited decreased cortical bone features that was associated with a weaker bone with lower torsional strength. This phenotype was more pronounced than in ovariectomy alone. In the long-term hypergastrinemic animals (exhibit normal PTH), trabecular bone damage resulting in a significantly stiff bone were noted. This phenotype was more pronounced than in ovariectomy alone. pMOI=polar moment of inertia, PTH=parathyroid hormone.

Summary (FIG. 36):

Ovariectomy-associated bone (trabecular and cortical) abnormalities in the Mastomys model were associated with alterations in bone physiology (inhibition of osteoblast function) and gene expression at the level of cortical-derived bone marrow cells. This was associated with an increase of gastric mucosal neuroendocrine markers including HDC and calcium sensing/PTH1R responses.

Short-term hypergastrinemia after ovariectomy further weakened bone with similar alterations in bone phenotypes (decreased trabecular and cortical densities and volumes) and bone marrow gene expression profiles (e.g., activation of HIF-1α) as ovariectomy alone. Increased gastrin transcription was the most significant alteration in the stomach with normalization of CaSR/PTH1R expression.

Long-term hypergastrinemia resulted in a weak and very stiff bone. Similar alterations were noted in phenotypes (decreased trabecular and cortical densities and volumes) as well as in bone marrow gene expression (activation of HIF-1α) to ovariectomy alone. The most significant gastric alteration was activation of HDC with normalization of CaSR/PTH1R expression.

Overall, bone loss/abnormalities are associated with alterations in cellular bone marrow activation and changes in gastric mucosal neuroendocrine cell transcription Example 7: Effects on Gastric Neuroendocrine Function and Bone Dynamics: Gene Knockout Mice Models—with and without Ovariectomy Studies using knockout models of gastrin and histamine demonstrated a relationship between histamine and gastrin in the mediation of bone metabolism (integrity) and evaluated the role of gastrin and histamine in a different species model to Mastomys. These studies evaluated effects of gastrin-mediated histamine secretion on bone biology (as well as our observations that G cells are regulated by estrogen). Three knockout combinations were used: HDC knockout mice as well as gastrin knockout and dual combination (HDC/GAS) knockout animals.

Figure 37:
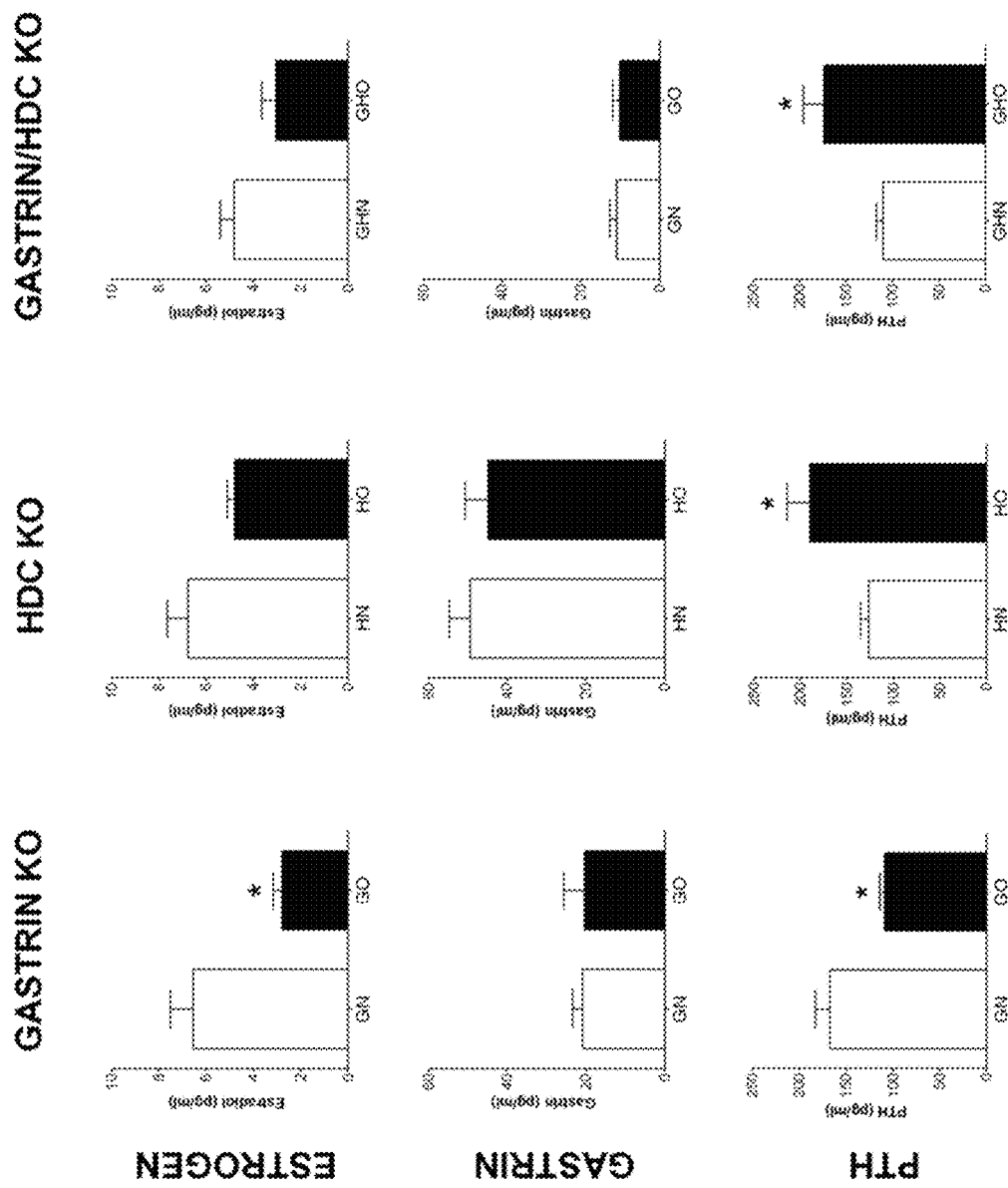
FIG. 37 is a series of graphs showing the effects of gastrin knockout, histidine decarboxylase knockout or double knockout on circulating hormone levels in ovariectomized mouse models. Estrogen levels were significantly reduced in all animals ~50% by ovariectomy. Gastrin levels were unaffected by ovariectomy but the HDC KO animals expressed ~3-fold increased levels compared to either the gastrin KO or double KO animals. PTH was significantly reduced (~80%) in the gastrin KO animals. Levels in contrast were significantly increased following ovariectomy in both the HDC and double KO animals (~100%). These results demonstrate that estrogen loss does not activate PTH release in the gastrin KO animals. This suggests gastrin modifies the function of estrogen in the parathyroid gland. Mean±SEM, *p<0.05 vs. non-ovariectomized animals. G=Gastrin KO, GH=Gastrin/HDC double KO, H=HDC KO, KO=knockout, N=no ovariectomy, O=ovariectomy.

Circulating Hormones:

a) Estradiol was decreased (80-90%) to similar levels (~2 pg/ml) in all three KO models following ovariectomy (FIG. 37). b) Gastrin was low in both the gastrin and double KO mice (10-20 pg/ml); in HDC KO animals, gastrin levels were 5× higher than the GAS or GAS/HDC KO animals. These levels were unaffected by ovariectomy and were similar to normogastrinemic Mastomys.

PTH levels were similar in all three KO models (FIG. 37) but were −50% of normogastrinemic Mastomys. Ovariectomy increased PTH levels in HDC and HDC/GAS KO animals consistent with loss of the inhibitory effect of estrogen on parathyroid secretion. This suggests an absence of histamine has no effect on parathyroid secretion. In contrast, PTH was decreased following ovariectomy in the GAS KO animals. In the Mastomys, 8 week hypergastrinemia increased PTH release, and in vitro experiments confirmed a gastrin-mediated PTH release. This suggests that gastrin is required for physiological PTH release. The combination of loss of both estrogen and gastrin results in a "low" PTH secreting parathyroid gland. As PTH is associated with activation of osteoclast via RANK-osteoblast (bone resorption)[102], an absence of gastrin in this setting could be construed as "protective".

Figure 38:
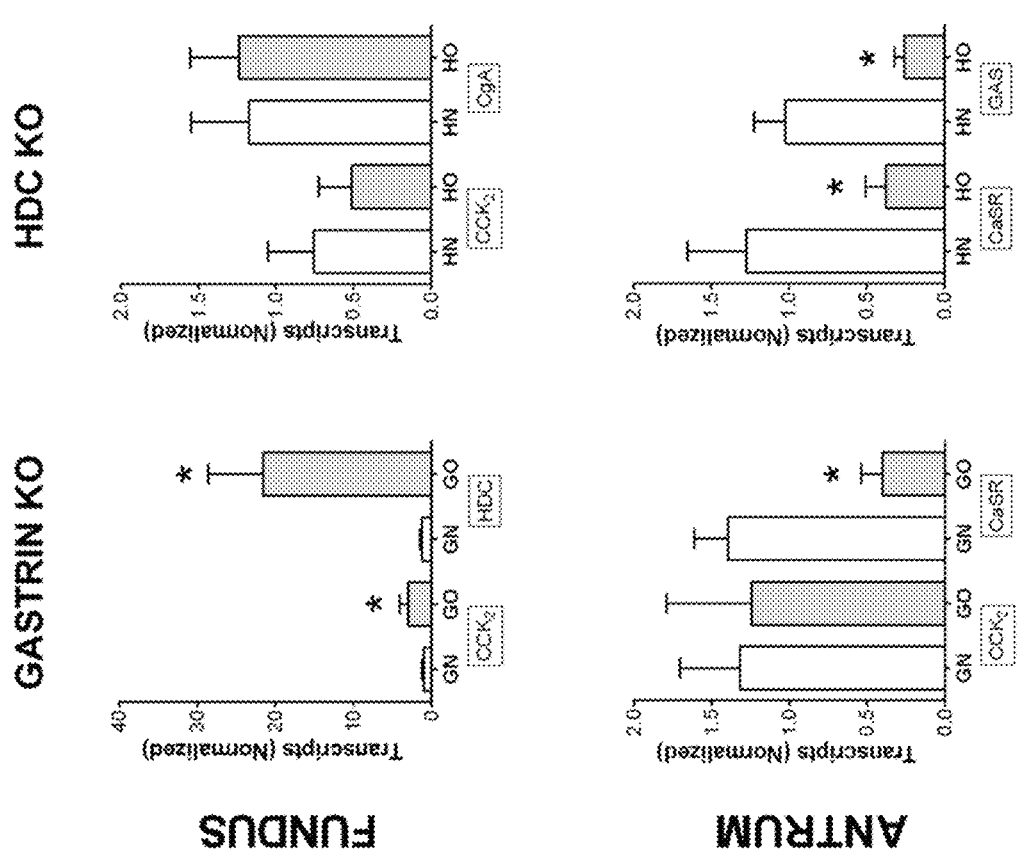
FIG. 38 is a series of graphs showing expression of neuroendocrine and calcium sensing receptors in the stomach of the ovariectomized mouse knockout models. In the fundus, a combination of gastrin KO and ovariectomy significantly increased CCK2 (ECL cell gastrin responsiveness: ~3-fold) and HDC (ECL histamine synthesis: ~20-fold). In contrast, no changes were noted in the fundus of ovariectomized HDC KO mice. In the antrum, CaSR was significantly reduced in the ovariectomized gastrin KO animals (~60%), while both CaSR (~60%) as well as gastrin expression itself (~70%) were reduced in the antrum of ovariectomized HDC KO mice. In one aspect, this reflects that ovariectomy and the loss of estrogen significantly activates the ECL cell and decreases the calcium-sensing responses of G cells in gastrin KO animals. In the HDC KO animals, the effects of ovariectomy are limited to the antrum. Mean±SEM, *p<0.05 vs. non-ovariectomized animals. G=Gastrin KO, H=HDC KO, KO=knockout, N=no ovariectomy, O=ovariectomy

The Stomach:

In gastrin KO animals, OVX significantly upregulated the CCK2 receptor in the fundus (3-fold) (FIG. 38) and increased HDC-10-fold indicating estrogen exerts an inhibitory effect on the ECL cell. In the antral G cells, OVX down-regulated CaSR by 60% indicating G cell calcium sensing is regulated by estrogen. In the HDC KO animals OVX down-regulated most target genes including CaSR, PTH1R and CCK2 compared to control (no ovariectomy). Gastrin was also significantly down-regulated. In the double KO animal, CCK2 was upregulated by ovariectomy. These data indicate that estrogen regulates expression of transcripts involved in calcium sensing and hence calcium metabolism. In particular, the ECL and the G cell of the stomach are estrogen-responsive particularly in terms of calcium physiology.

Figure 24:
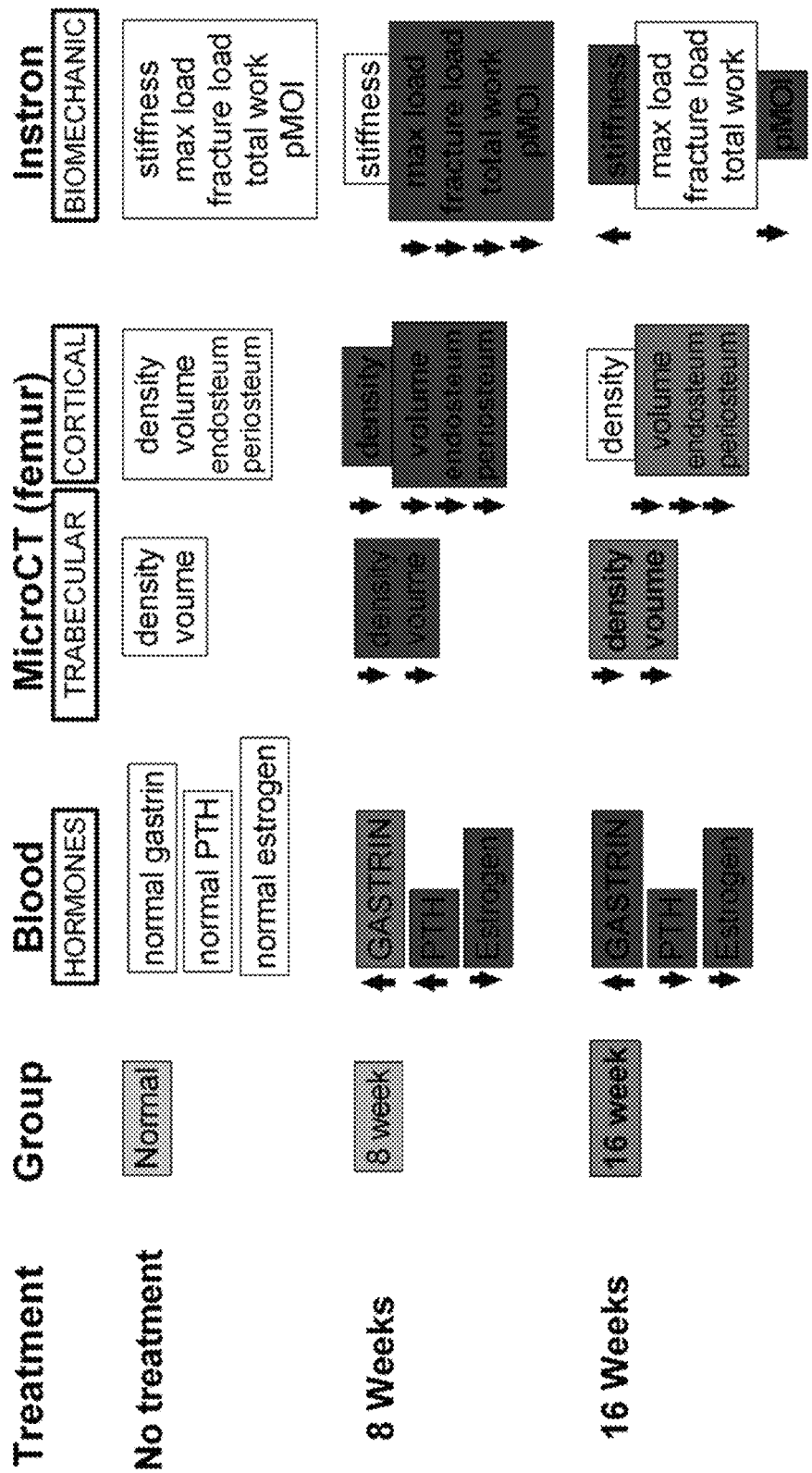
FIG. 24 is a chart showing an overview of Gastrin-mediated bone phenotype alterations in the Mastomys model. In comparison to control (untreated, normo-gastrinemic animals), short-term treated animals exhibited elevated circulating gastrin and PTH but decreased estradiol. This was associated with a decreased bone density and an osteoporotic phenotype (including weak bone with low torsional strength). In the long-term treated animals, elevated circulating gastrin was noted but both PTH and estradiol were decreased. This was associated with a decreased bone density and osteoporotic phenotype that was characterized by a weak but stiff bone. pMOI=polar moment of inertia, PTH=parathyroid hormone
Figure 39:
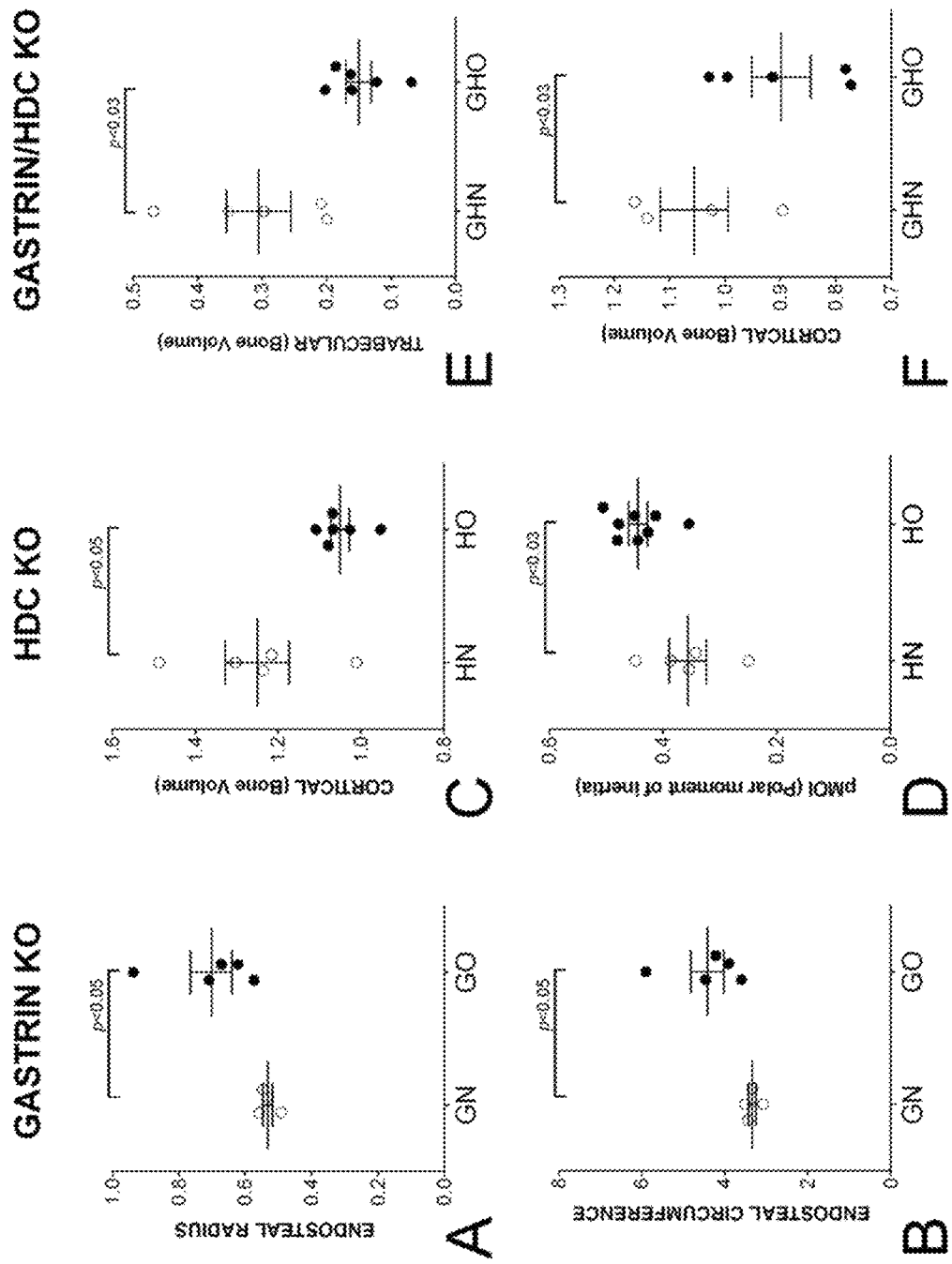
FIG. 39 is a series of graphs (39A-F) showing MicroCT measurements in cortical and trabecular measurements in the ovariectomized mouse models. In the gastrin KO animals, both the endosteal radius (39A) and circumference (39B) were significantly increased (~30%) following ovariectomy. This reflects that the combination of estrogen loss and an absence of gastrin increased cortical bone thickness. The loss of gastrin, in these circumstances, does not negatively affect the bone. In the HDC KO animals, ovariectomy significantly decreased cortical bone volume (~25%—39C) but resulted in a bone with a higher torsional strength (39D). This identifies that the loss of histamine exacerbates the estrogen effects on the bone. The double KO was also associated with decreases in trabecular (~50%—39E) and cortical bone volume (~15%—39F) but this did not translate into a significant bone weakness. This identifies that although there are some changes in the bone phenotype, the combination of loss of gastrin and histamine does not significantly alter bone biology. G=Gastrin KO, GH=Gastrin/HDC double KO, H=HDC KO, N=no ovariectomy, O=ovariectomy.

Bone Morphology and Dynamics:

Bone Micro CT:

In the Gastrin KO mice, ovariectomy had no significant effect on femur density and volume but, increased endosteum and periosteum thickness (FIG. 39A). This was directly opposite to the effects noted in short and long-term hypergastrinemia (decreased trabecular and cortical bone density and volume as well as endosteal and periosteal measurements—see FIG. 24). This resulted in bone which was not stiff and weakened compared to non-ovariectomized bones. This demonstrates that an absence of gastrin (in a low estrogen milieu) was protective and may reflect the low circulating PTH levels in these animals.

HDC KO Mice:

Ovariectomy in HDC KO mice had no significant effect on femur density and volume or on endosteum/periosteum thickness. The bone, however, was stiff, required a higher load to fracture and exhibited an increased pMOI (p<0.03) compared to non-ovariectomized bones (FIG. 39B). Our investigations therefore confirm earlier studies [99] that a combination of estrogen and histamine loss increases bone strength.

Gas/HDC KO Mice:

Ovariectomy in gastrin/HDC double KO mice had no significant effect on femur density but trabecular and cortical volumes were decreased (p<0.03) (FIG. 39C). No changes were noted in endosteum/periosteum thickness. This resulted in bone which was not weakened compared to non-ovariectomized bones.

Figure 40:
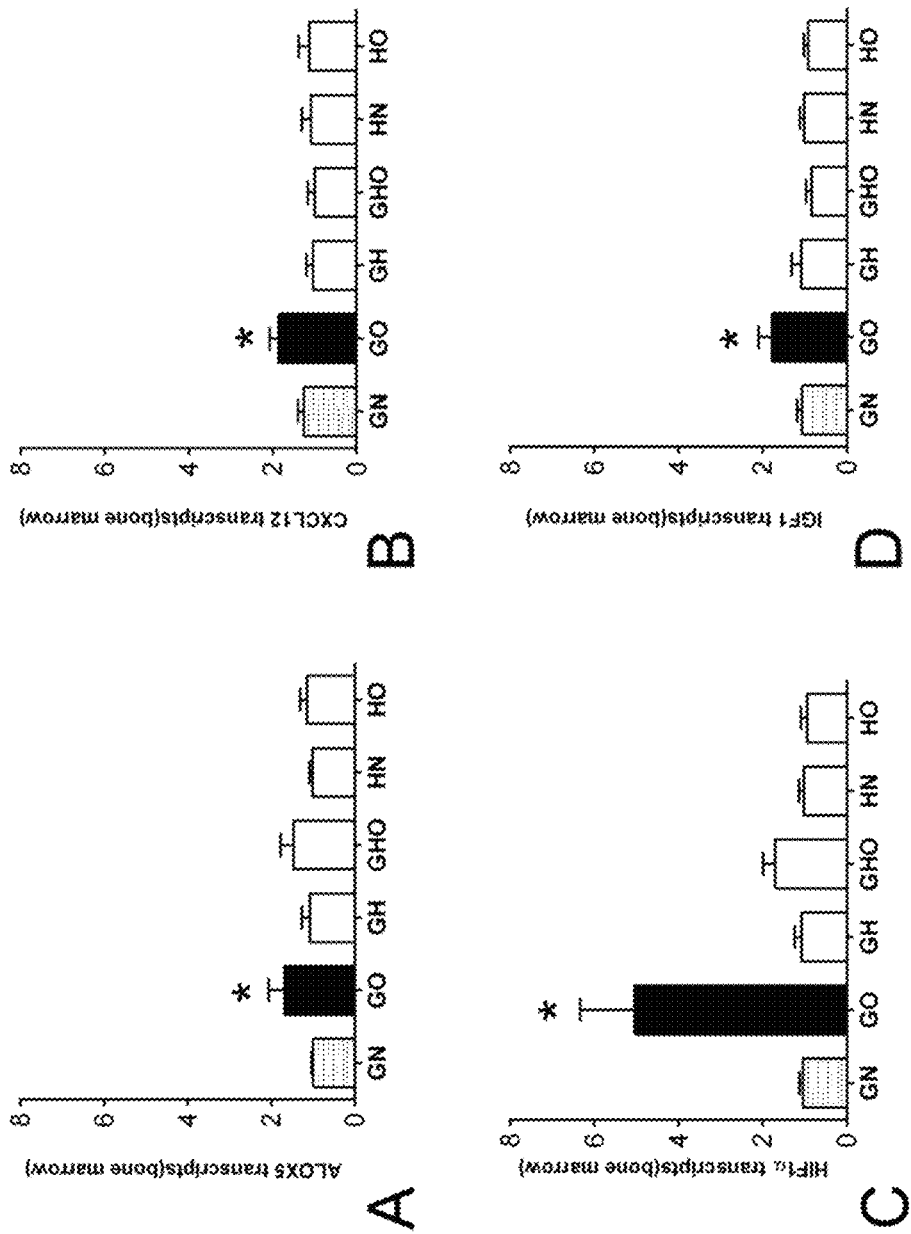
FIG. 40 is a series of graphs (40A-D) showing expression of bone-remodeling related transcripts in cortical-derived bone marrow in the knockout mouse ovariectomy models. PCR results of bone marrow cells from non-ovariectomized compared to ovariectomized mice. Ovariectomy significantly increased expression of ALOX5 (40A—inflammation: ~100%), CXCL12 (40B—osteoblast activation: ~70%), HIF-1a (40C—hypoxia-mediated bone damage: ~5-fold) and IGF-1 (40D—bone formation: ~100%), only in the gastrin KO animals. These results suggest that a combination of a loss of estrogen and gastrin is associated with up-regulation of bone marrow-derived transcripts related to remodeling. Values were normalized to non-ovariectomized animals. Mean±SEM, *p<0.05 vs. non-ovariectomized animals. G=Gastrin KO, GH=Gastrin/HDC double KO, H=HDC KO, N=no ovariectomy, O=ovariectomy

Bone marrow qPCR: Ovariectomy in gastrin KO animals was associated with upregulation of two genes, ALOX5 and CXCL12 (FIG. 40A-B). These are involved in leukotriene synthesis and inflammation and osteoblast activation through PTH, respectively. In the Mastomys model, ovariectomy down-regulated ALOX5 but up-regulated CXCL12, effects not significantly altered by hypergastrinemia. Ovariectomy in the HDC and HDC/GAS KO animals had no significant effect indicating that histamine does not play a role in the regulation of these two genes.

Bone marrow PCR also identified that ovariectomy in gastrin KO animals was associated with upregulation of HIF-1α and IGF1 (FIG. 40C-D). These are involved, as previously noted, in regulation of osteoprogenitors and maintenance of bone mass, respectively.

Figure 41:
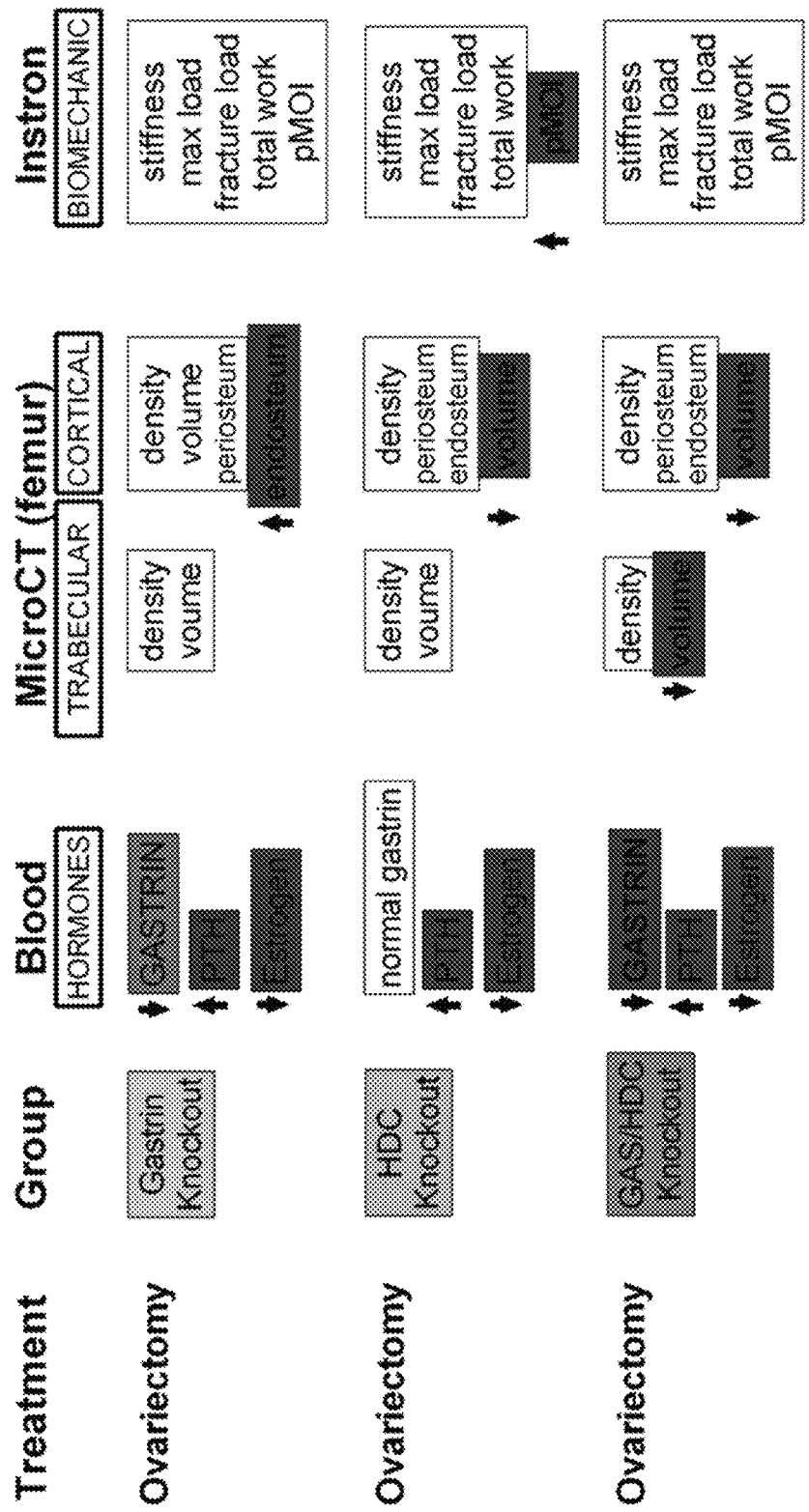
FIG. 41 is a chart showing an overview of bone phenotype alterations in the ovariectomized mouse knockout models. The gastrin knockout animal, following ovariectomy, exhibited an increase in endosteal features and a relatively normal bone phenotype despite the "pro-osteopenic" hormonal milieu (loss of estrogen, elevated PTH). The HDC KO mouse, exhibited a decreased cortical volume but the bone was stronger. The double knockout also exhibited some changes in trabecular and cortical features—these did not result in altered bone strength. The combinatorial loss (both gastrin and histamine), despite loss of ovarian function and elevated PTH, did not result in an abnormal bone phenotype. A decrease in gastrin appears to be protective for the bone phenotype. GAS=gastrin, pMOI=polar moment of inertia, PTH=parathyroid hormone.

Summary (FIG. 41):

Gastrin loss (in a low estrogen milieu) in the mouse model altered bone physiology but was not associated with a significant difference in bone strength. In contrast ovariectomy with either short- or long-term hypergastrinemia (in the Mastomys model) resulted in a significantly weaker bone. Gastrin therefore appears to have an unfavorable and "anti-protective" effect on the bone marrow. HDC KO alone (in a low estrogen milieu) was associated with a significantly stronger (and stiffer) bone suggesting that histamine, like gastrin, may play a regulatory role in bone physiology. Removal of histamine (through HDC KO) reversed this effect and is therefore consistent with the assertion that gastrin and histamine in tandem are key regulators of bone physiology.

A combination of gastrin and HDC loss (e.g., loss of histamine) in a low estrogen milieu was not associated with a significantly weaker bone and bone dynamics were not different to normal. This suggests that histamine (like gastrin) may activate an "osteoporotic"-like bone phenotype. Thus, decrease (removal) of histamine (through HDC KO) reversed the pro-osteoporotic effect induced by estrogen diminution.

Example 8: Proof of Principle Studies: Effects of a Gastrin Antagonist on the Ovariectomy-Mediated Bone Phenotype in Three Rodent Models The effects of the gastrin antagonist, YF476, on OVX-mediated bone density loss/bone alterations in three rodent models were evaluated with a focus on bone strength studies, morphology and circulating biomarkers. Two "normal" OVX models were examined: a) Mouse (strain: CD-1 [Swiss strain]—Charles River) and b) Rat (strain: CD IGS [Sprague Dawley strain]—Charles River), as well as the Mastomys (endogenously activated gastrin/CCK2 receptor signaling) model.

Animals underwent surgery (OVX) at 2 months of age, were allowed to recover and were then exposed to oral acid inhibition as well as the gastrin antagonist (GA), YF476 (single injection). Both mice and rats were exposed to the PPI, omeprazole, while the Mastomys were exposed to the $H_2$ Receptor antagonist, loxitidine. GA administration was a single subcutaneous injection at the start of acid inhibition. Pharmacokinetically, this dose ranges between 15-20 nmol over an 8 week period. Details regarding dosing are included in TABLE 3.

TABLE 3

Dosing in the proof-of-principle studies

| Species | Acid Inhibitor | GA |
|---|---|---|
| Mouse - D-1 | 2 ml/10 g body weight; 21 μg/mg/day) | 15 ug/animal |
| Rat - D | 0.8 ml/10 g body weight; 8.5 μg/mg/day | 50 ug/animal |
| Mastomys | 0.85 ml/10 g body weight; 82.7-91.2 μg/mg/day | 10 ug/animal |

Three groups were included for each animal model: a) Group A=placebo/saline treated (no OVX/Controls); b) Group B=OVX+Acid Inhibitory therapy (OVX); and c) Group C=GA treated ovariectomized animals (OVX+GA). At the termination of study (2 months), we evaluated whether the GA reversed the OVX-mediated alterations in bone parameters (microCT, bone strength and histomorphometry as well as circulating markers).

Figure 42:
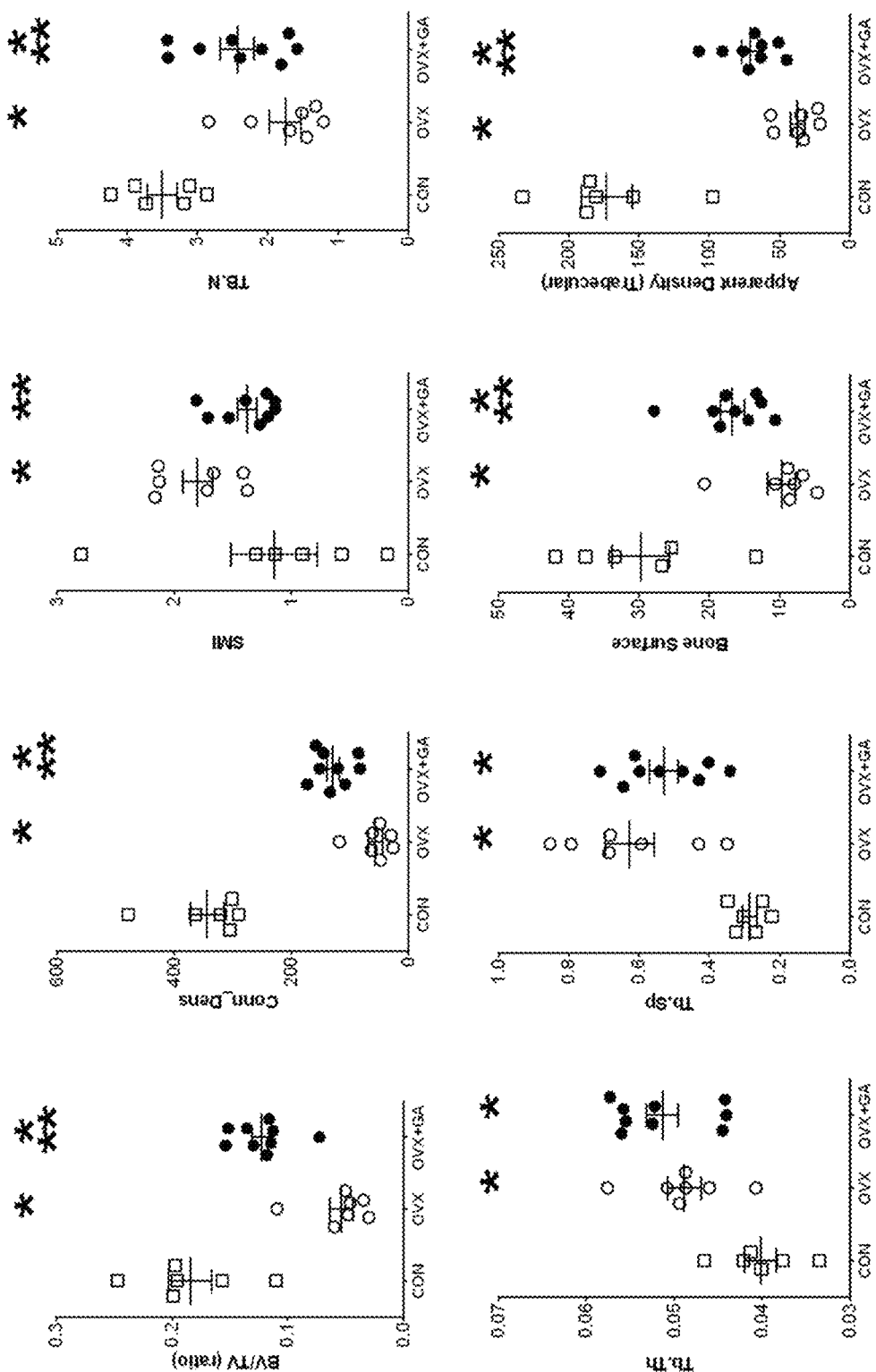
FIG. 42 is a series of graphs showing MicroCT measurements in trabecular bone in control, ovariectomized and ovariectomy CD-1 mice treated with the gastrin antagonist. The BV/TV ratio, connective density (Conn-Dens), trabecular number (TB.N), bone surface and density, were all significantly decreased by ovariectomy. The structural model index (SMI), trabecular thickness (Tb.Th) and trabecular spacing (Tb.Sp) were all increased. Gastrin antagonist treatment reversed the majority of these effects except for trabecular thickness and spacing. These results demonstrate that selectively inhibiting the gastrin receptor ameliorates bone loss in the ovariectomy model and results in microCT features consistent with a normal phenotype. CON=control animals, OVX=ovariectomized animals, OVX+GA=gastrin antagonist treated ovariectomized animals. Mean±SEM. *p<0.05 vs. CON, **p<0.05 vs. OVX alone.

Model 1:

Mouse OVX:

At the start of GA treatment, animals were 89 days (3.0 months) and at study termination, they were 146 days (4.8 months) old. An examination of trabecular bone data identified that ovariectomy significantly reduced BV/TV (0.05±0.02 vs. 0.18±0.04, p<0.05) and the density (37±5 vs. 173±18, p<0.05), and increased the SMI (1.8±1.2 vs. 1.1±0.4, p<0.05) and trabecular spacing (0.6±0.18 vs. 0.28±0.05, p<0.05) (TABLE 4, FIG. 42). Gastrin antagonist treatment reversed these ovariectomy-mediated bone alterations except for trabecular thickness and spacing which remained increased. This was associated with a significant increase in trabecular bone density (70.7±19, p<0.05 vs. OVX).

TABLE 4

Trabecular Bone results in Model 1

| Parameter | BV/TV | Conns-Dens | SMI | Tb. N | Tb. Th | Tb. Sp | Dens<sup>&</sup> | BS |
|---|---|---|---|---|---|---|---|---|
| Control (n = 6) | 0.185 | 343.3 | 1.15 | 3.5 | 0.040 | 0.285 | 173 | 29.7 |
| OVX (n = 7) | 0.054 | 56.4 | 1.8 | 1.75 | 0.049 | 0.627 | 37.2 | 9.7 |
| GA-treated (O + YF: n = 8) | 0.123 | 128.6 | 1.38 | 2.43 | 0.051 | 0.528 | 70.7 | 16.8 |
| % Change (OVX) | −70%* | −84%* | +56%* | −50%* | +22%* | +116%* | −78%* | −77%* |
| % Change (GA-treated) | −33%*, ** | −62%*, ** | +20%** | −30%*, ** | +28%* | +82%* | −60%*, ** | −32%*, ** |

<sup>&</sup>Apparent Density (trabecular);
*p < 0.05 vs. control;
**p < 0.05 vs OVX alone (untreated)

Figure 43:
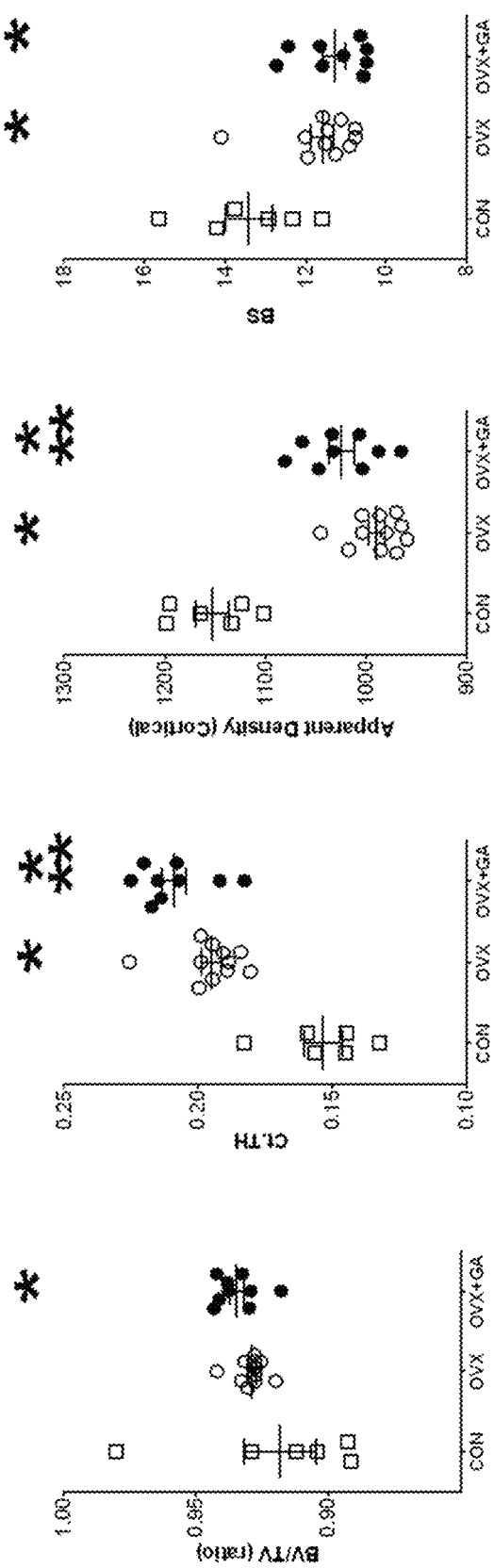
FIG. 43 is a series of graphs showing MicroCT measurements in cortical bone in control, ovariectomized and ovariectomy CD-1 mice treated with the gastrin antagonist. The cortical density and bone surface (BS) were all significantly decreased by ovariectomy. The cortical thickness (Ct.TH) was increased. Gastrin antagonist treatment reversed the effects on density but did not alter thickness. These results demonstrate that selectively inhibiting the gastrin receptor reverses cortical density loss in the ovariectomy model. CON=control animals, OVX=ovariectomized animals, OVX+GA=gastrin antagonist treated ovariectomized animals. Mean±SEM. *p<0.05 vs. CON, **p<0.05 vs. OVX alone.

An analysis of cortical bone parameters identified that ovariectomy significantly decreased bone surface (11.6±0.9 vs. 13.4±1.4, p<0.05), increased cortical thickness (0.2±0.01 vs. 0.15±0.01, p<0.05) and was associated with a decrease (989±26 vs. 1153±39, p<0.05) in cortical density (TABLE 5, FIG. 43). Gastrin-antagonist treatment reversed the OVX-mediated decrease in density (1025±37, p<0.05 vs OVX).

TABLE 5

Cortical bone data in Model 1

| Parameter | BV/TV | Ct. Th | Dens[&] | BS | pMOI |
|---|---|---|---|---|---|
| Control (n = 6) | 0.92 | 0.15 | 1153 | 13.4 | 0.4 |
| OVX (n = 7) | 0.93 | 0.19 | 992 | 11.7 | 0.4 |
| GA-treated (O + YF: n = 8) | 0.93 | 0.21 | 1025 | 11.3 | 0.35 |
| % Change (OVX) | +1% | +30%* | −14%* | −13%* | +4% |
| % Change (GA-treated) | 2%* | +39%*,** | −11%*,** | −15%* | −11% |

[&]Apparent Density (cortical),
*p < 0.05 vs. control;
**p < 0.05 vs OVX alone (untreated)

Figure 44:
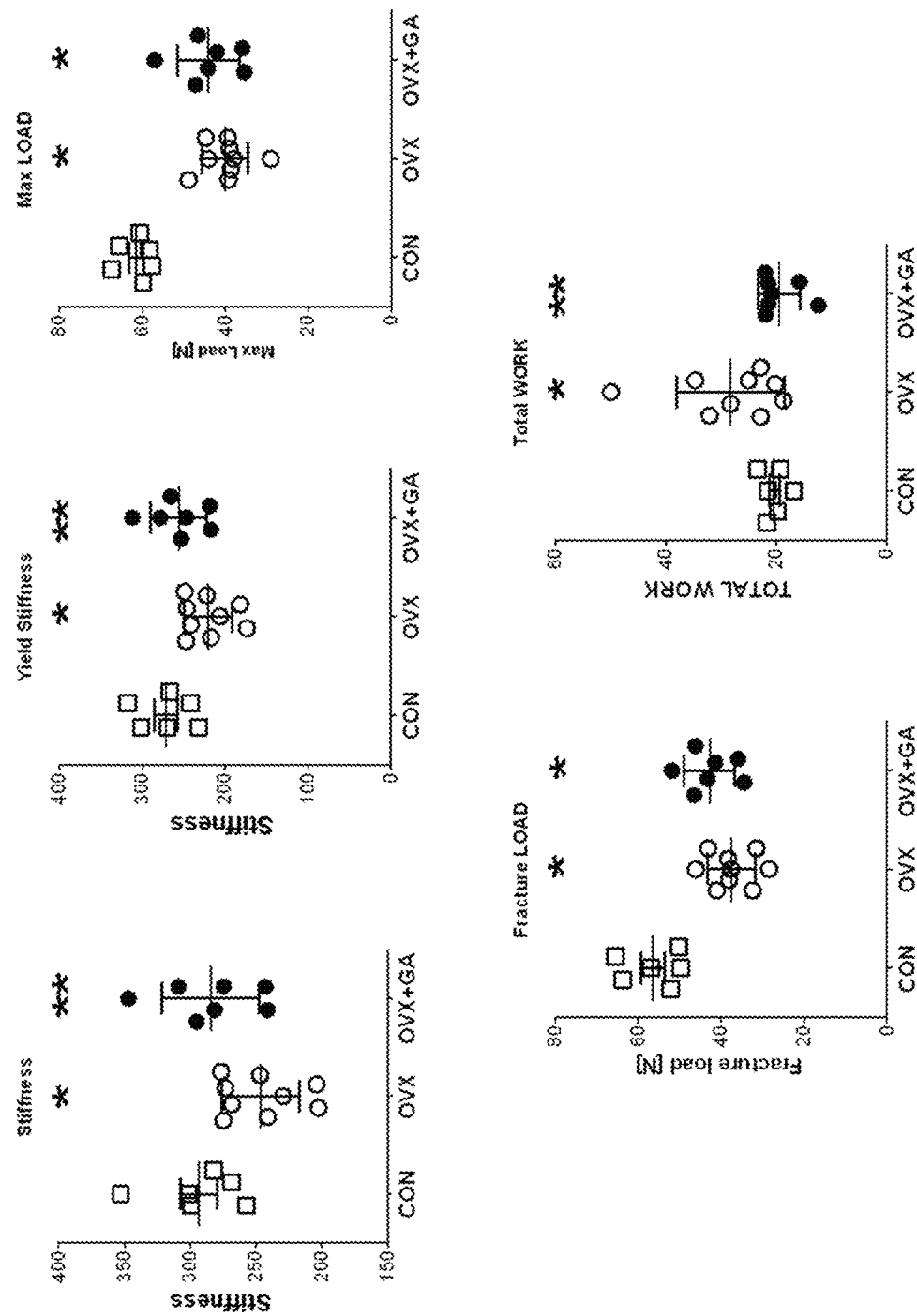
FIG. 44 is a series of graphs showing overall strength of bone in control, untreated and gastrin-antagonist treated mice. Ovariectomy significantly decreased bone strength including stiffness, yield stiffness, the maximal (max) load and fracture load for breaking and increased the total work required to break the bone. Treatment with the gastrin antagonist reversed these effects except for load. These results confirm that the strength of bones following ovariectomy is decreased and that targeting the gastrin receptor ameliorated the loss-of-estrogen mediated effect. CON=control animals, OVX=ovariectomized animals, 8 wk=short-term hypergastrinemia, 16 wk=long-term hypergastrinemia. Mean±SEM. *p<0.05 vs. CON, **p<0.05 vs. OVX alone.

Measurements of bone strength using Instron device confirmed the utility of the gastrin-antagonist in reversing the OVX-mediated bone phenotype. Ovariectomy significantly reduced (p<0.05) the bone strength (stiffness [246±29 vs. 294±34], yield stiffness [221±28 vs. 271±33], the fracture load to breakage [37±6 vs. 56±7]) and increased the total work required to break the bone [28.3±9.7 vs. 20.4±2.3, p<0.05]. The gastrin antagonist treatment normalized these ovariectomy-mediated bone alterations except for the fracture load [43±6] which was increased but remained lower than controls (TABLE 6, FIG. 44).

TABLE 6

Bone strength data

| Parameter | Stiffness | Yield (Stiffness) | Max Load | Fracture Load | Total Work |
|---|---|---|---|---|---|
| Control (n = 6) | 294 | 271 | 61.6 | 56.4 | 20.4 |
| OVX (n = 9) | 246 | 221 | 40.1 | 37.4 | 28.3 |
| GA-treated (O + YF: n = 8) | 285 | 256 | 44.1 | 42.8 | 19.4 |
| % Change (OVX) | −16%* | −18%* | −34%* | −33%* | +39%* |
| % Change (GA-treated) | −3%** | −5%** | −28%* | −24%* | −4%** |

*p < 0.05 vs. control;
**p < 0.05 vs OVX alone (untreated)

Figure 45:
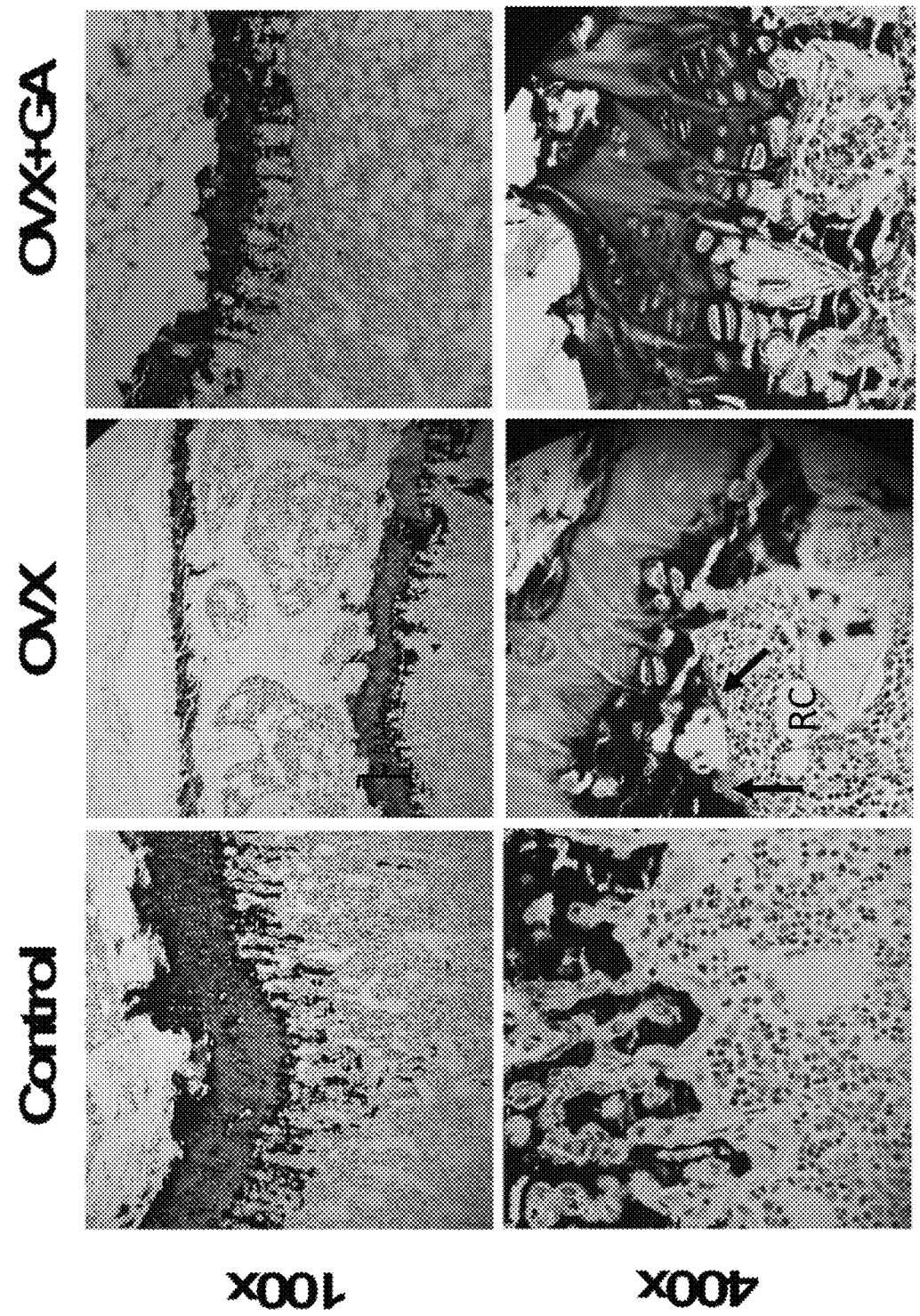
FIG. 45 is a series of photomicrographs showing Toluidine-blue, TRAP-stained femurs from control and ovariectomized CD-1 mice treated with the gastrin antagonist (OVX+GA) or vehicle (OVX). Patterns of bone mineralization (BM: decreased), resorption cavities (RC: increased) and osteoclasts (stained multinuclear cells (two arrows): increased) were affected by OVX. These effects were reversed by drug treatment. In one aspect, this means that targeting CCK2 receptors normalizes bone morphology irrespective of low estrogen levels.

Histomorphometry identified decreased bone mineralization with an increased resorption cavities as well as significantly increased (p<0.05) numbers of TRAP-positive osteoclasts (29±5 vs. 16±3, p<0.05) in the OVX mice. Gastrin-antagonist treatment reversed these phenomena (FIG. 45).

Figure 46:
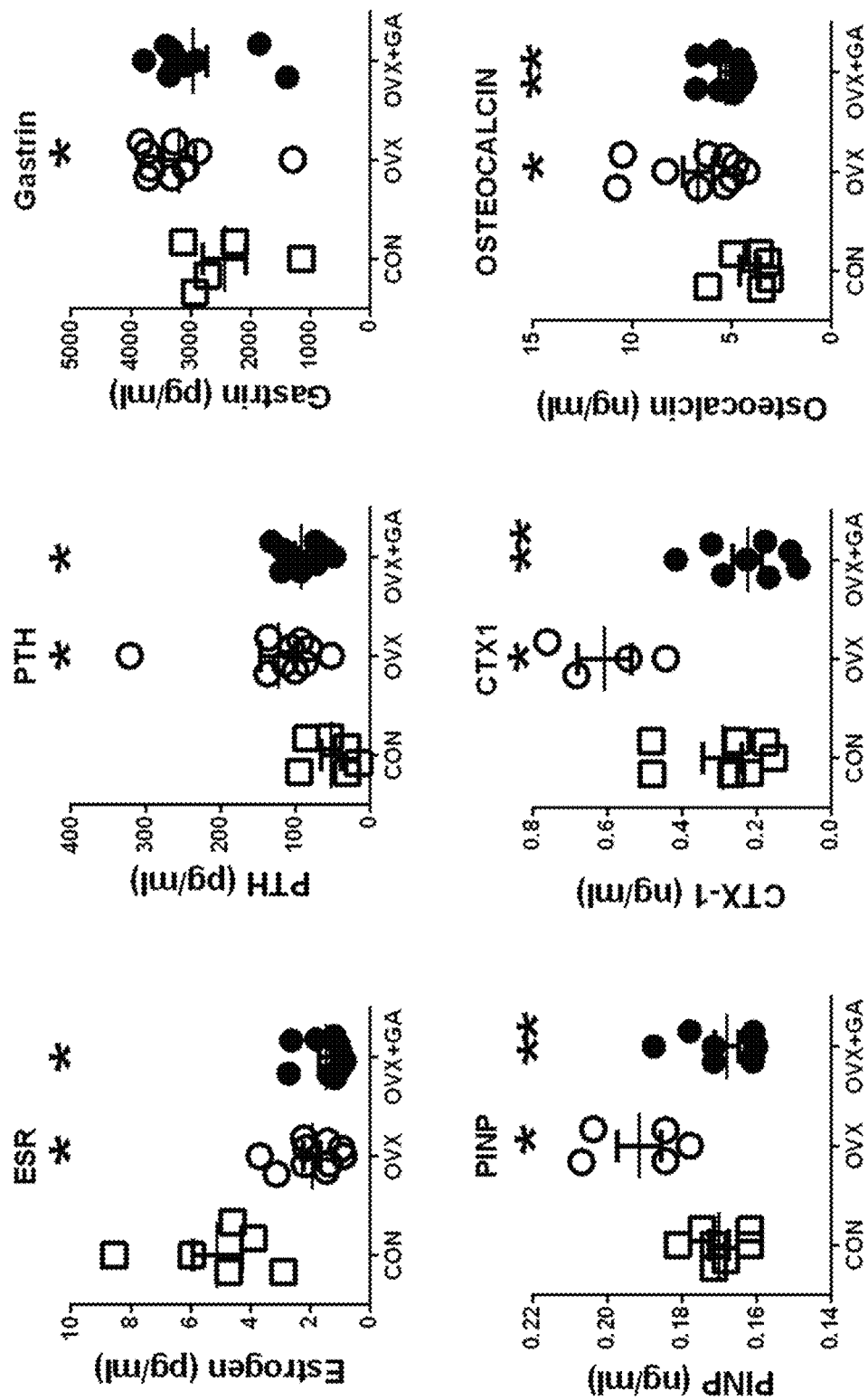
FIG. 46 is a series of graphs showing the effects of gastrin antagonist treatment on circulating hormone levels in the ovariectomized mouse model. Estrogen was significantly decreased while both PTH and gastrin were elevated by ovariectomy. Gastrin antagonist treatment had no effect on PTH but normalized gastrin levels. Ovariectomy increased all three bone markers, PINP, CTX1 and osteocalcin. The gastrin antagonist inhibited each of these effects. We interpret these results to reflect that markers of bone activity engendered by ovariectomy are normalized by targeting the gastrin receptor. CON=control animals, OVX=ovariectomized animals, OVX+GA=gastrin antagonist treated ovariectomized animals. Mean±SEM. *p<0.05 vs. CON, **p<0.05 vs. OVX alone.

Ovariectomy significantly (p<0.05) decreased circulating estrogen (1.9±0.9 pg/ml vs. 5.1±1.9) and was associated with an increase in PTH (123±74 pg/ml vs. 51±32) and gastrin (3200±263 pg/ml vs. 2437±787). Treatment with the antagonist reversed the ovariectomy-mediated increase in gastrin, but not with PTH (TABLE 7, FIG. 46). Circulating bone biomarkers were also altered by OVX. Specifically, PINP was increased (0.19±0.01 ng/ml vs. 0.1y±0.006, p<0.05) as was CTx-1 (0.60±0.14 ng/ml vs. 0.29±0.13, p<0.05) and osteocalcin was elevated (6.7±2.3 ng/ml vs. 4.1±1.2, p<0.05). Treatment with the antagonist attenuated each of these three ovariectomy-mediated alterations.

TABLE 7

Circulating Blood Marker Levels in each of the three Groups

| Parameter | PTH | ESR | Gastrin | PINP | CTX-1 | Osteocalcin |
|---|---|---|---|---|---|---|
| Control (n = 6) | 51.3 | 5.1 | 2437 | 0.17 | 0.6 | 4.1 |
| OVX (n = 9) | 122.7 | 1.94 | 3200 | 0.19 | 0.29 | 6.7 |
| GA-treated (O + YF: n = 8) | 92.1 | 1.47 | 2971 | 0.169 | 053 | 5.3 |
| % Change (OVX) | +139%* | −62%* | +31%* | +11%* | −63%* | +63%* |
| % Change (GA-treated) | +79%* | −71%* | +22% | 0%** | −9%** | +30%** |

*p < 0.05 vs. control;
**p < 0.05 vs OVX alone (untreated)

Summary (Model 1):

A single injection of a gastrin antagonist was associated with reversal of ovariectomy-mediated bone changes (examined at 8 weeks) in a mouse model. These effects, occurred despite low circulating estrogen and high PTH levels, and were exemplified by normalization of histomorphometric parameters (mineralization, osteoclast number) and circulating bone biomarker expression consistent with anabolic effects.

Figure 47:
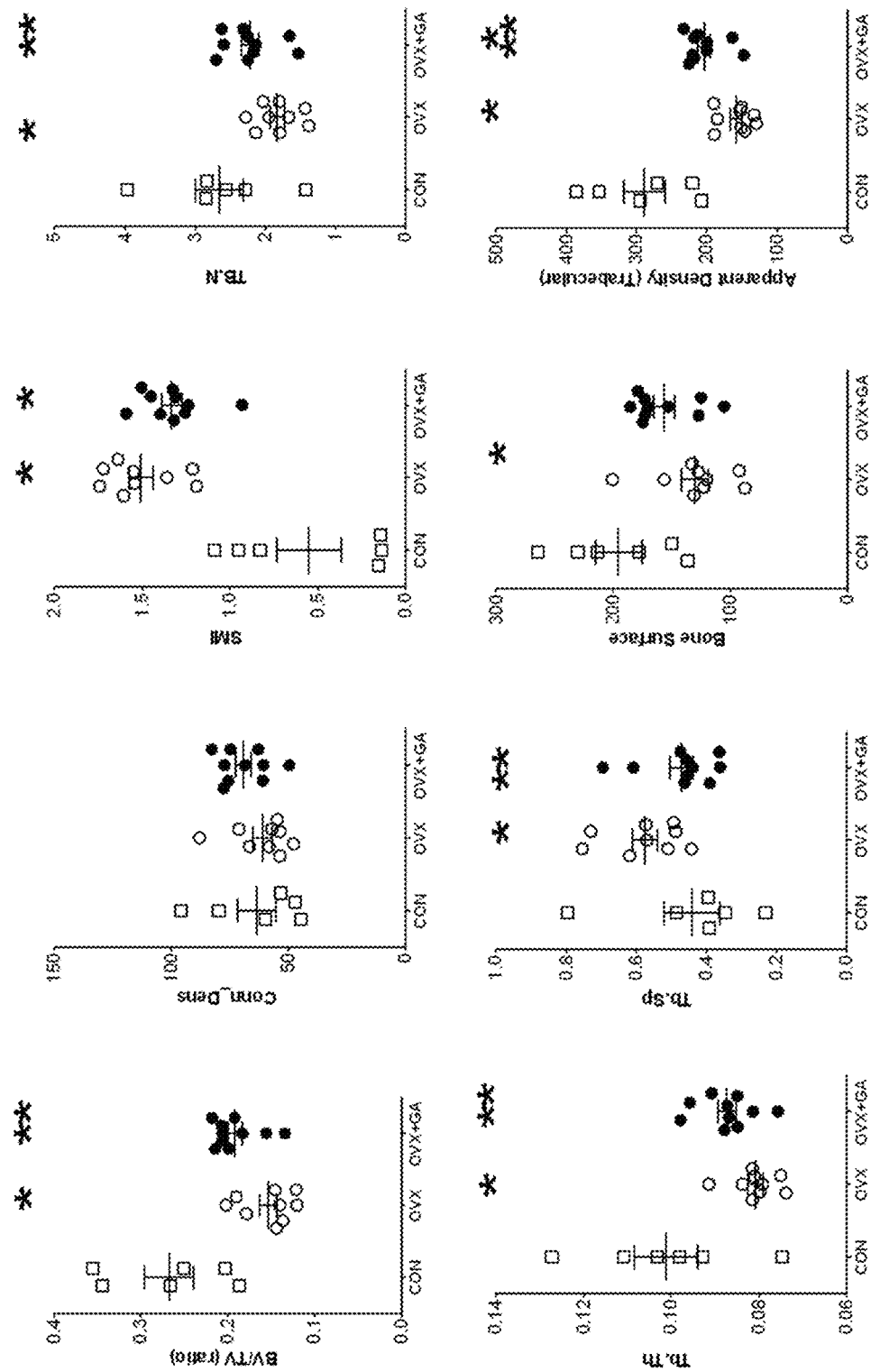
FIG. 47 is a series of graphs showing MicroCT measurements in trabecular bone in control, ovariectomized and ovariectomy CD rats treated with the gastrin antagonist. The BV/TV ratio, trabecular number (TB.N), trabecular thickness (Tb.Th), bone surface and density were all significantly decreased by ovariectomy. The structural model index (SMI) and trabecular spacing (Tb.Sp) were all increased. Gastrin antagonist treatment reversed the majority of these effects except for SMI. These results demonstrate that selectively inhibiting the gastrin receptor ameliorates bone loss in the ovariectomy model and results in microCT features consistent with a normal phenotype in CD rats. CON=control animals, OVX=ovariectomized animals, OVX+GA=gastrin antagonist treated ovariectomized animals. Mean±SEM. *p<0.05 vs. CON, **p<0.05 vs. OVX alone.

Model 2:

Rat OVX Model:

At the start of GA treatment, animals were 98 days (3.2 months) and at study termination, they were 163 days (5.4 months). An examination of trabecular bone data identified that ovariectomy significantly reduced BV/TV (0.15±0.03 vs. 0.27±0.07, p<0.05) and the density (159±26 vs. 287±71, p<0.05). The trabecular spacing (0.58±0.1 vs. 0.44±0.19, p<0.05) as well as the SMI (1.5±0.2 vs. 0.6±0.4, p<0.05) were increased (TABLE 8, FIG. 47). Gastrin antagonist treatment reversed these ovariectomy-mediated bone alterations except for the SMI (1.3±0.17) which remained increased. This was associated with a significant increase in trabecular bone density (204±27, p<0.05 vs. OVX).

TABLE 8

Trabecular Bone data results from Model 2

| Parameter | BV/TV | Conns-Dens | SMI | Tb. N | Tb. Th | Tb. Sp | Dens[&] | BS |
|---|---|---|---|---|---|---|---|---|
| Control (n = 6) | 0.268 | 63.65 | 0.551 | 2.65 | 0.10 | 0.44 | 288.6 | 195.4 |
| OVX (n = 9) | 0.153 | 61.43 | 1.508 | 1.83 | 0.08 | 0.57 | 158.5 | 130 |

TABLE 8-continued

Trabecular Bone data results from Model 2

| Parameter | BV/TV | Conns-Dens | SMI | Tb. N | Tb. Th | Tb. Sp | Dens[&] | BS |
|---|---|---|---|---|---|---|---|---|
| GA-treated (O + YF: n = 10) | 0.189 | 68.58 | 1.33 | 2.17 | 0.09 | 0.48 | 200.5 | 154 |
| % Change (OVX) | −43%* | −3% | +174%* | −31%* | −20%* | +30%* | −45%* | −34%* |
| % Change (GA-treated) | −30%** | +8% | +143%* | −18%** | −13%** | +9%** | −30%*,** | −21% |

[&]Apparent Density (trabecular);
*p < 0.05 vs. control;
**p < 0.05 vs OVX alone (untreated)

Figure 48:
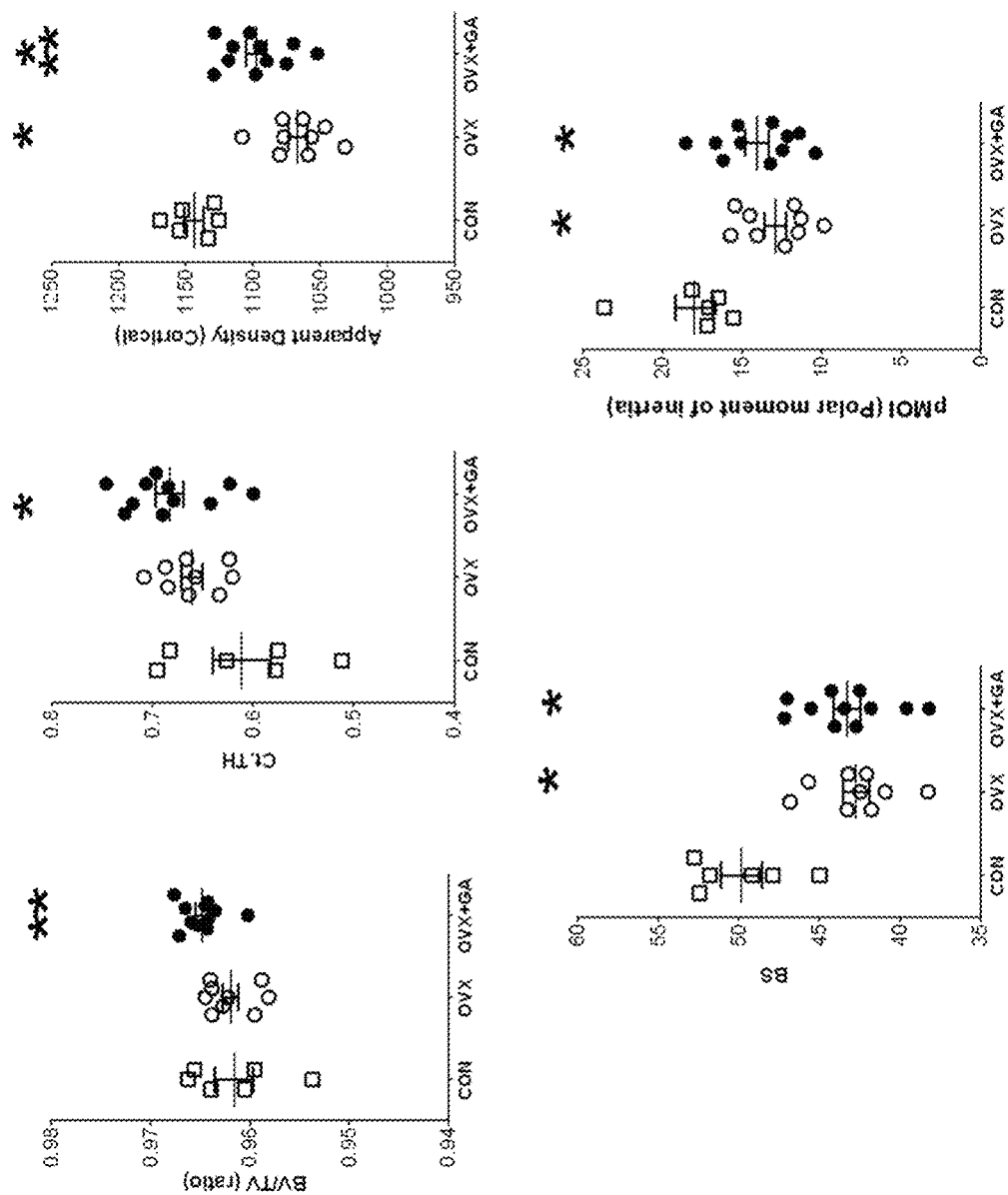
FIG. 48 is a series of graphs showing MicroCT measurements in cortical bone in control, ovariectomized and ovariectomy CD rats treated with the gastrin antagonist. The cortical density and bone surface (BS) and polar moment of inertia (pMOI) were all significantly decreased by ovariectomy. Gastrin antagonist treatment reversed the effects on density and were associated both with an increased BV/TV ratio as well as cortical thickness (Ct.TH). These results demonstrate that selectively inhibiting the gastrin receptor reverses cortical density loss in the ovariectomy model. CON=control animals, OVX=ovariectomized animals, OVX+GA=gastrin antagonist treated ovariectomized animals. Mean±SEM. *p<0.05 vs. CON, **p<0.05 vs. OVX alone.

An analysis of cortical bone parameters identified that ovariectomy significantly decreased bone surface (42.7±2.5 vs. 49.9±3, p<0.05), increased cortical thickness (0.66±0.03 vs. 0.61±0.07, p<0.05) and was associated with a decrease (1067±22 vs. 1144±17, p<0.05) in cortical density (TABLE 9, FIG. 48). Gastrin-antagonist treatment reversed the OVX-mediated decrease in density (1098±24, p<0.05 vs OVX).

TABLE 9

Cortical bone data results from Model 2

| Parameter | BV/TV | Ct. Th | Dens[&] | BS | pMOI |
|---|---|---|---|---|---|
| Control (n = 6) | 0.961 | 0.611 | 1144 | 49.85 | 18.01 |
| OVX (n = 7) | 0.961 | 0.66 | 1066 | 42.75 | 12.93 |
| GA-treated (O + YF: n = 10) | 0.965 | 0.68 | 1098 | 43.3 | 14.03 |
| % Change (OVX) | 0% | +8% | −7%* | −15%* | −28%* |
| % Change (GA-treated) | 0%** | +12%* | −4%*,** | −13%* | −22%* |

[&]Apparent Density (cortical),
*p < 0.05 vs. control;
**p < 0.05 vs OVX alone (untreated)

Figure 49:
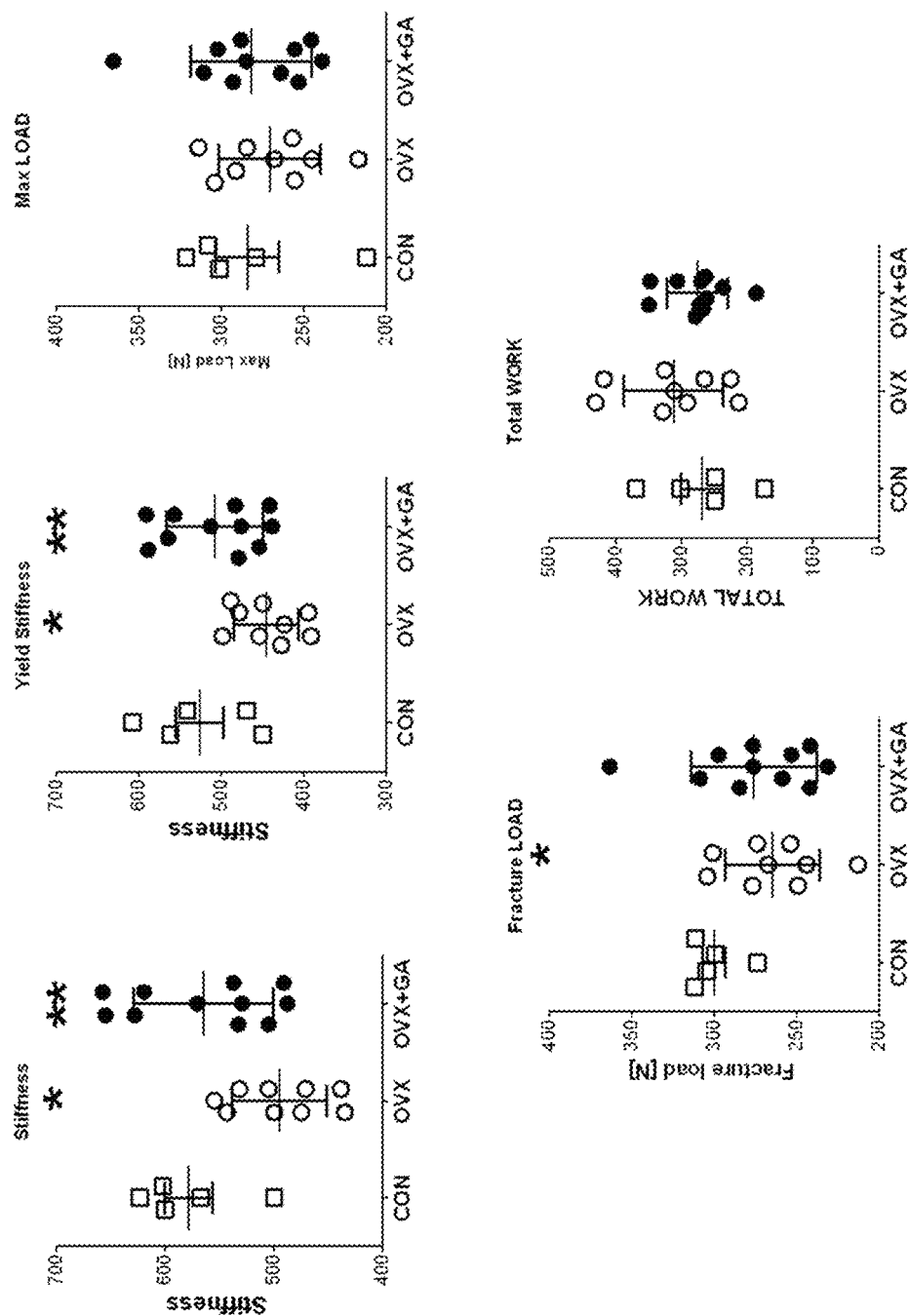
FIG. 49 is a series of graphs showing the overall strength of bone in control, untreated and gastrin-antagonist treated rats. Ovariectomy significantly decreased bone strength including stiffness, yield stiffness, as well as the fracture load for breaking Treatment with the gastrin antagonist reversed these effects. These results confirm that the strength of bones following ovariectomy is decreased and that targeting the gastrin receptor ameliorated these estrogen-mediated effects. CON=control animals, OVX=ovariectomized animals, 8 wk=short-term hypergastrinemia, 16 wk=long-term hypergastrinemia. Mean±SEM. *p<0.05 vs. CON, **p<0.05 vs. OVX alone.

Measurements of bone strength using Instron device confirmed the utility of the gastrin-antagonist in reversing the OVX-mediated bone phenotype. Ovariectomy significantly reduced (p<0.05) the bone strength (stiffness [495±43 vs. 578±48], yield stiffness [445±39 vs. 526±66], and the fracture load to breakage [265±29 vs. 300±17]). The gastrin antagonist treatment normalized these ovariectomy-mediated bone alterations (TABLE 10, FIG. 49).

TABLE 10

Bone strength data

| Parameter | Stiffness | Yield (Stiffness) | Max Load | Fracture Load | Total Work |
|---|---|---|---|---|---|
| Control (n = 6) | 579 | 526 | 284 | 300 | 268 |
| OVX (n = 9) | 495 | 445 | 271 | 265 | 312 |
| GA-treated (O + YF: n = 10) | 565 | 508 | 282 | 276 | 276 |
| % Change (OVX) | −14%* | −14%* | −5% | −12%* | +16% |
| % Change (GA-treated) | −2%** | −2%** | 0% | −8% | 0% |

*p < 0.05 vs. control;
**p < 0.05 vs OVX alone (untreated)

Figure 50:
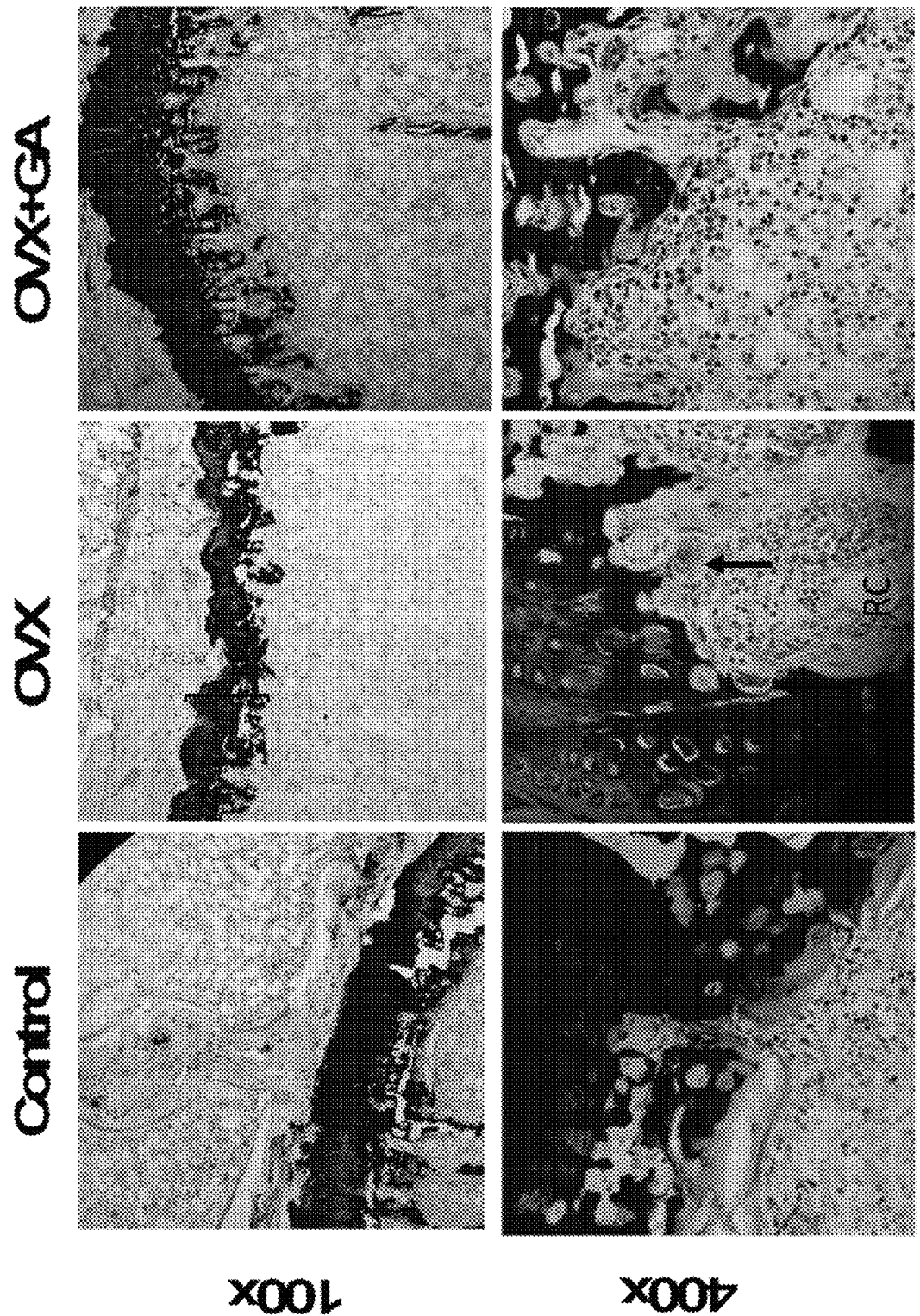
FIG. 50 is a series of photomicrographs showing Toluidine-blue, TRAP-stained femurs from control and ovariectomized CD rats treated with the gastrin antagonist (OVX+GA) or vehicle (OVX). Patterns of bone mineralization (variably decreased), resorption cavities (RC) (increased) and osteoclasts (stained multinuclear cells (two arrows): increased) were affected by OVX. These effects were reversed by drug treatment. In one aspect, this reflects that targeting CCK2 receptors normalizes bone morphology irrespective of low estrogen levels.

Histomorphometry identified altered bone mineralization with an increased resorption cavities as well as significantly increased (p<0.05) numbers of TRAP-positive osteoclasts (11±3 vs. 2±2, p<0.05) in the OVX rats. Gastrin-antagonist treatment reversed these phenomena (FIG. 50).

Figure 51:
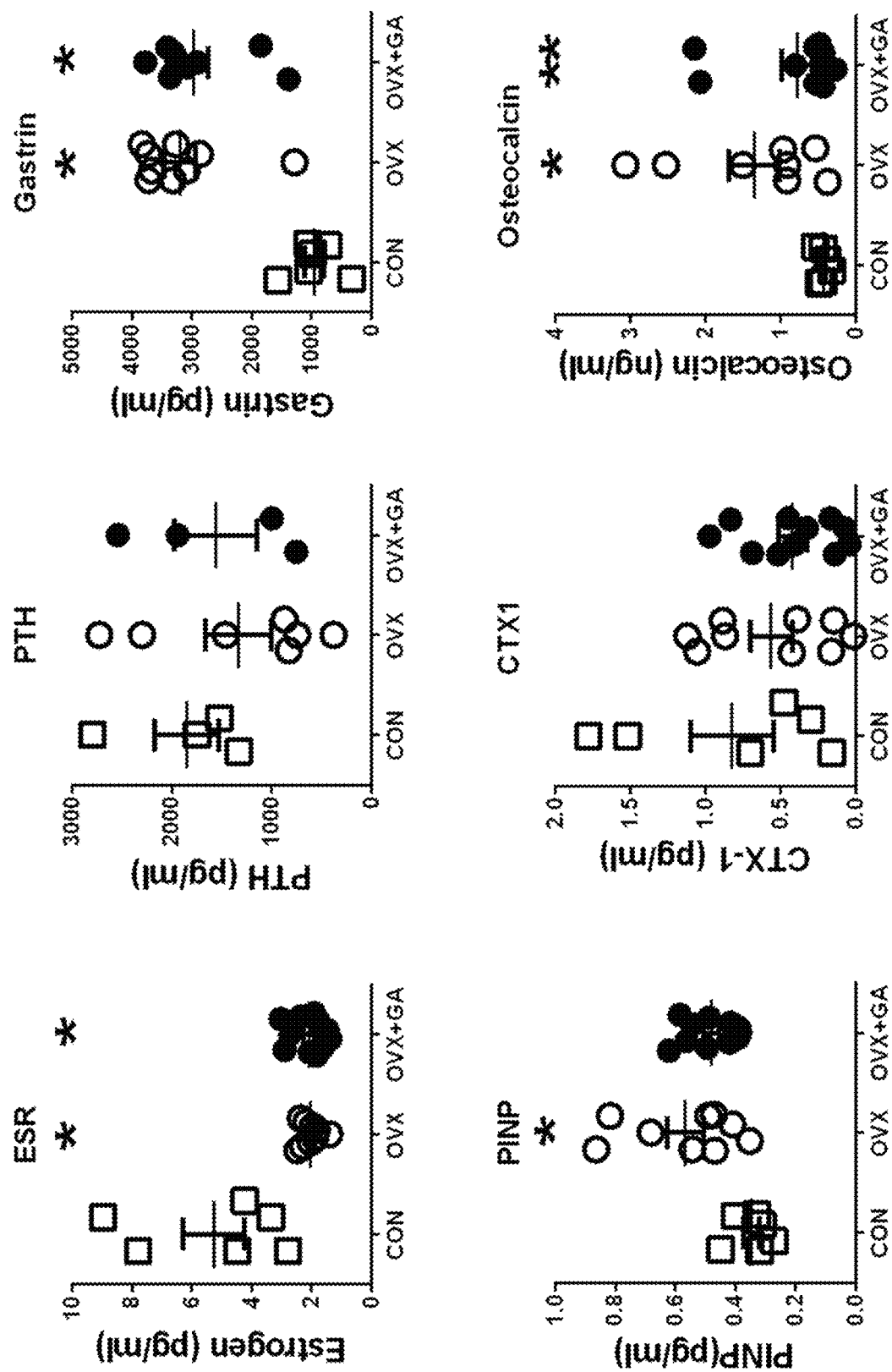
FIG. 51 is a series of photomicrographs showing the effects of gastrin antagonist treatment on circulating hormone levels in the ovariectomized rat model. Estrogen was significantly decreased while gastrin was elevated by ovariectomy. Gastrin antagonist treatment had no significant effect. Ovariectomy increased PINP and osteocalcin. The gastrin antagonist inhibited these effects. In one aspect, these results demonstrate that markers of bone activity engendered by ovariectomy are normalized by targeting the gastrin receptor. CON=control animals, OVX=ovariectomized animals, OVX+GA=gastrin antagonist treated ovariectomized animals. Mean±SEM. *p<0.05 vs. CON, **p<0.05 vs. OVX alone.

Ovariectomy significantly (p<0.05) decreased circulating estrogen (2.1±0.3 pg/ml vs. 5.3±2.5) and was associated with an increase in gastrin (3200±789 pg/ml vs. 954±406). Treatment with the antagonist had no significant effect on estrogen or gastrin (TABLE 11, FIG. 51). Circulating bone biomarkers were also altered by OVX. Specifically, both PINP (0.57±0.18 ng/ml vs. 0.35±0.06, p<0.05) and osteocalcin was elevated (1.35±0.9 ng/ml vs. 0.43±0.07, p<0.05). Treatment with the antagonist attenuated each of these ovariectomy-mediated alterations.

TABLE 11

Circulating Blood Marker Levels in each of the three Groups

| Parameter | ESR | PTH | Gastrin | PINP | CTX1 | Osteocalcin |
|---|---|---|---|---|---|---|
| Control (n = 6) | 5.28 | 1852 | 954 | 0.34 | 0.82 | 0.43 |
| OVX (n = 9) | 2.07 | 1332 | 3134 | 0.57 | 0.56 | 1.35 |
| GA-treated (O + YF: n = 10) | 2.1 | 1562 | 2971 | 0.48 | 0.42 | 0.80 |
| % Change (OVX) | −60%* | −28% | +228%* | +68%* | −31% | +228%* |
| % Change (GA-treated) | −60%* | −15% | +183%* | +41% | −49% | +81%** |

*p < 0.05 vs. control;
**p < 0.05 vs OVX alone (untreated)

Summary (Model 2):

A single injection of a gastrin antagonist was associated with reversal of ovariectomy-mediated bone changes (examined at 8 weeks) in a rat model. These effects, occurred despite low circulating estrogen and high gastrin levels, and were exemplified by normalization of histomorphometric parameters (mineralization, osteoclast number) and circulating bone biomarker expression consistent with an anabolic effect.

Figure 52:
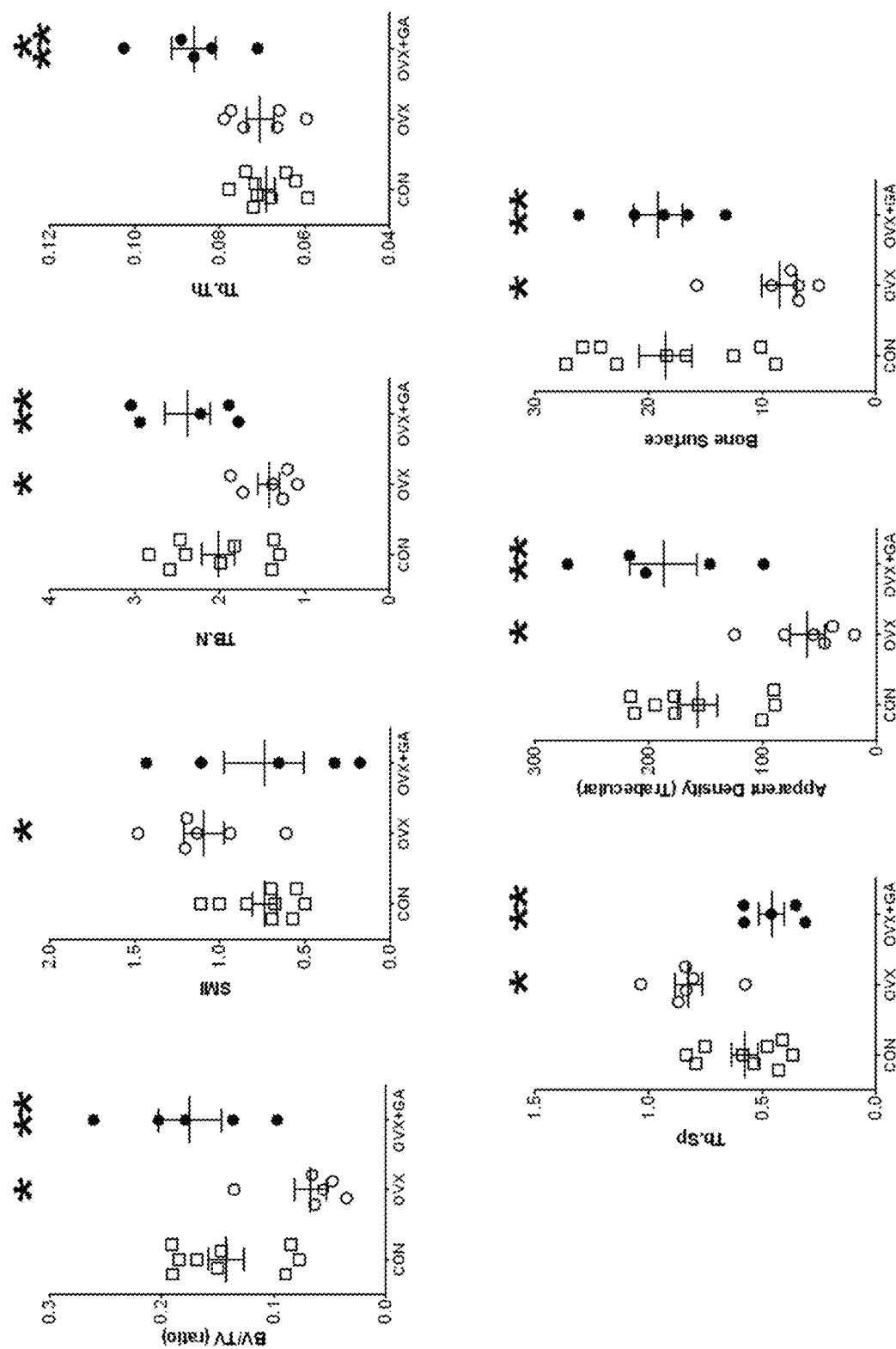
FIG. 52 is a series of graphs showing MicroCT measurements in trabecular bone in control, ovariectomized and ovariectomy Mastomys treated with the gastrin antagonist. The BV/TV ratio, trabecular number (TB.N), density and bone surface were all significantly decreased by ovariectomy, while the structural model index (SMI) and trabecular spacing (Tb.Sp) were increased. Gastrin antagonist treatment reversed these effects and was associated with an increase in trabecular thickness (Tb.Th). These results demonstrate that selectively inhibiting the gastrin receptor ameliorates bone loss in the ovariectomy model and results in microCT features consistent with a normal phenotype in Mastomys. CON=control animals, OVX=ovariectomized animals, OVX+GA=gastrin antagonist treated ovariectomized animals. Mean±SEM. *p<0.05 vs. CON, **p<0.05 vs. OVX alone.

Model 3: Mastomys OVX Model:

At the start of GA treatment, animals were 121 days (4.0 months) and at study termination, 180 days (6.0 months). Ovariectomy significantly reduced the BV/TV ratio (0.06±0.03 vs. 0.14±0.05, p<0.05), the trabecular number (1.4±0.3 vs. 2.0±0.6, p<0.05), and bone surface (8.5±3.7 vs. 18.5±2.3, p<0.05), and increased the SMI (1.1±0.3 vs. 0.74±0.21, p<0.05), as well as trabecular spacing (0.82±0.15 vs. 0.57±0.17, p<0.05) (TABLE 12, FIG. 52). This was associated with a significant decrease in trabecular bone density (60.6±37 vs. 157±51, p<0.05). Gastrin antagonist-treatment reversed these ovariectomy-mediated bone alterations normalizing the trabecular bone density (187±66). The drug was also associated with an increase in trabecular number (2.4±0.6, p<0.05 vs. control) and thickness (0.08±0.01, p<0.05 vs. control).

TABLE 12

Trabecular Bone data results from Model 3

| Parameter | BV/TV | Conns-Dens | SMI | Tb. N | Tb. Th | Tb. Sp | Dens[&] | BS |
|---|---|---|---|---|---|---|---|---|
| Control (n = 9) | 0.142 | 97.23 | 0.74 | 2.02 | 0.069 | 0.576 | 156.95 | 18.5 |
| OVX (n = 6) | 0.067 | 66.74 | 1.09 | 1.42 | 0.071 | 0.825 | 60.6 | 8.5 |
| GA-treated (O + YF: n = 5) | 0.175 | 124.1 | 0.74 | 2.38 | 0.086 | 0.457 | 187.1 | 19.2 |
| % Change (OVX) | −53%* | −31% | +48%* | −30%* | +2% | +43%* | −61%* | −54%* |
| % Change (GA-treated) | +27%** | +28% | 0% | +18%** | +25%*,** | −20%** | +19%** | +4%** |

[&]Apparent Density (trabecular);
*$p < 0.05$ vs. control;
**$p < 0.05$ vs OVX alone (untreated)

Figure 53:
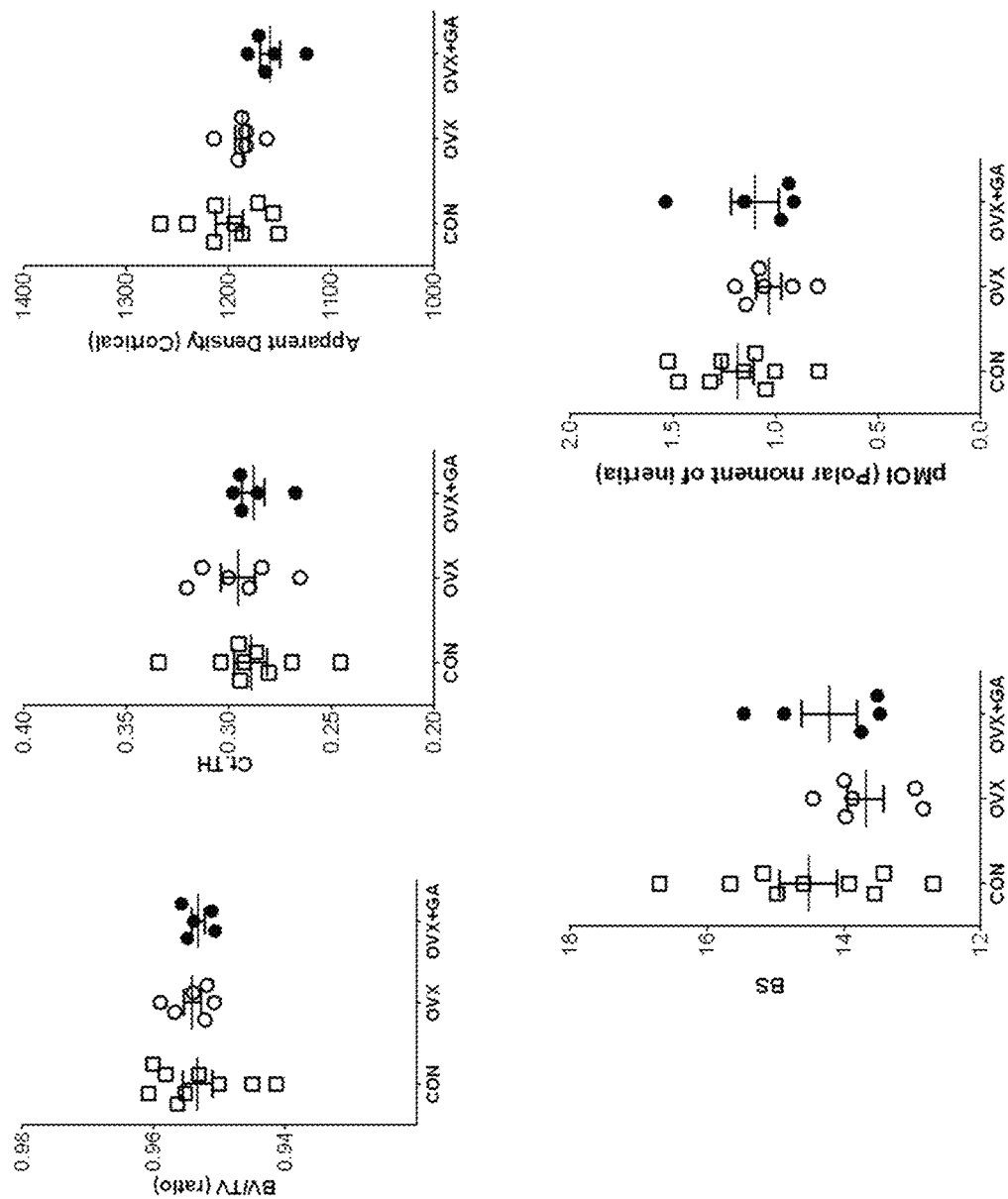
FIG. 53 is a set of graphs showing MicroCT measurements in cortical bone in control, ovariectomized and ovariectomy Mastomys treated with the gastrin antagonist. None of the categories measured were significantly affected by ovariectomy or altered by gastrin antagonist treatment. CON=control animals, OVX=ovariectomized animals, OVX+GA=gastrin antagonist treated ovariectomized animals. Mean±SEM.

An assessment of cortical bone parameters identified that ovariectomy did not significantly any cortical bone parameters (TABLE 13, FIG. 53). Gastrin antagonist-treatment had no effect in ovariectomized animals.

TABLE 13

Cortical bone data results from Model 3

| Parameter | BV/TV | Ct. Th | Dens[&] | BS | pMOI |
|---|---|---|---|---|---|
| Control (n = 9) | 0.955 | 0.293 | 1215 | 14.42 | 1.16 |
| OVX (n = 6) | 0.954 | 0.295 | 1187 | 13.69 | 1.03 |
| GA-treated (O + YF: n = 5) | 0.953 | 0.288 | 1159 | 14.21 | 1.10 |
| % Change (OVX) | 0 | 0 | −2% | −5% | −10% |
| % Change (GA-treated) | 0 | −1% | −4% | −1% | −4% |

[&]Apparent Density (cortical),
*$p < 0.05$ vs. control;
**$p < 0.05$ vs OVX alone (untreated)

Figure 54:
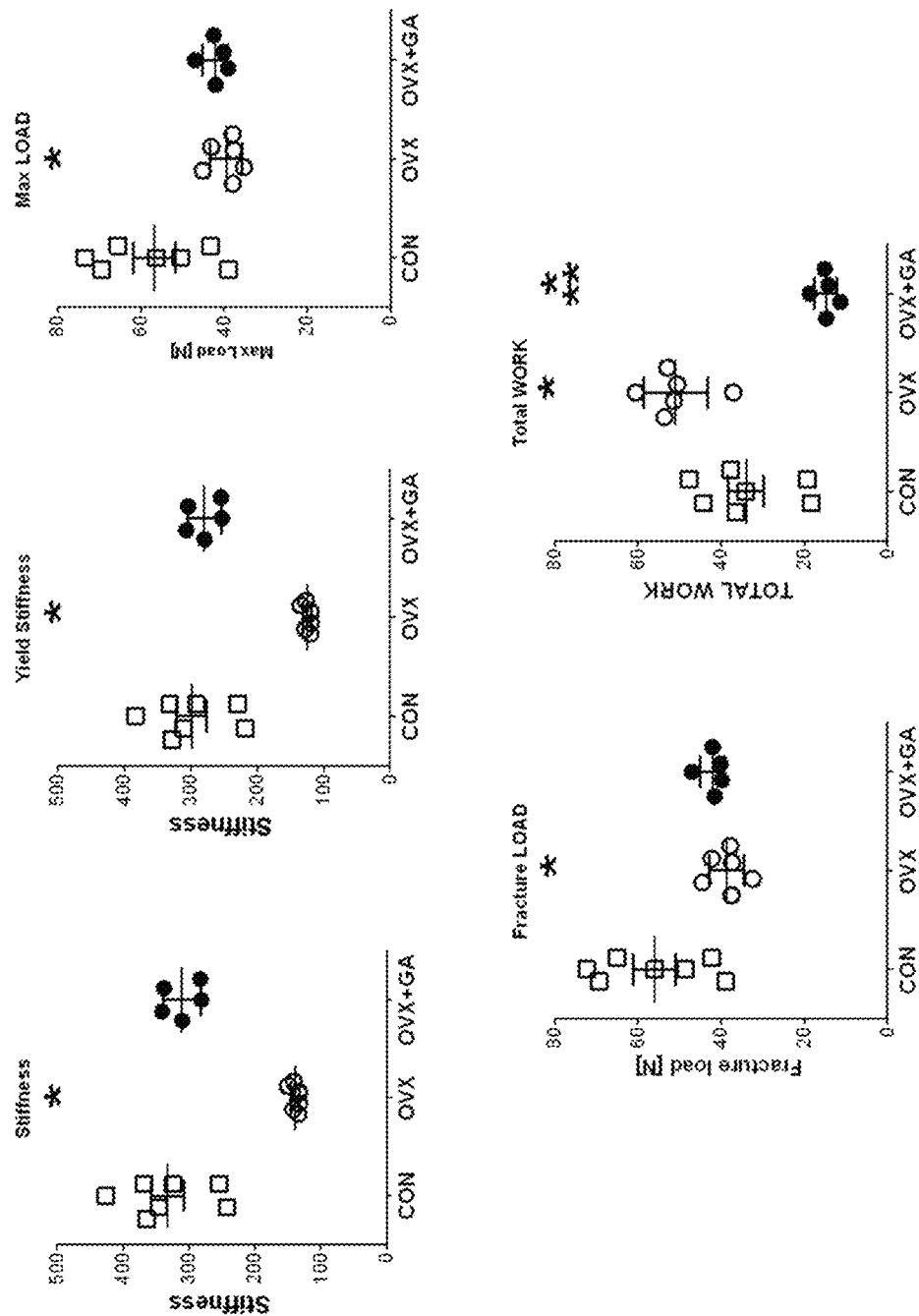
FIG. 54 is a set of graphs showing the overall strength of bone in control, untreated and gastrin-antagonist treated Mastomys. Ovariectomy significantly decreased bone strength including stiffness, yield stiffness, as well as the maximal and fracture load for breaking. The total work was increased. Treatment with the gastrin antagonist reversed these effects. These results confirm that the strength of bones following ovariectomy is decreased and that targeting the gastrin receptor ameliorated these estrogen-mediated effects. CON=control animals, OVX=ovariectomized animals, 8 wk=short-term hypergastrinemia, 16 wk=long-term hypergastrinemia. Mean±SEM. *p<0.05 vs. CON, **p<0.05 vs. OVX alone.

Measurements of bone strength using the Instron device confirmed the utility of the gastrin-antagonist in reversing the OVX-mediated bone phenotype. Ovariectomy significantly reduced ($p<0.05$) the bone strength (stiffness [138±7 vs. 332±65], yield stiffness [125±6 vs. 299±59], the fracture load to breakage [38±4 vs. 56±13]) and increased the total work required to break the bone [51±7.7 vs. 34±11.6, $p<0.05$]. The gastrin antagonist treatment normalized these ovariectomy-mediated bone alterations (TABLE 14, FIG. 54).

TABLE 14

Bone strength data

| Parameter | Stiffness | Yield (Stiffness) | Max Load | Fracture Load | Total Work |
|---|---|---|---|---|---|
| Control (n = 7) | 332 | 299 | 56.8 | 56.1 | 34 |
| OVX (n = 6) | 139 | 125 | 39.5 | 38.7 | 51 |
| GA-treated (O + YF: n = 5) | 311 | 280 | 42.2 | 42.1 | 14.8 |
| % Change (OVX) | −58%* | −58%* | 40%* | −31%* | +50%* |
| % Change (GA-treated) | −6%** | −6%** | −25% | −25% | 55%*,** |

*$p < 0.05$ vs. control;
**$p < 0.05$ vs OVX alone (untreated)

Figure 55:
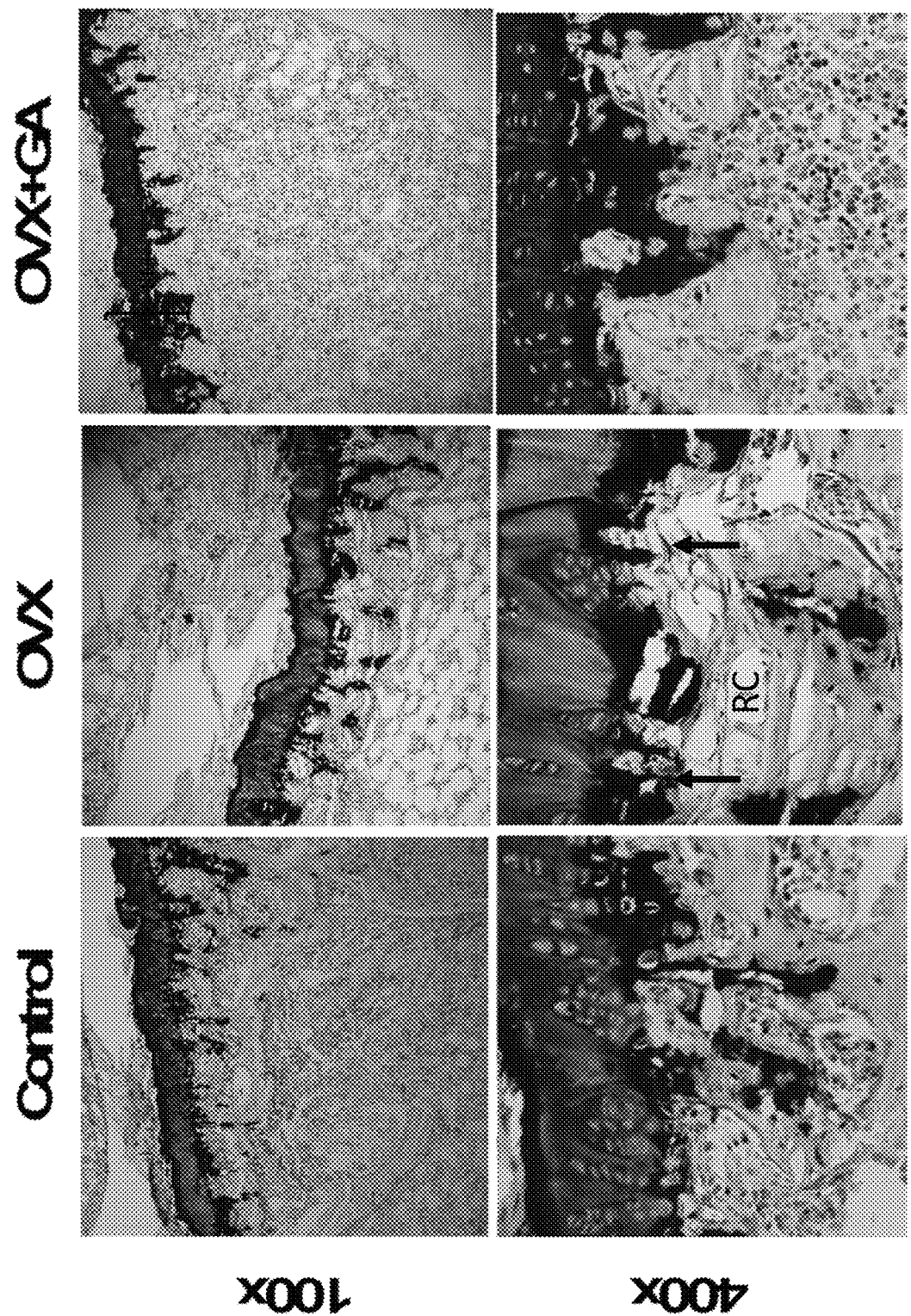
FIG. 55 is a set of photomicrographs showing Toluidine-blue, TRAP-stained femurs from control and ovariectomized Mastomys treated with the gastrin antagonist (OVX+GA) or vehicle (OVX). Patterns of bone mineralization (BM: decreased), resorption cavities (RC: increased) and osteoclasts (stained multinuclear cells (two arrows): increased) were affected by OVX. These effects were reversed by drug treatment. We interpret this to reflect that targeting CCK2 receptors normalizes bone morphology irrespective of low estrogen levels and constitutive gastrin receptor activation.

Histomorphometry identified decreased bone mineralization with an increased resorption cavities as well as significantly increased ($p<0.05$) numbers of TRAP-positive osteoclasts (27±11 vs. 9±3, $p<0.05$) in the OVX Mastomys. The gastrin-antagonist treatment reversed these phenomena (FIG. 55).

Figure 56:
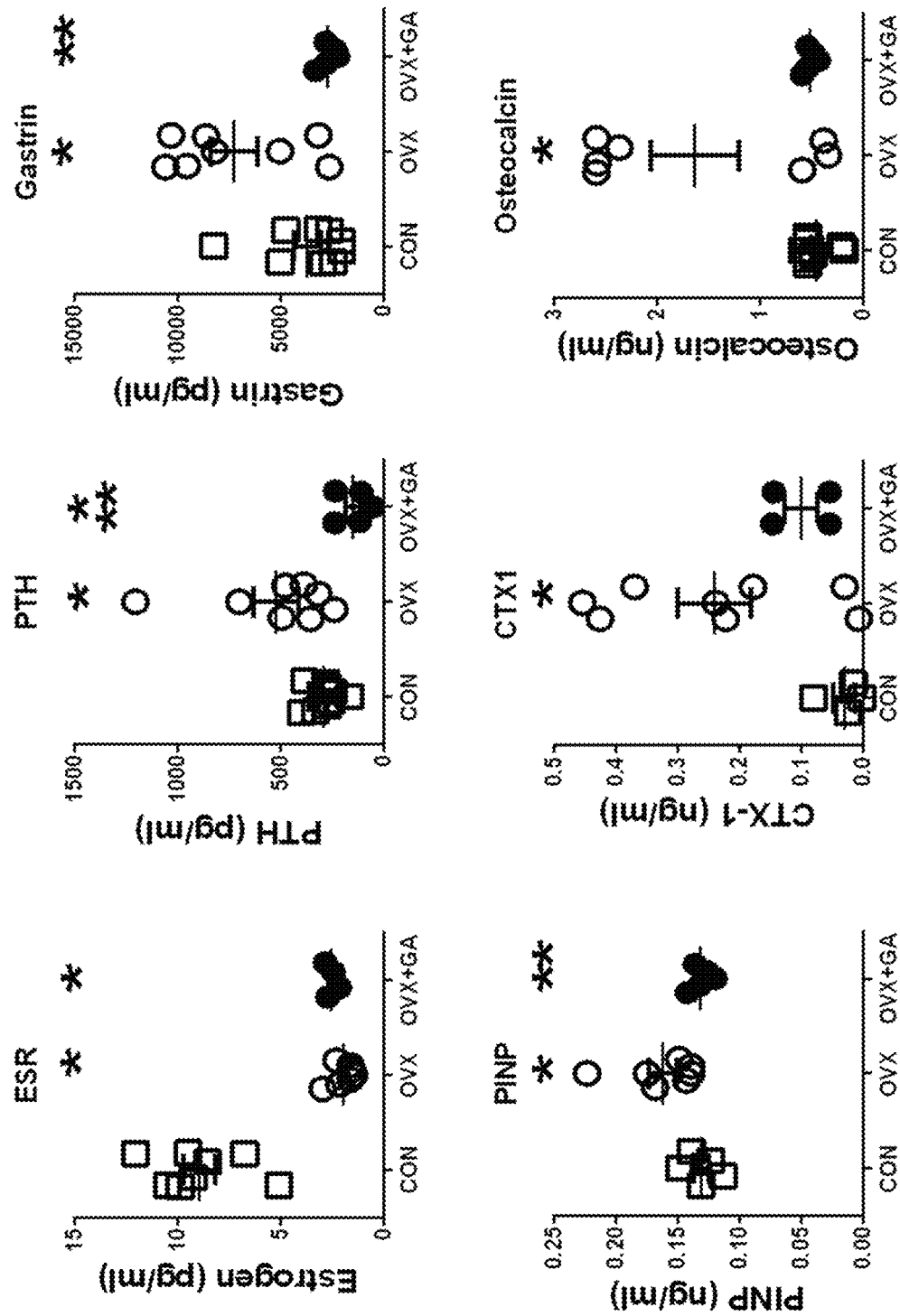
FIG. 56 is a set of graphs showing the effects of gastrin antagonist treatment on circulating hormone levels in the ovariectomized Mastomys model. Estrogen was significantly decreased while PTH and gastrin were elevated by ovariectomy. Gastrin antagonist treatment reversed the effects on PTH and gastrin. Ovariectomy significantly increased PINP, CTX-1 and osteocalcin. The gastrin antagonist inhibited these effects. We interpret these results to reflect that markers of bone activity engendered by ovariectomy are normalized by targeting the gastrin receptor. CON=control animals, OVX=ovariectomized animals, OVX+GA=gastrin antagonist treated ovariectomized animals. Mean±SEM. *p<0.05 vs. CON, **p<0.05 vs. OVX alone.

Ovariectomy significantly ($p<0.05$) decreased circulating estrogen (1.9±0.6 pg/ml vs. 8.9±2.1) and was associated with an increase in PTH (523±308 pg/ml vs. 290±71) and gastrin (7265±3198 pg/ml vs. 3705±2015). Treatment with the antagonist reversed the ovariectomy-mediated increase in gastrin (2704±430) and PTH (150±37) (TABLE 15, FIG. 56). Circulating bone biomarkers were also altered by OVX. Specifically, PINP was increased (0.16±0.03 ng/ml vs. 0.13±0.01, $p<0.05$) as was CTx-1 (0.24±0.17 ng/ml vs. 0.03±0.03, $p<0.05$) while osteocalcin was elevated (1.6±1.1 ng/ml vs. 0.4±0.16, $p<0.05$). Treatment with the antagonist attenuated each of these three ovariectomy-mediated alterations.

TABLE 15

Circulating Blood Marker Levels in each of the three Groups

| Parameter | ESR | PTH | Gastrin | PINP | CTx-1 | Osteocalcin |
|---|---|---|---|---|---|---|
| Control (n = 7) | 8.95 | 290 | 3704 | 0.13 | 0.03 | 1.00 |
| OVX (n = 6) | 1.95 | 523 | 7265 | 0.16 | 0.24 | 3.6 |
| GA-treated (O + YF: n = 5) | 2.54 | 151 | 2703 | 0.13 | 0.1 | 1.13 |
| % Change (OVX) | −78%* | +80%* | +96%* | +23%* | +700%* | +230%[#] |
| % Change (GA-treated) | −70%* | −48%*,** | −27%** | 0%*,** | +230% | +13% |

*$p < 0.05$ vs. control;
**$p < 0.05$ vs OVX alone (untreated),
[#]$p = 0.07$ vs. control Summary (Model 3):

A single injection of a gastrin antagonist was associated with reversal of ovariectomy-mediated bone changes (examined at 8 weeks) in the Mastomys model. These effects, occurred despite low circulating estrogen, and were exemplified by normalization of histomorphometric parameters (mineralization, osteoclast number) and circulating bone biomarker expression consistent with anabolic effects Summary (Models 1, 2, and 3):

A single injection of the gastrin antagonist (10-20 µMg body weight) reversed ovariectomy-mediated bone loss and strength either normalizing or trending toward normalization in three of 3 models. This occurred despite low circulating estrogen and high PTH levels and was associated with modification of pro-bone mass signaling.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method for treating osteoporosis in a human subject in need thereof, comprising administering to the human subject at least one dose of a therapeutically effective amount of YF476, thereby treating the osteoporosis.

2. The method of claim 1, wherein the human subject is a post-menopausal female.

3. The method of claim 1, wherein the YF476 is administered orally, subcutaneously, or intravenously.

4. The method of claim 1, wherein the YF476 is administered to the human subject orally in a dose ranging from 20-100 mg.

5. The method of claim 1, wherein the treatment period is for at least 8 weeks.

6. The method of claim 1, wherein the human subject has decreased ovarian function, ovarian failure, neoplastic hypergastrinemia, hypergastrinemia associated with acid suppressive pharmacology, has had an ovariectomy or any combination thereof.

7. The method of claim 1, wherein the treatment time period is sufficient to increase trabecular BV/TV in the human subject by at least 23%.

8. The method of claim 1, wherein the treatment time period is sufficient to increase trabecular bone density in the human subject by at least 26%.

9. The method of claim 1, wherein the treatment time period is sufficient to increase trabecular bone density in the human subject by at least 18%.

10. The method of claim 1, wherein the treatment period is sufficient to increase cortical bone density in the human subject by at least 3%.

11. A method for treating osteoporosis in a human subject in need thereof, comprising administering to the human subject at least one dose of a therapeutically effective amount of a YF476 for a treatment time period sufficient to reduce the level of circulating CTx-1 in the human subject by at least 25%.

12. The method of claim 11, wherein the human subject is a post-menopausal female.

13. The method of claim 11, wherein the YF476 is administered orally, subcutaneously, or intravenously.

14. The method of claim 11, wherein the YF476 is administered to the human subject orally in a dose ranging from 20-100 mg.

15. The method of claim 11, wherein the treatment period is for at least 8 weeks.

16. The method of claim 11, wherein the human subject has decreased ovarian function, ovarian failure, neoplastic hypergastrinemia, hypergastrinemia associated with acid suppressive pharmacology, has had an ovariectomy or any combination thereof.

17. The method of claim 11, wherein the treatment time period is sufficient to increase trabecular BV/TV in the human subject by at least 23%.

18. The method of claim 11, wherein the treatment time period is sufficient to increase trabecular bone density in the human subject by at least 26%.

19. The method of claim 11, wherein the treatment time period is sufficient to increase trabecular bone density in the human subject by at least 18%.

20. The method of claim 11, wherein the treatment period is sufficient to increase cortical bone density in the human subject by at least 3%.

21. A method for treating osteoporosis in a post-menopausal female in need thereof, comprising orally administering to the post-menopausal female 20-100 mg of YF476 daily for a treatment time period sufficient to reduce the level of circulating CTx-1 in the post-menopausal female by at least 25%, wherein the treatment period is for at least 8 weeks.

22. The method of claim 21, wherein the post-menopausal female has decreased ovarian function, ovarian failure, neoplastic hypergastrinemia, hypergastrinemia associated with acid suppressive pharmacology, has had an ovariectomy or any combination thereof.

23. The method of claim 21, wherein the treatment time period is sufficient to increase trabecular BV/TV in the post-menopausal female by at least 23%.

24. The method of claim 21, wherein the treatment time period is sufficient to increase trabecular bone density in the post-menopausal female by at least 26%.

25. The method of claim 21, wherein the treatment time period is sufficient to increase trabecular bone density in the post-menopausal female by at least 18%.

26. The method of claim 21, wherein the treatment period is sufficient to increase cortical bone density in the post-menopausal female by at least 3%.

* * * * *

UNITED STATES PATENT AND TRADEMARK OFFICE
CERTIFICATE OF CORRECTION

| | | |
|---|---|---|
| PATENT NO. | : 10,709,714 B2 | |
| APPLICATION NO. | : 14/550233 | |
| DATED | : July 14, 2020 | |
| INVENTOR(S) | : Modlin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 79 days.

Signed and Sealed this
Thirteenth Day of December, 2022

Katherine Kelly Vidal
*Director of the United States Patent and Trademark Office*